US007960607B2

(12) United States Patent
Sanz Molinero

(10) Patent No.: US 7,960,607 B2
(45) Date of Patent: Jun. 14, 2011

(54) PLANTS HAVING MODIFIED GROWTH CHARACTERISTICS AND A METHOD FOR MAKING THE SAME

(75) Inventor: Ana Isabel Sanz Molinero, Gentbrugge (BE)

(73) Assignee: Cropdesign N.V., Zwijnaarde (BE)

(*) Notice: Subject to any disclaimer, the term of this patent is extended or adjusted under 35 U.S.C. 154(b) by 134 days.

(21) Appl. No.: 10/537,897

(22) PCT Filed: Dec. 24, 2003

(86) PCT No.: PCT/EP03/51104
§ 371 (c)(1),
(2), (4) Date: Jun. 7, 2005

(87) PCT Pub. No.: WO2004/058980
PCT Pub. Date: Jul. 15, 2004

(65) Prior Publication Data

US 2006/0048239 A1 Mar. 2, 2006

(30) Foreign Application Priority Data

Dec. 24, 2002 (EP) .................................... 02080654

(51) Int. Cl.
*C12N 15/82* (2006.01)

(52) U.S. Cl. ......................... 800/278; 800/287; 800/290

(58) Field of Classification Search .................. 800/278, 800/298, 320, 290, 287
See application file for complete search history.

(56) References Cited

U.S. PATENT DOCUMENTS

| | | | | |
|---|---|---|---|---|
| 5,859,337 | A * | 1/1999 | Gasser et al. | 800/298 |
| 2006/0021088 | A1 | 1/2006 | Inze et al. | |

FOREIGN PATENT DOCUMENTS

| | | | |
|---|---|---|---|
| EP | 1 033 405 | A | 9/2000 |
| EP | 1 230 843 | A | 8/2002 |
| WO | 96/39020 | A | 12/1996 |
| WO | WO 01/36598 | A1 * | 5/2001 |
| WO | 01/90343 | A | 11/2001 |
| WO | WO 2004/058980 | | 7/2004 |

OTHER PUBLICATIONS

Sakamoto et al (2000, Gene 48:23-32).*
Merriam Webster Online Dictionary. 2005, www.m-w.com/home.html.*
Bowie et al, Science 247:1306-1310, 1990.*
McConnell et al, Nature 411 (6838):709-713, 2001.*
Kano-Murakami et al (1993, FEBS 334:365-368).*
Payne et al (1999, Development 126:671-682).*
Pineda et al (2001, Accession No. AAD06454).*
Bowie et al, Deciphering the message in protein sequenes: tolerance to amino acid substituition, Science 247:1306-1310 (1990).*
McConnell et al, Role of Phabulosa and Phavoluta in determining radial patterning in shoots, Nature 411:709-713 (2001).*
Kano-Murakami et al, A rice homeotic gene, OSH1, causes unusual phenotypes in transgenic tobaccod. FEBS 224(3):365-368 (1993).*
Payne et al, Heterologous myb genes distinct from GL1 enhance trichome production when overexpressed in Nicotiana tabacum. Development 126:671-682 (1999).*
Ayala and Kiger, In Modern Genetics, second edition, The Benjamin/Cummings Publishing Company, Menlo Park, California, 1984.*
Takatsuji et al (1994, The Plant Cell (6):947-958).*
Ciftci-Yilmaz et al (2008, Cell. Mol. Life Sci. (65):1150-1160).*
Fourgoux-Nicol et al (1999, Plant Molecular Biology 40 :857-872).*
Takatsuji (1996, Biochemical and Biophysical Research Communication 224:219-223).*
J.C. Kim et al., "A novel cold-inducible zinc finger protein from soybean, SCOF-1, enhances cold tolerance in transgenic plants", Plant Journal, Blackwell Scientific Publications, vol. 25, No. 3, Feb. 2001, pp. 247-259, XP002973197.
H. Takatsuji, "Zinc-Finger Proteins: The Classical Zinc Finger Emerges in Contemporary Plant Science", Plant Molecular Biology, NIJHOFF Publishers, vol. 39, No. 6, Apr. 1999, pp. 1073-1078, XP001005447.
H. Sakamoto, "Expression of a subset of the Arabidopsis Cys2/His2-type zinc-finger protein gene family under water stress", Gene, Elsevier Biomedical Press, vol. 248, No. 1-2, May 2000, pp. 23-32, XP004198793.
Ren et al, "Particle bombardment and its application to transformation of cereal crops", Journal of Biology, vol. 18, No. 4, pp. 29-32, Aug. 2001 (with English Abstract).
Chinese Office Action dated Apr. 30, 2010, issued in connection with Chinese Patent Application No. 200380107555.6.
Chinese Office Action dated Sep. 11, 2009, issued in connection with Chinese Patent Application No. 200380107555.6.
Hensgens et al, "Transient and stable expression of *gusA* fusions with rice genes in rice, barley and perennial ryegrass", Plant Molecular Biology 22:1101-1127, 1993.
Van der Maas et al, Stable transformation and long-term expression of the *gusA* reporter gene in callus lines of perennial ryegrass (*Lolium perenne L.*), Plant Molecular Biology 24:401-405, 1994.
N. Alexandrov et al., "*Arabidopsis thaliana* DNA fragment SEQ ID No: 72617", Database EMBL [Online], Oct. 18, 2000, XP002283128, Database accession No. AAC52840.
N. Alexandrov et al., "*Arabidopsis thaliana* protein fragment SEQ ID No: 72618" Database ENBK [Online], XP002283129, Database accession No. AAG56488, 2000.
De Veylder et al., "Control of proliferation, endoreduplicaiton and differentiation by the *Arabidopsis* E2Fa-DPa transcription factor", EMBO Journal, Oxford University Press, vol. 21, No. 6, Mar. 15, 2002, pp. 1360-1368, XP002227182.

(Continued)

*Primary Examiner* — Stuart F. Baum
(74) *Attorney, Agent, or Firm* — Nixon & Vanderhye P.C.

(57) ABSTRACT

The present invention concerns a method for modifying the growth characteristics of plants by modifying expression in a plant of a nucleic acid sequence encoding a 2×C2H2 zinc finger protein and/or modifying level and/or activity in a plant of a 2×C2H2 zinc finger protein. The invention also relates to transgenic plants having modified growth characteristics, which plants have modified expression of a nucleic acid encoding a 2×C2H2 zinc finger protein. For example yield of crop plants are improved by the methods of the present invention.

14 Claims, 17 Drawing Sheets

OTHER PUBLICATIONS

Vandepoele et al., "Genome-wide analysis of core cell cycle genes in *Arabidopsis*", Plant Cell, American Society of Plant Physiologists, vol. 14, No. 4, Apr. 2002, pp. 903-916, XP002259203.

Lin et et al, Database EMBL, *Arabidopsis thaliana* chromosome 1 BAC T8L23 genomic sequence, complete sequence EMBL AC079733, 2000.

Kleinow et al, GenBank Accession No. AF250337, the *Arabidopsis thaliana* zinc finger protein AZF2 (AZF2) mRNA, complete cds., Sep. 6, 2000.

Iida et al, "A zinc finger protein RHL41 mediates the light acclimatization response in *Arabidopsis*", Plant J. Oct. 2000; 24(2):191-203.

Kleinow et al, "Functional identification of an *Arabidopsis* Snf4 ortholog by screening for heterologous multicopy suppressors of *snf4* deficiency in yeast", The Plant Journal (2000); 23(1):115-1122.

Sakamoto et al, "*Arabidopsis* Cys2/His2-type zinc-finger proteins function as transcription repressors under drought, cold, and high-salinity stress conditions", Plant Physiol. Sep. 2004; 136(1):2734-2746.

Temple et al, Down-regulation of specific members of the glutamine synthetase gene family in alfalfa by antisense RNA technology, Plant Mol. Biol. Jun. 1998; 37(3):535-547.

Claims of copending U.S. Appl. No. 10/531,475, filed Jul. 13, 2009.

* cited by examiner

SEQ ID NO 1: Arabidopsis thaliana STZ cDNA (CDS1536)

AATGGCGCTCGAGGCTCTTACATCACCAAGATTAGCTTCTCCGATTCCTCCTTTGTTCGAAG
ATTCTTCAGTCTTCCATGGAGTCGAGCACTGGACAAAGGGTAAGCGATCTAAGAGATCAAGA
TCCGATTTCCACCACCAAAACCTCACTGAGGAAGAGTATCTAGCTTTTTGCCTCATGCTTCT
CGCTCGCGACAACCGTCAGCCTCCTCCTCCTCCGGCGGTGGAGAAGTTGAGCTACAAGTGTA
GCGTCTGCGACAAGACGTTCTCTTCTTACCAAGCTCTCGGTGGTCACAAGGCAAGCCACCGT
AAGAACTTATCACAGACTCTCTCCGGCGGAGGAGATGATCATTCAACCTCGTCGGCGACAAC
CACATCCGCCGTGACTACTGGAAGTGGGAAATCACACGTTTGCACCATCTGTAACAAGTCTT
TTCCTTCCGGTCAAGCTCTCGGCGGACACAAGCGGTGCCACTACGAAGGAAACAACAACATC
AACACTAGTAGCGTGTCCAACTCCGAAGGTGCGGGGTCCACTAGCCACGTTAGCAGTAGCCA
CCGTGGGTTTGACCTCAACATCCCTCCGATCCCTGAATTCTCGATGGTCAACGGAGACGACG
AAGTCATGAGCCCTATGCCGGCGAAGAAGCCTCGGTTTGACTTTCCGGTCAAACTTCAACTT
TAAGGAAATT

SEQ ID NO 2: Arabidopsis thaliana STZ protein with annotation of the domains

B-BOX L-BOX

MALEALTSPRLASPIPPLFEDSSVFHGVEHWTKG*KRSKRSR*SDFHHQNLTEEEYLAFCLMLL
ARDNRQPPPPPAVEKLSYKCSVCDKTFSSYQALGGHKASHRKNLSQTLSGGGDDHSTSSATT
TSAVTTGSGKSHVCTICNKSFPSGQALGGHKRCHYEGNNNINTSSVSNSEGAGSTSHVSSSH
RGF***DLN*I*P***PIPEFSMVNGDDEVMSPMPAKKPRFDFPVKLQL
EAR motif

SEQ ID NO 3: PRM3204 (sense, start codon in italics)
5′ GGGGACAAGTTTGTACAAAAAAGCAGGCTTCACA*ATG*GCGCTCGAGGCTC 3′

SEQ ID NO 4: PRM3205 (reverse, complementary stop codon in italics)
5′ GGGGACCACTTTGTACAAGAAAGCTGGGTAATTTCC*TTA*AAGTTGAAGTTTGA 3′

BOXES

SEQ ID NO 5: QALGGH motif
QALGGH

SEQ ID NO 6: NNM motif
NN(M/W)QMH

SEQ ID NO 7: EAR motif
hDLNh(X)P

SEQ ID NO 8: B-Box
KR(S)KRXR

SEQ ID NO 9: L-Box
EXEXXAXCLXXL

FIGURE 3

ORTHOLOGS OF STZ in OTHER PLANT SPECIES

SEQ ID NO 10: Dg_AF119050_1 Datisca glomerata zinc-finger protein 1 (zfp1) mRNA, complete cds
GGCACGAGGACAAATTCTCTCTCTATCCTCTGAATATCTTTGGTTTGTGAACTGAGAAGCTA
TTAGATGGCTCTAGAAGCGCTCAACTCTCCGACCACAGCTACGCCGGTGTTTCACTACGACG
ACCCCAGCTTGAATTACCTTGAGCCATGGACCAAGCGTAAGCGTTCCAAGCGTACGCGCTTA
GATAGCCCCATACCGAGGAAGAGTACCTTGCTTTCTGCCTCATCATGCTCGCTCGTGGCCGC
GTTGCCTCTGCAAATCGACGGGATTCTCAGTCTTCCATTCAGATTCAGCCTGAAGCAACGAC
TTCGGCTACCAAAGTCAGTTATAAGTGCTCTGTGTGCGATAAGGCCTTTTCGTCTTATCAGG
CTTTGGGTGGGCACAAGGCCAGCCACAGAAAGCTCGCTGGCGGCGAAGATCAATCGACTTCC
TTTGCCACCACGAATTCAGCCACCGTCACTACCACCACAGCCTCCGGAGGTGGTGGCAGGTC
TCATGAGTGTTCTATTTGCCACAAATCGTTCCCGACTGGCCAGGCCTTGGGTGGTCACAAGC
GCTGCCACTACGAAGGCAGTATCGGCGGCAATAGTATTCACCACCACAACAATACCACCAAC
AGCGGAAGCAACGGTGGCATGAGCATGACCTCCGAAGTAGGTTCCACACACACAGTCAGCCA
CAGTCACCGTGACTTCGATCTCAACATCCCGGCCTTGCCGGAGTTTCGGTCGAATTTCTTCA
TATCCGGGGATGACGAGGTCGAGAGTCCTCATCCGGCCAAGAAACCCCGTATATTGATGAAA
*TAA*AACATTTCTCAAGATCACTGAACCAGGCTTTAGTTTCTTTATAGGAGGAGATTTAAAAA
AGTAGTATCTCTCTTTCTTTATCCGTAGGATAATTAATATATTTCGTGTACATAAATTTGTA
GTTCTTTAACACACTCTGTTTCATTTTCTTGCTTTGCTCAACTTTGTATTGGTTATTTCATT
ATGAAAATTCAATT

SEQ ID NO 11: Dg_AF119050_1 Datisca glomerata, STZ ortholog, protein
MALEALNSPTTATPVFHYDDPSLNYLEPWTKRKRSKRTRLDSPHTEEEYLAFCLIMLARGRV
ASANRRDSQSSIQIQPEATTSATKVSYKCSVCDKAFSSYQALGGHKASHRKLAGGEDQSTSF
ATTNSATVTTTTASGGGGRSHECSICHKSFPTGQALGGHKRCHYEGSIGGNSIHHHNNTTNS
GSNGGMSMTSEVGSTHTVSHSHRDFDLNIPALPEFRSNFFISGDDEVESPHPAKKPRILMK

SEQ ID NO 12: Gm_T09602_U68763.1_GMU68763 Glycine max (soybean) probable zinc finger protein SCOF-1 mRNA, complete cds
AAAATTCTCACTCTCTCTCTCATCTCGAGATCATAGTATCATATTCAATATCATTTCATACC
AAACACATGGCTTTGGAAGCTCTCAACTCACCAACAACAACCGCTCCATCTTTTCCCTTTGA
CGACCCAACTATTCCATGGGCGAAACGAAAACGTTCAAAGCGTTCTCGCGACCATCCTTCTG
AAGAAGAGTACCTCGCCCTCTGCCTCATCATGCTCGCTCGCGGCGGCACCACCACCGTCAAC
AACCGCCACGTCAGCCCTCCGCCGCTACAGCCACAGCCACAGCCGACACCAGATCCTTCCAC
CAAGCTCAGTTACAAATGCTCCGTTTGCGACAAGAGCTTCCCCTCTTACCAAGCGCTCGGTG
GACACAAGGCCAGTCACCGGAAACTCGCCGGCGCCGCCGAAGACCAACCCCCCAGCACCACC
ACTTCCTCCGCCGCCGCCACCAGCTCCGCCTCCGGAGGTAAGGCCCATGAGTGCTCCATTTG
CCACAAATCCTTCCCCACCGGACAGGCCCTTGGCGGACACAAACGTTGTCACTACGAAGGTA
ACGGTAACGGAAATAACAACAACAGTAACAGCGTTGTCACCGTCGCCTCGGAAGGCGTGGGC
TCCACCCACACTGTCAGTCACGGCCACCACCGCGACTTCGATCTCAACATCCCGGCCTTTCC
GGATTTTTCGACCAAGGTCGGAGAAGACGAGGTTGAGAGCCCTCACCCTGTCATGAAGAAGC
CTCGCCTCTTCGTCATTCCCAAGATCGAAATCCCCCAATTTCAATGAACTCGTTGAATTTTT
AGTTTATTTTTCGACTATATATTTTGGAGAATTTTGAGAGTTACTATAATTTGATTTTGTAC
ATAGTACTTGGAAGTTTTGTTGGACCGTACCGGACCCAGTTCTCTGGTTGAGGTTGTACTTT
CACAACAGTGGCAGATTTGCAATTCAATTCAATTTATTTGTTTATTTTAAAAAAAAAAAAAA
AAAA

FIGURE 3 (continued)

SEQ ID NO 13: Gm_T09602 Glycine max (soybean) probable zinc finger protein SCOF-1, STZ otholog, protein
MALEALNSPTTTAPSFPFDDPTIPWAKRKRSKRSRDHPSEEEYLALCLIMLARGGTTTVNNR
HVSPPPLQPQPQPTPDPSTKLSYKCSVCDKSFPSYQALGGHKASHRKLAGAAEDQPPSTTTS
SAAATSSASGGKAHECSICHKSFPTGQALGGHKRCHYEGNGNGNNNNSNSVVTVASEGVGST
HTVSHGHHRDFDLNIPAFPDFSTKVGEDEVESPHPVMKKPRLFVIPKIEIPQFQ

SEQ ID NO 14: Ms_CAB77055_ Y18788.1_MSY18788 Medicago sativa putative TFIIIA (or kruppel)-like zinc finger protein mRNA
AATTCGGCACGAGAAATAACCACTTCTCTCTCAAAACCTCCTTTTGCCTTTTGCTTCTACTT
TCACTTGCGTAACGCTAACTAACTCTTCTCGAGTGTTCTTCTTTTCATCATATGGCTATGGA
AGCACTTAACTCACCCACCACTGCTACTCCTTTCACACCCTTTGAGGAACCAAATCTGAGTT
ATCTTGAAACACCGTGGACGAAAGGTAAACGATCAAAGCGTTCTCGCATGGATCAATCTTCA
TGCACTGAAGAAGAGTATCTCGCTCTTTGTCTCATCATGCTTGCTCGCAGCGGTAACAACAA
CGACAAAAAGTCTGATTCGGTGGCGACGCCGCTAACCACCGTTAAACTCAGTCACAAATGCT
CAGTCTGCAACAAAGCTTTCTCATCTTATCAAGCCCTAGGTGGACACAAAGCCAGTCACCGG
AAAGCTGTTATGTCCGCAACCACCGCTGAAGATCAGATCACCACCACTTCATCCGCCGTGAC
TACCAGCTCTGCTTCCAACGGTAAGAACAAGACTCATGAGTGTTCCATCTGTCACAAATCCT
TCCCTACTGGACAGGCTTTGGGAGGACACAAGCGTTGTCACTACGAAGGCAGCGTTGGTGCC
GGTGCCGGTGCTGGAAGTAACGCTGTAACTGCCTCTGAAGGAGTTGGATTGTCACACAGCCA
CCACCGTGATTTTGATCTTAACCTCCCGGCTTTTCCGGACTTTTCAAAGAAGTTTTTCGTGG
ATGACGAGGTTTTTAGTCCTTTACCTGCTGCAAAGAAGCCCTGTCTTTTCAAGCTGGAAATT
CCTTCTCATTACTGATCAATAATAGATCCAATTTTATTGTTATTATTATTAATAATTATTAT
CGCTTAGGGCATAGTTATTTTCTTTTTTCTTTCAATTATTTCGGATCAATTTGTTCTGTACA
TACAAATTGGGATTGGTTTTAGAATTTAGGACGGTTGTAGACAATGGAAATTCAATTCAATT
ATTTAATTTTGTGT

SEQ ID NO 15: Ms_CAB77055_Medicago sativa putative TFIIIA (or kruppel)-like zinc finger protein, STZ otholog, protein
MAMEALNSPTTATPFTPFEEPNLSYLETPWTKGKRSKRSRMDQSSCTEEEYLALCLIMLARS
GNNNDKKSDSVATPLTTVKLSHKCSVCNKAFSSYQALGGHKASHRKAVMSATTAEDQITTTS
SAVTTSSASNGKNKTHECSICHKSFPTGQALGGHKRCHYEGSVGAGAGAGSNAVTASEGVGL
SHSHHRDFDLNLPAFPDFSKKFFVDDEVFSPLPAAKKPCLFKLEIPSHY

SEQ ID NO 16: Nt_AAC06243_ AF053077 Nicotiana tabacum osmotic stress-induced zinc-finger protein (zfp) mRNA, complete cds
TTTTCCCTCGAATTTGATAACTAAAGAGAATATTATGACTCTTGAAGCTTTGAAGTCACCTA
CGGCGGCAACGCCGACTCTACCACCACGCT*ATG*AAGATGATGATGAAATTCATAATTTGGAT
TCTTGGGCTAAAGGAAAACGATCAAAACGGCCCCGTATTGATGCCCCACCGACTGAAGAAGA
GTATTTAGCCCTCTGTCTCATCATGCTCGCTCGCAGCGGAACCGGAACCAGAACCGGTTTAA
CTGATGCTACTACTTCCCAACAACCTGCCGATAAAAAAACCGCCGAGTTGCCGCCGGTTCAT
AAGAAAGAGGTGGCAACAGAGCAAGCAGAGCAATCTTACAAGTGTAGCGTGTGTGACAAGGC
TTTTTCTTCTTATCAAGCACTCGGTGGGCATAAAGCAAGTCACCGTAAAACTACTACTACTG
CTACCGCCGCCTCTGATGATAACAATCCTTCAACTTCAACTTCCACTGGCGCCGTTAATATC
TCTGCTCTTAATCCAACTGGTCGTTCACACGTCTGTTCTATTTGCCACAAGGCTTTTCCTAC
TGGCCAAGCTTTGGGTGGGCACAAGCGCCGCCACTATGAAGGCAAACTCGGTGGTAACAGCC
GCGACTTAGGCGGCGGCGGCGGCGGTCATAGTGGAAGCGTCTTGACTACTTCAGACGGC FIGURE 3 (continued)

GGCGCGTCGACTCACACGCTACGTGACTTTGACCTGAACATGCCTGCTTCGCCGGAATTGCA
ACTGGGTCTGAGTATTGATTGTGGACGGAAAAGTCAACTGTTGCCGATGGTCCAAGAGGTGG
AAAGTCCTATGCCTGCAAAGAAACCGCGTTTATTGTTTTCGTTGGGT*TGA*AACTTCTTTAGG
GGAATTGAATTGATTGTGTTTTAGCCAAATTAGTAAATTGGTTCATGTGATTTTATTTTTAG
GAAAAGGAATTATTGATTGTTTTACCCGTTTATTCTTAGGGTGGTATTATGTACAGGGAGTG
AATCATTCATTGGTTTTACACTTTCTTAATTATATATTCTTTTTTTTACACATAAAAAAAA
AAAAAAA

SEQ ID NO 17: Nt_AAC06243_Nicotiana tabacum osmotic stress-induced zinc-finger protein, STZ otholog, protein
MTLEALKSPTAATPTLPPRYEDDDEIHNLDSWAKGKRSKRPRIDAPPTEEEYLALCLIMLAR
SGTGTRTGLTDATTSQQPADKKTAELPPVHKKEVATEQAEQSYKCSVCDKAFSSYQALGGHK
ASHRKTTTTATAASDDNNPSTSTSTGAVNISALNPTGRSHVCSICHKAFPTGQALGGHKRRH
YEGKLGGNSRDLGGGGGGGHSGSVLTTSDGGASTHTLRDFDLNMPASPELQLGLSIDCGRKS
QLLPMVQEVESPMPAKKPRLLFSLG

SEQ ID NO 18: Os_AF332876 *Oryza sativa* zinc finger transcription factor ZF1 mRNA, complete cds
AATTCGGCACGAGGCCACACAGCAACCAGCCAGCTGCCACACTAGCTTGAGGCGAGCGAGCG
AAGCTTAGCTAGCGGATAGAACAAGTCGTCGATCTGCTTGCTGCTTTTGTGAATTGCGGTGG
AAGCATGTCGAGCGCGTCGTCCATGGAAGCGCTCCACGCCGCGGTGCTCAAGGAGGAGCAGC
AGCAGCACGAGGTGGAGGAGGCGACGGTCGTGACGAGCAGCAGCGCCACGAGCGGGGAGGAG
GGCGGACACCTGCCCCAGGGGTGGGCGAAGCGGAAGCGGTCGCGCCGCCAGCGATCGGAGGA
GGAGAACCTCGCGCTCTGCCTCCTCATGCTCGCCCGCGGCGGCCACCACCGCGTCCAGGCGC
CGCCTCCGCTCTCGGCTTCGGCGCCCCCGCCGGCAGGTGCGGAGTTCAAGTGCTCCGTCTGC
GGCAAGTCCTTCAGCTCCTACCAGGCGCTCGGCGGCCACAAGACGAGCCACCGGGTCAAGCT
GCCGACTCCGCCCGCAGCTCCCGTCTTGGCTCCCGCCCCCGTCGCCGCCTTGCTGCCTTCCG
CCGAGGACCGCGAGCCAGCCACGTCATCCACCGCCGCGTCCTCCGACGGCATGACCAACAGA
GTCCACAGGTGTTCCATCTGCCAGAAGGAGTTCCCCACCGGGCAGGCGCTCGGCGGGCACAA
GAGGAAGCACTACGACGGTGGCGTAGGCGCCGGCGCCGGCGCATCTTCAACCGAGCTCCTGG
CCACGGTGGCCGCCGAGTCCGAGGTGGGAAGCTCCGGCAACGGCCAGTCCGCCACCCGGGCG
TTCGACCTCAACCTCCCGGCCGTGCCGGAGTTCGTGTGGCGGCCGTGCTCCAAGGGCAAGAA
GATGTGGGACGAGGAGGAGGAGGTCCAGAGCCCCCTCGCCTTCAAGAAGCCCCGGCTTCTCA
CCGCG*TAA*TTCAGCAGCTGCACGGATCCGATCCGTCAGAGTTTTTGTCTAGGGAGTGAAATT
CAGTCGAAACACACTATTCGTTGATTCGTTTTGTGCCGCTATTGTTTAATTTGTTCCTGCTT
TTGTACAGAGCAAGCGAGTGATACATAGCCATACATACAGTCATACAGATATAGGTCTAGCT
CTTCCTTGGTTCTTTGTAACACTGGAACTGTACCTGTATCTTTTACACTTTGTTCTTTGACA
GTCATATATTGTAGACCAAAAAAAAAAAAAAAAA

SEQ ID NO 19: Os_AF332876 *Oryza sativa* seedling zinc finger transcription factor ZF1, STZ otholog, protein
MSSASSMEALHAAVLKEEQQQHEVEEATVVTSSSATSGEEGGHLPQGWAKRKRSRRQRSEEE
NLALCLLMLARGGHHRVQAPPPLSASAPPPAGAEFKCSVCGKSFSSYQALGGHKTSHRVKLP
TPPAAPVLAPAPVAALLPSAEDREPATSSTAASSDGMTNRVHRCSICQKEFPTGQALGGHKR
KHYDGGVGAGAGASSTELLATVAAESEVGSSGNGQSATRAFDLNLPAVPEFVWRPCSKGKKM
WDEEEEVQSPLAFKKPRLLTA

FIGURE 3 (continued)

SEQ ID NO 20: Ph_BAA05079_D26086.1 [Petunia x hybrida] PETZFP4 zinc-finger protein gene
TTCACTCACCAAAACAACTTCTCTACCTCTTCTACTTGCACATTCAAATTCTTTCATTACTA
CTTATCTCTACTAATCTTGATTCGATTTTAGTAAATCAAACAAGAGAATCTTTTCAGTAATA
CAAACAAGAAAATTTTCTCTCTATACTTGATTGAGTTTAGTAAGGCAAACAAGAAAACTATC
ATGGCACTTGAAGCATTGAATTCTCCAACTACAACAACACCACCATCATTCCAATTTGAGAA
CAACGGGCTTAAGTACCTTGAGAGTTGGACAAAAGGTAAAAGATCAAAAAGGCAACGCAGCA
TGGAACGACAGTGTACTGAAGAAGAGTATTTAGCACTTTGTCTTATCATGCTAGCACGTAGC
GATGGTTCTGTTAATAACTCACGGTCTCTACCACCACCACCACTACCACCATCAGTTCCAGT
AACGTCGCAAATAAACGCGACGTTATTGGAACAGAAGAATTTGTACAAGTGTTCCGTTTGTG
GTAAAGGGTTTGGGTCTTATCAAGCTTTAGGTGGACATAAAGCAAGTCACCGGAAACTTGTC
AGCATGGGAGGAGATGAACAATCTACTACTTCCACTACTACTAACGTAACGGGAACTAGTTC
CGCTAACGTTAACGGTAACGGAAGAACTCACGAATGTTCAATTTGTCACAAGTGCTTTCCTA
CTGGACAAGCTTTAGGTGGTCATAAAAGGTGCCACTATGACGGTGGTAACGGTAACGGTAAC
GGAAGTGTAAGTGTTGGGGTGACGTCATCTGAAGGTGTGGGGTCCACTATTAGTCATCACCG
TGACTTTGACTTGAATATTCCCGCGTTGCCGGAGTTTTGGCCGGGATTTGGTTCCGGCGAGG
ATGAGGTGGAGAGTCCTCATCCAGCAAAGAAGTCAAGGCTATCTCTTCCACCTAAACTTGAA
TTATTCAAAGGATTATAGAGGGAATATTGATTTGTTACAGGAAGATTTATTAGGATTCACGA
ATTTTTTGTTGACTAGTTTATGTAATAT

SEQ ID NO 21: Ph_BAA05079 [Petunia x hybrida] zinc-finger protein, STZ otholog, protein
MALEALNSPTTTTPPSFQFENNGLKYLESWTKGKRSKRQRSMERQCTEEEYLALCLIMLARS
DGSVNNSRSLPPPPLPPSVPVTSQINATLLEQKNLYKCSVCGKGFGSYQALGGHKASHRKLV
SMGGDEQSTTSTTTNVTGTSSANVNGNGRTHECSICHKCFPTGQALGGHKRCHYDGGNGNGN
GSVSVGVTSSEGVGSTISHHRDFDLNIPALPEFWPGFGSGEDEVESPHPAKKSRLSLPPKLE
LFKGL

SEQ ID NO 22: Ta_BAA03901 Triticum aestivum gene for zinc-finger protein WZF1, complete cds
ATGTCGTCGTCGGCCATGGAAGCGCTCCACGCCCTGATCCCGGAGCAGCACCAGCTGGACGT
TGAGGCGGCTGCGGCTGTCAGCAGCGCCACCAGCGGCGAGGAGAGCGGCCACGTGCTGCAGG
GGTGGGCCAAGAGGAAGCGATCGCGCCGCCAGCGCTCCGAGGAGGAGAACCTCGCGCTCTGC
CTCCTCATGCTCTCGCGCGGCGGCAAGCAGCGTGTTCAGGCGCCGCAGCCGGAGTCGTTCGC
TGCGCCGGTGCCTGCCGAGTTCAAGTGCTCCGTCTGCGGCAAGTCCTTCAGCTCCTACCAGG
CGCTCGGAGGCCACAAGACGAGCCACCGGGTGAAGCAGCCGTCTCCTCCCTCTGATGCCGCT
GCTGCCCCACTCGTGGCCCTCCCGGCCGTCGCCGCCATCCTGCCGTCCGCCGAGCCGGCCAC
GTCGTCCACCGCCGCGTCCTCCGACGGCGCGACCAACAGAGTCCACAGGTGCTCCATCTGCC
AAAAGGAGTTCCCGACTGGGCAGGCGCTCGGCGGGCACAAGAGGAAGCACTACGACGGAGGC
GTGGGCGCCGCCGCCTCGTCGACCGAGCTTCTGGCCGCCGCGGCCGCCGAGTCTGAGGTGGG
GAGCACCGGCAACGGGAGCTCCGCCGCCCGGGCCTTCGACCTGAACATTCCGGCCGTGCCGG
AGTTCGTGTGGAGGCCGTGCGCCAAGGGCAAGATGATGTGGGAGGACGATGAGGAGGTGCAG
AGCCCCCTCGCCTTCAAGAAGCCTCGGCTTCTCACCGCTTGA

FIGURE 3 (continued)

SEQ ID NO 23: Ta_BAA03901_WZF1 Triticum aestivum, STZ otholog, protein
MSSSAMEALHALIPEQHQLDVEAAAAVSSATSGEESGHVLQGWAKRKRSRRQRSEEENLALC
LLMLSRGGKQRVQAPQPESFAAPVPAEFKCSVCGKSFSSYQALGGHKTSHRVKQPSPPSDAA
AAPLVALPAVAAILPSAEPATSSTAASSDGATNRVHRCSICQKEFPTGQALGGHKRKHYDGG
VGAAASSTELLAAAAAESEVGSTGNGSSAARAFDLNIPAVPEFVWRPCAKGKMMWEDDEEVQ
SPLAFKKPRLLTA

SEQ ID NO 24: Ca AF539746 Capsicum annum zinc finger protein mRNA, complete cds
AAAATCTTCGCTACTTACTTACATCTTCTAGAATAGTCACTAGAACCAGTAACTTTATACAA
CGGATATCGAT*ATG*GCACTTGAAGCTTTGAATTCTCCAACTGGTACACCAACTCCGCCACCG
TTTCAATTTGAGAGCGACGGCCAACAGCTTCGATATATCGAAAACTGGAGGAAGGGAAAGAG
ATCTAAAAGGTCACGCAGCATGGAGCACCAGCCTACTGAGGAAGAATACTTAGCGCTTTGTT
TGATCATGCTTGCACGTAGCGGTGGCTCCGTTAATCATCAACGATCTCTACCACCGCCGGCT
CCGGTGATGAAACTGCACGCGCCGTCGTCATCATCGGCGGCGGAGGAGGAGAAGGAGAAGAT
GGTGTATAAGTGTTCGGTTTGTGGTAAGGGATTTGGGTCTTATCAAGCTTTAGGTGGACACA
AAGCTAGTCACCGGAAACTCGTACCCGGCGGAGATGATCAGTCAACTACCTCCACAACCACT
AACGCAACCGGAACAACAACCTCCGTTAACGGCAACGGCAACAGAAGTGGAAGGACTCACGA
GTGTTCGATTTGTCACAAGTGTTTTCCCACTGGACAAGCTTTAGGTGGACACAAAAGGTGTC
ACTACGACGGCGGTATCGGTAACGGAAACGCTAACAGTGGCGTTAGTGCTAGCGTTGGAGTG
ACGTCATCGGAGGGTGTGGGGTCCACAGTCAGTCACCGGGATTTCGACTTGAACATTCCGGC
GTTGCCGGAATTCTGGCTGGGATTTGGTTCCGGCGAAGATGAGGTGGAGAGTCCACATCCGG
CGAAGAAATCGCGGTTATGTTTGCCTCCAAAATATGAATTATTTCAACAT*TAA*TGGGAATTT
GATTGTTAGGATTTACTATTTTGGTAGACAAAATTATACTATGTAAGTTTTAATTTTCATTG
TGGGTGGGAGCAAAATTTTTAATTTTTTGTCTATAGACCTAGCTAGTTACTAATAGCAAAAA
TTCAATTGATTGATTTAAAAAAAAAAAAAAAAAA

SEQ ID NO 25: Ca AF539746-capsicum annum, STZ otholog, protein
MALEALNSPTGTPTPPPFQFESDGQQLRYIENWRKGKRSKRSRSMEHQPTEEEYLALCLIML
ARSGGSVNHQRSLPPPAPVMKLHAPSSSSAAEEEKEKMVYKCSVCGKGFGSYQALGGHKASH
RKLVPGGDDQSTTSTTTNATGTTTSVNGNGNRSGRTHECSICHKCFPTGQALGGHKRCHYDG
GIGNGNANSGVSASVGVTSSEGVGSTVSHRDFDLNIPALPEFWLGFGSGEDEVESPHPAKKS
RLCLPPKYELFQH

PARALOGS OF STZ IN ARABIDOPSIS THALIANA

SEQ ID NO 26: gi_18402298_ref_NM_112848.1 mRNA
ACTTCACTCTCTAATTTCCTTCTCTCTATCTCTCACCATATTCGCGATTAAAAACTCTCAAC
TTTTCTCTCAAATTTCTGATCCTTTGATCCAACAGTTAGAAGAAGATTCATCTGATCATGGC
CCTCGAAGCGATGAACACTCCAACTTCTTCTTTCACCAGAATCGAAACGAAAGAAGATTTGA
TGAACGACGCCGTTTTCATTGAGCCGTGGCTTAAACGCAAACGCTCCAAACGTCAGCGTTCT
CACAGCCCTTCTTCGTCTTCTTCCTCACCGCCTCGATCTCGACCCAAATCCCAGAATCAAGA
TCTTACGGAAGAAGAGTATCTCGCTCTTTGTCTCCTCATGCTCGCTAAAGATCAACCGTCGC
AAACGCGATTTCATCAACAGTCGCAATCGTTAACGCCGCCGCCAGAATCAAAGAACCTTCCG
TACAAGTGTAACGTCTGTGAAAAAGCGTTTCCTTCCTATCAGGCTTTAGGCGGTCACAAAGC
AAGTCACCGAATCAAACCACCAACCGTAATCTCAACAACCGCCGATGATTCAACAGCTCCGA

FIGURE 3 (continued)

CCATCTCCATCGTCGCCGGAGAAAAACATCCGATTGCTGCCTCCGGAAAGATCCACGAGTGT
TCAATCTGTCATAAAGTGTTTCCGACGGGTCAAGCTTTAGGCGGTCACAAACGTTGTCACTA
CGAAGGCAACCTCGGCGGCGGAGGAGGAGGAGGAAGCAAATCAATCAGTCACAGTGGAAGCG
TGTCGAGCACGGTATCGGAAGAAAGGAGCCACCGTGGATTCATCGATCTAAACCTACCGGCG
TTACCTGAACTCAGCCTTCATCACAATCCAATCGTCGACGAAGAGATCTTGAGTCCGTTGAC
CGGTAAAAAACCGCTTTTGTTGACCGATCACGACCAAGTCATCAAGAAAGAAGATTTATCTT
TAAAAATCTAATACTCGACTATTAATTCTTGTGTGATTTTTTTCGTTACAACCATAGTTTCA
TTTTCATTTTTTTAGTTACAAATTTTTAATTGTTCTGATTTGGATTGAATATTGGTATATTG
TTAGGGGTTGATAC

SEQ ID NO 27: Translation of gi_18402298_ref_NM_112848.1_
MALEAMNTPTSSFTRIETKEDLMNDAVFIEPWLKRKRSKRQRSHSPSSSSSSPPRSRPKSQN
QDLTEEEYLALCLLMLAKDQPSQTRFHQQSQSLTPPPESKNLPYKCNVCEKAFPSYQALGGH
KASHRIKPPTVISTTADDSTAPTISIVAGEKHPIAASGKIHECSICHKVFPTGQALGGHKRC
HYEGNLGGGGGGGSKSISHSGSVSSTVSEERSHRGFIDLNLPALPELSLHHNPIVDEEILSP
LTGKKPLLLTDHDQVIKKEDLSLKI

SEQ ID NO 28: gi_30680473_ref_NM_120516.3_mRNA
AAATCAAATCTTTTCATTTACAATTATCTTTCTTCTCAATTTAGAACTTAGTAGCTAGTCTT
CAAGATAATGGCACTTGAAACTCTTACTTCTCCAAGATTATCTTCTCCGATGCCGACTCTGT
TTCAAGATTCAGCACTAGGGTTTCATGGAAGCAAAGGCAAACGATCTAAGCGATCAAGATCT
GAATTCGACCGTCAGAGTCTCACGGAGGATGAATATATCGCTTTATGTCTCATGCTTCTTGC
TCGCGACGGAGATAGAAACCGTGACCTTGACCTGCCTTCTTCTTCGTCTTCACCTCCTCTGC
TTCCTCCTCTTCCTACTCCGATCTACAAGTGTAGCGTCTGTGACAAGGCGTTTTCGTCTTAC
CAGGCTCTTGGTGGACACAAGGCAAGTCACCGGAAAAGCTTTTCGCTTACTCAATCTGCCGG
AGGAGATGAGCTGTCGACATCGTCGGCGATAACCACGTCTGGTATATCCGGTGGCGGGGGAG
GAAGTGTGAAGTCGCACGTTTGCTCTATCTGTCATAAATCGTTCGCCACCGGTCAAGCTCTC
GGCGGCCACAAACGGTGCCACTACGAAGGAAAGAACGGAGGCGGTGTGAGTAGTAGCGTGTC
GAATTCTGAAGATGTGGGGTCTACAAGCCACGTCAGCAGTGGCCACCGTGGGTTTGACCTCA
ACATACCGCCGATACCGGAATTCTCGATGGTCAACGGAGACGAAGAGGTGATGAGTCCTATG
CCGGCGAAGAAACTCCGGTTTGACTTCCCGGAGAAACCCTAAACATAAACCTAGGAAAAACT
TTACAGAATTCATTTTATAGGAAATTGTTTTACTGTATATACAAATATCGATTTTGATTGAT
GTTCTTCTTCACTGAAAAATTATGATTCTTTGTTGTATAATTGATGTTTCTGAAAAAGATAT
AACTTTTTATTGTTTCACACGTATCAAAATTTGCTTGGATACATCA

SEQ ID NO 29: Translation of gi_30680473_ref_NM_120516.3_
MALETLTSPRLSSPMPTLFQDSALGFHGSKGKRSKRSRSEFDRQSLTEDEYIALCLMLLARD
GDRNRDLDLPSSSSSPPLLPPLPTPIYKCSVCDKAFSSYQALGGHKASHRKSFSLTQSAGGD
ELSTSSAITTSGISGGGGGSVKSHVCSICHKSFATGQALGGHKRCHYEGKNGGGVSSSVSNS
EDVGSTSHVSSGHRGFDLNIPPIPEFSMVNGDEEVMSPMPAKKLRFDFPEKP FIGURE 3 (continued)

SEQ ID NO 30: gi_30693252_ref_NM_114853.2_mRNA
ATGGCTCTCGACACTCTCAATTCTCCCACCTCCACCACCACAACCACCGCTCCTCCTCCTTT
CCTCCGTTGCCTCGACGAAACCGAGCCCGAAAACCTCGAATCATGGACCAAAAGAAAACGTA
CAAAACGTCACCGTATAGATCAACCAAACCCTCCTCCTTCTGAAGAAGAGTATCTCGCTCTT
TGCCTCCTTATGCTCGCTCGTGGCTCCTCCGATCATCACTCTCCACCGTCGGATCATCACTC
TCTTTCTCCACTGTCCGATCATCAGAAAGATTACAAGTGTTCCGTCTGTGGCAAATCTTTCC
CGTCTTACCAAGCGTTAGGTGGACACAAAACAAGTCACCGGAAACCGGTTAGTGTCGATGTT
AATAATAGTAACGGAACCGTTACTAATAACGGAAATATTAGTAACGGTTTAGTTGGTCAAAG
TGGGAAGACTCATAACTGCTCTATATGTTTTAAGTCGTTTCCCTCTGGTCAAGCATTGGGTG
GTCACAAACGTTGTCACTATGATGGTGGTAACGGTAACAGTAACGGTGACAATAGCCACAAG
TTTGACCTAAATTTACCGGCTGATCAAGTTAGTGATGAGACAATTGGAAAAAGTCAACTCTC
CGGTGAAGAAACAAAGTCGGTGTTGTGATTATTATTATTTTTACCGATCGGGATTAGCTAG
TGGTTGATCATTAGCTGAGTCTGTAATGAAAATGAT

SEQ ID NO 31: Translation of gi_30693252_ref_NM_114853.2
MALDTLNSPTSTTTTTAPPPFLRCLDETEPENLESWTKRKRTKRHRIDQPNPPPSEEEYLAL
CLLMLARGSSDHHSPPSDHHSLSPLSDHQKDYKCSVCGKSFPSYQALGGHKTSHRKPVSVDV
NNSNGTVTNNGNISNGLVGQSGKTHNCSICFKSFPSGQALGGHKRCHYDGGNGNSNGDNSHK
FDLNLPADQVSDETIGKSQLSGEETKSVL

SEQ ID NO 32: gi_30694224_ref_NM_123683.2_mRNA
AAATTTTCTATAGCAATGGCGCTTGAAGCTCTTAATTCACCAAGATTGGTCGAGGATCCCTT
AAGATTCAATGGCGTTGAGCAGTGGACCAAATGTAAGAAACGATCCAAACGTTCGAGATCTG
ATCTTCATCATAACCACCGTCTCACTGAGGAAGAGTATCTAGCTTTCTGTCTCATGCTTCTT
GCTCGGGATGGCGGCGATCTTGACTCTGTGACGGTTGCGGAGAAGCCGAGTTATAAGTGTGG
CGTTTGTTACAAGACGTTTTCGTCTTACCAAGCTCTCGGCGGTCATAAAGCGAGCCACCGGA
GCTTATACGGTGGTGGAGAGAATGATAAATCGACACCATCCACCGCCGTGAAATCTCACGTT
TGTTCGGTTTGCGGGAAATCTTTCGCCACCGGTCAAGCTCTCGGCGGCCACAAGCGGTGCCA
CTACGATGGTGGCGTTTCGAACTCGGAAGGTGTGGGGTCTACTAGCCACGTCAGCAGTAGTA
GCCACCGTGGATTTGACCTTAATATTATACCGGTGCAGGGATTTTCGCCGGACGACGAAGTG
ATGAGTCCGATGGCGACTAAGAAGCCTCGCCTGAAGTAAGTCTTTGTTGAAGACCTGGAAGT
TTATCAAATGTAAATATCAAATTTCAATTTCAAGGAACAGTTTTGTTGATTCTATTACCAAT
ACACAATACGATTCAATTCC

SEQ ID NO 33: Translation of gi_30694224_ref_NM_123683.2_
MALEALNSPRLVEDPLRFNGVEQWTKCKKRSKRSRSDLHHNHRLTEEEYLAFCLMLLARDGG
DLDSVTVAEKPSYKCGVCYKTFSSYQALGGHKASHRSLYGGGENDKSTPSTAVKSHVCSVCG
KSFATGQALGGHKRCHYDGGVSNSEGVGSTSHVSSSSHRGFDLNIIPVQGFSPDDEVMSPMA
TKKPRLK

FIGURE 3 (continued)

SEQ ID NO 34: gi_30698307_ref_NM_126145.2_mRNA
CACACTTCACTCTTTCTTCATCTTCTTCTTCTTAAATAGCTCGAAATCACATCTCACAGAAT
TAAATCTTATGGCTCTCGAGACTCTCAATTCTCCAACAGCTACCACCACCGCTCGGCCTCTT
CTCCGGTATCGTGAAGAAATGGAGCCTGAGAATCTCGAGCAATGGGCTAAAAGAAAACGAAC
AAAACGTCAACGTTTTGATCACGGTCATCAGAATCAAGAAACGAACAAGAACCTTCCTTCTG
AAGAAGAGTATCTCGCTCTTTGTCTCCTCATGCTCGCTCGTGGCTCCGCCGTACAATCTCCT
CCTCTTCCTCCTCTACCGTCACGTGCGTCACCGTCCGATCACCGAGATTACAAGTGTACGGT
CTGTGGGAAGTCCTTTTCGTCATACCAAGCCTTAGGTGGACACAAGACGAGTCACCGGAAAC
CGACGAACACTAGTATCACTTCCGGTAACCAAGAACTGTCTAATAACAGTCACAGTAACAGC
GGTTCCGTTGTTATTAACGTTACCGTGAACACTGGTAACGGTGTTAGTCAAAGCGGAAAGAT
TCACACTTGCTCAATCTGTTTCAAGTCGTTTGCGTCTGGTCAAGCCTTAGGTGGACACAAAC
GGTGTCACTATGACGGTGGCAACAACGGTAACGGTAACGGAAGTAGCAGCAACAGCGTAGAA
CTCGTCGCTGGTAGTGACGTCAGCGATGTTGATAATGAGAGATGGTCCGAAGAAAGTGCGAT
CGGTGGCCACCGTGGATTTGACCTAAACTTACCGGCTGATCAAGTCTCAGTGACGACTTCTT
AACGTTGACTGAGTTTGAGGAAAAAGTCAACTATCAAGCGAAGAAAGGGTTAGTGGACGGTG
AAGATTAACGGTCGTTTCTTTCCAGTTGCTTCGGTTTGAGCTTGACTGGGTCTGTAATGAAA
ATGATTGGAGTGGACTTGGCATTATTATTATTATTTTAAAAAGAAATGTTAATTTGTTGTT
GGATTTGTTTATAGATAGAGGAAACAATTGGGATACACAAATATTTTTTTTTTTACAAAGA
AAATAATAATGCAGAGATGGATGATTGGATCGTACACGTTATTATATAGTGGACCATTCTGT
AATCGTGAATTATTATTATTTGTTAGAAATTTAATTTTCGT

SEQ ID NO 35: Translation of gi_30698307_ref_NM_126145.2_
MALETLNSPTATTTARPLLRYREEMEPENLEQWAKRKRTKRQRFDHGHQNQETNKNLPSEEE
YLALCLLMLARGSAVQSPPLPPLPSRASPSDHRDYKCTVCGKSFSSYQALGGHKTSHRKPTN
TSITSGNQELSNNSHSNSGSVVINVTVNTGNGVSQSGKIHTCSICFKSFASGQALGGHKRCH
YDGGNNGNGNGSSSNSVELVAGSDVSDVDNERWSEESAIGGHRGFDLNLPADQVSVTTS

OTHER GENES IN EVALUATION

SEQ ID NO 36: gi_ 12698881_ref_ AF_332876.1 _mRNA, 2xC2H2, Oryza sativa
AATTCGGCACGAGGCCACACAGCAACCAGCCAGCTGCCACACTAGCTTGAGGCGAGCGAGCG
AAGCTTAGCTAGCGGATAGAACAAGTCGTCGATCTGCTTGCTGCTTTTGTGAATTGCGGTGG
AAGCATGTCGAGCGCGTCGTCCATGGAAGCGCTCCACGCCGCGGTGCTCAAGGAGGAGCAGC
AGCAGCACGAGGTGGAGGAGGCGACGGTCGTGACGAGCAGCAGCGCCACGAGCGGGGAGGAG
GGCGGACACCTGCCCCAGGGGTGGGCGAAGCGGAAGCGGTCGCGCCGCCAGCGATCGGAGGA
GGAGAACCTCGCGCTCTGCCTCCTCATGCTCGCCCGCGGCGGCCACCACCGCGTCCAGGCGC
CGCCTCCGCTCTCGGCTTCGGCGCCCCCGCCGGCAGGTGCGGAGTTCAAGTGCTCCGTCTGC
GGCAAGTCCTTCAGCTCCTACCAGGCGCTCGGCGGCCACAAGACGAGCCACCGGGTCAAGCT
GCCGACTCCGCCCGCAGCTCCCGTCTTGGCTCCCGCCCCCGTCGCCGCCTTGCTGCCTTCCG
CCGAGGACCGCGAGCCAGCCACGTCATCCACCGCCGCGTCCTCCGACGGCATGACCAACAGA
GTCCACAGGTGTTCCATCTGCCAGAAGGAGTTCCCCACCGGGCAGGCGCTCGGCGGGCACAA
GAGGAAGCACTACGACGGTGGCGTAGGCGCCGGCGCCGGCGCATCTTCAACCGAGCTCCTGG
CCACGGTGGCCGCCGAGTCCGAGGTGGGAAGCTCCGGCAACGGCCAGTCCGCCACCCGGGCG
TTCGACCTCAACCTCCCGGCCGTGCCGGAGTTCGTGTGGCGGCCGTGCTCCAAGGGCAAGAA
GATGTGGGACGAGGAGGAGGAGGTCCAGAGCCCCCTCGCCTTCAAGAAGCCCCGGCTTCTCA
CCGCGTAATTCAGCAGCTGCACGGATCCGATCCGTCAGAGTTTTTGTCTAGGGAGTGAAATT
CAGTCGAAACACACTATTCGTTGATTCGTTTTGTGCCGCTATTGTTTAATTTGTTCCTGCTT

FIGURE 3 (continued)

TTGTACAGAGCAAGCGAGTGATACATAGCCATACATACAGTCATACAGATATAGGTCTAGCT
CTTCCTTGGTTCTTTGTAACACTGGAACTGTACCTGTATCTTTTACACTTTGTTCTTTGACA
GTCATATATTGTAGACCAAAAAAAAAAAAAAAAA

SEQ ID NO 37: gi_12698882_ref_AAK01713.1, 2xC2H2, Oryza sativa
MSSASSMEALHAAVLKEEQQQHEVEEATVVTSSSATSGEEGGHLPQGWAKRKRSRRQRSEEE
NLALCLLMLARGGHHRVQAPPPLSASAPPPAGAEFKCSVCGKSFSSYQALGGHKTSHRVKLP
TPPAAPVLAPAPVAALLPSAEDREPATSSTAASSDGMTNRVHRCSICQKEFPTGQALGGHKR
KHYDGGVGAGAGASSTELLATVAAESEVGSSGNGQSATRAFDLNLPAVPEFVWRPCSKGKKM
WDEEEEVQSPLAFKKPRLLTA

SEQ ID NO 38: gi_6434215_ref_AL132966.1_region 116202 ... 116729, 2xC2H2, Arabidopsis thaliana ATGAAGAGAGACCGGTCCGATTACGAAGAATCCATGAAGCATATAGACATAGTAGAAAGTCT
AATGATGTTATCTCGAAGTTTCGTGGTCAAACAAATCGATGTAAAGCAATCTACCGGAAGCA
AAACGAACCATAATAACCACTTCGAATGCAAAACGTGTAACCGGAAATTTGATTCCTTCCAA
GCTCTTGGAGGTCATAGAGCTAGCCACAAGAAACCTAAGCTGATCGTTGACCAAGAACAGGT
GAAGCATCGTAACAAAGAGAATGATATGCATAAGTGTACAATTTGCGATCAAATGTTTGGGA
CCGGTCAAGCTCTAGGCGGTCACATGAGAAAGCATAGGACGAGCATGATAACCGAGCAATCG
ATTGTCCCTTCTGTGGTTTATTCCAGACCGGTTTTTAATCGTTGCAGTAGCAGCAAGGAGAT
CTTGGACTTAAATCTAACTCCATTGGAAAATGATCTTGTGTTAATCTTTGGGAAGAATTTGG
TTCCACAAATTGATTTGAAGTTTGTGAATTAG

SEQ ID NO 39: gi_6729511_ref_CAB67667.1, 2xC2H2, Arabidopsis thaliana
MKRDRSDYEESMKHIDIVESLMMLSRSFVVKQIDVKQSTGSKTNHNNHFECKTCNRKFDSFQ
ALGGHRASHKKPKLIVDQEQVKHRNKENDMHKCTICDQMFGTGQALGGHMRKHRTSMITEQS
IVPSVVYSRPVFNRCSSSKEILDLNLTPLENDLVLIFGKNLVPQIDLKFVN

SEQ ID NO 40: ref_CA279020, 2xC2H2, sugar cane
CCTAACCAGCATTAGCTTTTCAAATCAACAAGCCTCGCCGTGACCGATCGATGGCCATCACC
CACGACGACTACGTCTCCCTCTGCCTCATGGCGCTCGCAGCCGCGGGAGGCGGAGGCCAAGC
TGGTTTAACAACGCAGTACGCTCTGAACACGGCTGCCTGGACAGCGACGGCGCAAGAGTCCG
AGCTCCGCTTCCGGTGCTCCGTCTGTGGCAAGGCCTTCGCGTCGCACCAGGCACTGGGCGGG
CACAAGGCCAGCCACCGCAAGCCGACGCTCGTACAGGCACATGCGTCGTCCTCAGCCGGAGG
CGCGGCGTCGTCGTCGGTAACAATGACCTCGGCCGTAGGCAGCAGTGGGCAGGGGAGGCACA
GGTGCACGGTGTGCCATCGGAGCTTCGCGACGGNGCAAGCGCTCGGCGGGCACAAGAGGTGC
CATTACTGGGACGGGCTCTCGGTGTCGCTCACCGCGTCGTCGGCGCCATCGGGGTCCGGGTC
GACCGTCAAGGGCTTTGATCTGAATTTGGTGCCGGTGCCGCCCGCGATGGCCGCCAACGCTG
CGACAAGGTGGGGAGAGGAGAANNAAGTCANAAACCCTTGGCGGTCAAGAGAAGGCGGCTTG
CCGGTCCGTCTTGGACCCTAATTTAACGATTTAGAAGTCCTTTTTTTAATAATTAAGAGTTC
TTTTGAAGAAGGTTGTAAAGTTTTCGAACCTTGTTCTTTTAATGGATTTGGGTGCTGGCGAA
ATTTTAAAACTGGATTTAAATTTGCGCTCACTCTTTTTTTTATTTTTTACACCCTTTTTTT
TTTTTAGAAGAAGA

FIGURE 3 (continued)

SEQ ID NO 41: gi_18027011_ref_AF254447.1, 2xC2H2, Arabidopsis thaliana
TTCCTTTCTCTTCCTCTCTCTCTCTCTTCACCATGACTGATCCTTATTCCAATTTCTTCACA
GACTGGTTCAAGTCTAATCCTTTTCACCATTACCCTAATTCCTCCACTAACCCCTCTCCTCA
TCCTCTTCCTCCTGTTACTCCTCCCTCTTCCTTCTTCTTCTTCCCTCAATCCGGAGACCTCC
GCCGTCCACCGCCGCCACCAACTCCTCCTCCTTCTCCTCCTCTCCGAGAAGCCCTCCCTCTC
CTCAGCCTCAGCCCCGCCAACAAACAACAAGACCACCATCACAACCATGACCACCTTATTCA
AGAACCACCTTCAACCTCCATGGATGTCGACTACGATCATCACCATCAAGATGATCATCATA
ACCTCGATGACGATGACCATGACGTCACCGTTGCTCTTCACATAGGCCTTCCAAGCCCTAGT
GCTCAAGAGATGGCCTCTTTGCTCATGATGTCTTCTTCTTCCTCTTCCTCGAGGACCACTCA
TCATCACGAGGACATGAATCACAAGAAAGACCTCGACCATGAGTACAGCCACGGAGCTGTCG
GAGGAGGAGAAGATGACGATGAAGATTCAGTCGGCGGAGACGGCGGCTGTAGAATCAGCAGA
CTCAACAAGGGTCAATATTGGATCCCTACACCTTCTCAGATTCTCATTGGCCCTACTCAGTT
CTCATGTCCTGTTTGCTTCAAAACCTTCAACAGATACAATAACATGCAGATGCATATGTGGG
GACATGGATCACAATACAGAAAAGGACCTGAATCTCTAAGGGGAACACAACCAACAGGAATG
CTAAGGCTTCCGTGCTATTGCTGCGCCCCAGGCTGTCGCAACAACATTGACCATCCAAGGGC
AAAGCCTCTCAAAGACTTCAGAACCCTTCAAACACATTACAAGAGAAAACATGGGATCAAAC
CTTTCATGTGTAGGAAATGTGGAAAGGCTTTCGCAGTCCGAGGGGACTGGAGAACACATGAG
AAGAATTGTGGCAAACTTTGGTATTGCATATGTGGATCTGATTTCAAGCACAAGAGATCTCT
CAAAGATCACATCAAGGCTTTTGGGAATGGTCATGGAGCCTACGGAATTGATGGGTTTGATG
AAGAAGATGAGCCTGCCTCTGAGGTAGAACAATTAGACAATGATCATGAGTCAATGCAGTCT
AAATAGCTTATATATATTACTATAAGTACTAAGTAATTCGGTATATATATTAATTATAAGAA
ACCTAAATCTATGGACCAAGTTTTGATGGAGGTAGGGCTTTTCAAACTAAAAGCTATATCAT
CTAATTGATCATAGGAAAAAAATGAATCAAGAGCACTTGGAAAATTTTAAATTGTATCTTTA
GCTTCCTAGTTAAATTTATTGCAAGACAATGTAGCAGTCTAACCAATGAGGTTCCCAACGGT
TTATTTCTATTTGTATATTATTTTGTCATTAGCTTCACCTTTCGTTAATTCGAAGGACATAA
CTTATAAATGTTTAAATTATG

SEQ ID NO 42: At3g57670, 2xC2H2, Arabidopsis thaliana
MTDPYSNFFTDWFKSNPFHHYPNSSTNPSPHPLPPVTPPSSFFFFPQSGDLRRPPPPPTPPP
SPPLREALPLLSLSPANKQQDHHHNHDHLIQEPPSTSMDVDYDHHHQDDHHNLDDDDHDVTV
ALHIGLPSPSAQEMASLLMMSSSSSSRTTHHHEDMNHKKDLDHEYSHGAVGGGEDDDEDSV
GGDGGCRISRLNKGQYWIPTPSQILIGPTQFSCPVCFKTFNRYNNMQMHMWGHGSQYRKGPE
SLRGTQPTGMLRLPCYCCAPGCRNNIDHPRAKPLKDFRTLQTHYKRKHGIKPFMCRKCGKAF
AVRGDWRTHEKNCGKLWYCICGSDFKHKRSLKDHIKAFGNGHGAYGIDGFDEEDEPASEVEQ
LDNDHESMQSK

SEQ ID NO 43: gi_18676370_ref_AJ311810.2, 2xC2H2, Arabidopsis thaliana
ATCTACACACTACTACTCACATCTCATCTCTCTCTAGCACATACCCATCAAACCATATAGAT
ACGGTGCTTTTATTCTTGATCTTCTTCTTCTTCTTTGTCTTCTCCTCAGAGTCATGTCTAAT
CCAGCTTGTTCGAATCTCTTCAACAATGGATGTGACCATAATAGCTTCAACTATTCCACTTC
TCTCTCTTACATTTACAACTCTCACGGTAGCTACTATTACTCTAATACCACAAACCCTAATT
ACATTAATCATACTCATACCACTTCCACTTCCCCTAACTCACCCCCACTAAGAGAAGCTCTT
CCTCTTCTTAGCTTAAGCCCCATAAGGCACCAAGAACAACAAGACCAACACTATTTCATGGA
CACCCATCAAATTAGCTCTTCAAACTTTCTTGATGATCCTCTTGTGACTGTGGATCTTCATC
TAGGGTTACCAAACTACGGTGTTGGTGAGAGCATTAGGAGCAATATTGCTCCTGATGCAACC

FIGURE 3 (continued)

ACGGACGAGCAAGATCAAGATCATGACCGAGGAGTAGAAGTCACAGTTGAGTCCCACCTTGA
TGATGATGATGATCATCATGGAGATCTACACAGAGGTCATCACTATTGGATTCCTACTCCTT
CTCAGATTTTGATTGGTCCTACACAGTTCACTTGTCCTCTTTGCTTCAAGACATTCAACAGA
TACAACAACATGCAGATGCACATGTGGGGACACGGCTCACAATACAGAAAGGGACCAGAATC
CTTAAGAGGAACCCAACCAACAGGAATGCTAAGACTACCATGTTTCTGCTGTGCACCCGGTT
GCAAGAACAACATTGACCACCCACGAGCCAAGCCTCTTAAGGACTTTCGAACCCTCCAAACA
CATTACAAACGTAAACATGGGTCTAAACCATTTGCTTGTCGTATGTGTGGTAAGGCCTTTGC
AGTGAAAGGAGATTGGAGAACGCATGAGAAGAATTGTGGAAAGCTTTGGTATTGCTCTTGTG
GCTCGGATTTTAAGCACAAGAGGTCGCTTAAGGACCATGTCAAGGCCTTTGGAAATGGTCAT
GTTCCTTGTGGGATTGATAGTTTTGGAGGAGATCATGAGGACTACTATGATGCTGCTTCTGA
TATCGAGCAATAAGATGATAGCAACAACAATGAGTGTTAATTAGGGGTTTTGTTTATTTTTC
CTCTCATGCATTAGTTGATTGTATGCACGTGTTCTTTAGTTTTGTTCTTCGGATCTTTGTTT
TATTTTGTTTTGAGCTGTTTTTTTTTAATTACTAAGAAGTTAATTATCATCTAAAGATTTT
C

SEQ ID NO 44: gi_18376498_ref_CAC86167.1, 2xC2H2, Arabidopsis thaliana
MSNPACSNLFNNGCDHNSFNYSTSLSYIYNSHGSYYYSNTTNPNYINHTHTTSTSPNSPPLR
EALPLLSLSPIRHQEQQDQHYFMDTHQISSSNFLDDPLVTVDLHLGLPNYGVGESIRSNIAP
DATTDEQDQDHDRGVEVTVESHLDDDDDHHGDLHRGHHYWIPTPSQILIGPTQFTCPLCFKT
FNRYNNMQMHMWGHGSQYRKGPESLRGTQPTGMLRLPCFCCAPGCKNNIDHPRAKPLKDFRT
LQTHYKRKHGSKPFACRMCGKAFAVKGDWRTHEKNCGKLWYCSCGSDFKHKRSLKDHVKAFG
NGHVPCGIDSFGGDHEDYYDAASDIEQ

SEQ ID NO 45: gi_7798991_ref_AL355775.1_region 7957 ... 8451, 2xC2H2, Arabidopsis thaliana
ATGGTTGCGAGAAGTGAGGAAGTTGAGATAGTGGAAGATACGGCGGCGAAATGTTTGATGTT
GTTATCAAGAGTTGGAGAATGCGGCGGAGGAGGAGAGAAACGAGTTTTCCGATGCAAGACTT
GTCTTAAAGAGTTTTCGTCGTTTCAAGCTTTGGGAGGTCATCGTGCAAGCCACAAGAAACTC
ATTAACAGTAGCGATCCATCACTTCTTGGATCCTTGTCTAACAAGAAAACTAAAACGGCGAC
GTCTCATCCTTGTCCGATATGTGGCGTGGAGTTTCCGATGGGGCAAGCTCTTGGTGGTCACA
TGAGGAGACATAGGAGTGAGAAAGCCTCACCAGGCACGTTGGTTACACGTTCTTTTTTACCG
GAGACGACGACGGTGACGACTTTGAAAAAATCGAGTAGTGGGAAGAGAGTGGCTTGTTTGGA
CTTAGATTCGATGGAGAGTTTAGTCAATTGGAAGTTGGAGTTGGGAAGAACGATTTCTTGA

SEQ ID NO 46: gi_7798996_ref_CAB90935.1, 2xC2H2, Arabidopsis thaliana
MVARSEEVEIVEDTAAKCLMLLSRVGECGGGGEKRVFRCKTCLKEFSSFQALGGHRASHKKL
INSSDPSLLGSLSNKKTKTATSHPCPICGVEFPMGQALGGHMRRHRSEKASPGTLVTRSFLP
ETTTVTTLKKSSSGKRVACLDLDSMESLVNWKLELGRTIS

SEQ ID NO 47: gi_9755794_ref_AL391143.1_region 31730 ... 32938, 2xC2H2, Arabidopsis thaliana
ATGGAAGACGAACATCAAGATCTCCATAAACCCATTAATGGAGCTTTGCGAGACCTCAAGAT
TACTCGGTCACAGAAAGAAACAGAAAAGTCTACGAACCAACAGCAAGATGTTACTTGTTACT
ATGGTCTAAGGGAAAACTCGAAGAAGAAAACCCAGGAATCTCCGGAACCAATGAAGAAGATT
TTGTTTCGATGCGAAGAATGTGGAAAAGGGTTTCGGTACGAGAAATATTTTAAGAATCATCG FIGURE 3 (continued)

CTCGATGATGCATTTATCGCCGAACGAGAAGGTTTGTGAAGAATCCTTGATGACTCTGTCTC
GTAGCCTTGGGTTTGTGAAGAAGAAGAAAAGATCAAGACTTGGTAGGTCTGGGAAGACTTTA
TTTACTACGTTTCTTGAACCGAGTTCTATTTTTGATGCGACTGATGAAGAATTAGAAGTGGC
GGATTGTTTGATTCTATTGTCTAAGAGTGCTCCCAAGGTTGTAGACGAATTGAAAAGTCTTT
CTGAGGCAGTACGTGTTACTCCTGAAACACCTGAAAGTAGCTATGATTTGGGTTGTTTGCTC
AACAAGAAACCGAGAAAAGGTGGTGAATTGGAATCTGGGGTTTTAAGTAATGAGCAAAGACT
TATGGAAGAAGGGTTTAGTAGTTATGGAACATCGAAAGAACCAGCTAGCTTCTTGAGAGACG
AAAACAGATTGGATCAGCAGAAACGGAGAAAAGATGGTGAATTTGAATCCGGACTTTTGAGT
AATGAGCAAAGACTGCTAGAAGAAGAGATTACTACTCCTGTGACATTCAAAGGTCCAGCGAG
TTCCTTGAGACACAAGTGTGCTTTGGATCGAAATGGAGGTGAATTTGGTCCTGAGTTTTTGA
GTAATGAGCAAACACTGATGGAAGAAACATGGAAAGAACCAGTGAGTTTCTTAGAAGATAAG
CATGAATTTGATCAGCGGAAAATGCGAGAAGCTGGCGACTTTGAATCTAGGTTTTACAGAAT
TGAGCTTGGAGTAGGAGCTATGGAGTGTACTTCTTCAGATACTGATATGCTCACGCAATCTG
ATAAGAAGAACGTTGAGCATCGATGCAGGTTGTGCAACAAGATATTCTCGTCTTATCAAGCT
CTAGGGGGTCATCAGACGTTTCATCGGATGAGCAAATGTAAGAACAAGAAGAATGGCATAGA
GGAATCAGTTGAACCCAGGATGACTCTGTGA

SEQ ID NO 48: gi_9755803_ref_CAC01747.1, 2xC2H2, Arabidopsis thaliana

MEDEHQDLHKPINGALRDLKITRSQKETEKSTNQQQDVTCYYGLRENSKKKTQESPEPMKKI
LFRCEECGKGFRYEKYFKNHRSMMHLSPNEKVCEESLMTLSRSLGFVKKKKRSRLGRSGKTL
FTTFLEPSSIFDATDEELEVADCLILLSKSAPKVVDELKSLSEAVRVTPETPESSYDLGCLL
NKKPRKGGELESGVLSNEQRLMEEGFSSYGTSKEPASFLRDENRLDQQKRRKDGEFESGLLS
NEQRLLEEEITTPVTFKGPASSLRHKCALDRNGGEFGPEFLSNEQTLMEETWKEPVSFLEDK
HEFDQRKMREAGDFESRFYRIELGVGAMECTSSDTDMLTQSDKKNVEHRCRLCNKIFSSYQA
LGGHQTFHRMSKCKNKKNGIEESVEPRMTL

SEQ ID NO 49: gi_1418338_ref_X98678.1, 2xC2H2, Arabidopsis thaliana

CTTGTTAGTTCACTCCACATAATAAACACCAAAGATTTCATTCTCTTCTCCATAATTTCGAA
GTTTCTTGAATTGGGTTTGTTTCTTGATTTGTTTCTTGAATTGGGTTTTGGTCTTCTTTTCT
TACTATATTTGGATATGATGATGGGTCAAGATGAGGTTGGGAGTGATCAGACGCAAATCATA
AAAGGGAAACGTACGAAGCGACAAAGATCGTCTTCGACGTTTGTGGTGACGGCGGCGACAAC
AGTGACTTCAACAAGTTCATCGGCCGGTGGAAGTGGAGGAGAAAGAGCTGTTTCAGATGAAT
ACAACTCGGCGGTTTCGTCTCCGGTGACTACTGATTGTACGCAAGAAGAAGAAGACATGGCG
ATTTGTCTCATCATGTTAGCTCGTGGGACAGTTCTTCCATCGCCGGATCTCAAGAACTCGAG
AAAAATTCATCAGAAGATTTCGTCGGAGAATTCTAGTTTCTATGTGTACGAGTGTAAAACGT
GTAACCGGACGTTTTCGTCGTTCCAAGCACTTGGTGGACACAGAGCGAGCCACAAGAAGCCG
AGGACGTCGACTGAGGAAAAGACTAGACTACCCCTGACGCAACCCAAGTCTAGTGCATCAGA
AGAAGGGCAAAACAGTCATTTCAAAGTTTCCGGCTCAGCCCTAGCTTCACAGGCAAGTAACA
TCATCAACAAGGCAAACAAAGTACACGAGTGTTCCATCTGCGGTTCTGAGTTCACTTCCGGG
CAAGCTCTCGGTGGTCACATGAGGCGGCACAGGACAGCCGTAACCACGATTAGCCCCGTTGC
AGCCACCGCAGAAGTAAGCAGAAACAGTACAGAGGAAGAGATTGAGATCAATATAGGCCGTT
CGATGGAACAGCAGAGGAAATATCTACCGTTGGATCTTAATCTACCAGCACCAGGAGATGAT
CTAAGAGAGTCCAAGTTTCAAGGGATAGTATTCTCAGCAACACCAGCGTTAATAGATTGTCA
TTACTAGTTGTTTTTTTTACTACATAATATGATGAAATATTTGTGAATTCTTCTTACTTACT
ACTATATTGTTGATCAAAAAAAAAAAAAAAAAA

FIGURE 3 (continued)

SEQ ID NO 50: gi_1418339_ref_CAA67236.1, 2xC2H2, Arabidopsis thaliana

MGQDEVGSDQTQIIKGKRTKRQRSSSTFVVTAATTVTSTSSSAGGSGGERAVSDEYNSAVSS
PVTTDCTQEEEDMAICLIMLARGTVLPSPDLKNSRKIHQKISSENSSFYVYECKTCNRTFSS
FQALGGHRASHKKPRTSTEEKTRLPLTQPKSSASEEGQNSHFKVSGSALASQASNIINKANK
VHECSICGSEFTSGQALGGHMRRHRTAVTTISPVAATAEVSRNSTEEEIEINIGRSMEQQRK
YLPLDLNLPAPGDDLRESKFQGIVFSATPALIDCHY

FIGURE 3 (continued)

PLANTS HAVING MODIFIED GROWTH CHARACTERISTICS AND A METHOD FOR MAKING THE SAME

This application is the US national phase of international application PCT/EP2003/051104 filed 24 Dec. 2003, which designated the U.S. and claims priority of EP 02080654.3, filed 24 Dec. 2002, the entire contents of each of which are hereby incorporated by reference.

The present invention concerns a method for modifying plant growth characteristics. More specifically, the present invention concerns a method for modifying the growth characteristics of a plant by modifying expression of a nucleic acid encoding a zinc finger protein and/or by modifying the level and/or activity of a zinc finger protein in a plant, which zinc finger protein has two zinc finger domains of the type C2H2 (2×C2H2). The present invention also concerns plants having modified expression of a nucleic acid encoding a 2×C2H2 zinc finger protein and/or modified levels and/or activity of a 2×C2H2 zinc finger protein, which plants have modified growth characteristics relative to corresponding wild type plants.

Given the ever-increasing world population, it remains a major goal of agricultural research to improve the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants in a specific and controlled way. Genetic engineering of plants entails the isolation and manipulation of genetic material (typically in the form of DNA or RNA) and the subsequent introduction of that genetic material into a plant. Such technology has led to the development of plants having various improved economic, agronomic or horticultural traits. A trait or growth characteristic of particular economic interest is high yield. Yield is normally defined as the measurable produce of economic value from a crop. This may be defined in terms of quantity and/or quality. Other important growth characteristics include modified architecture, modified growth rate, among others.

The ability to influence one or more of the abovementioned growth characteristics, would have many applications in areas such as crop enhancement, plant breeding, production of ornamental plants, arboriculture, horticulture, forestry, production of algae or plants (for example for use as bioreactors, for the production of substances such as pharmaceuticals, antibodies, or vaccines, or for the bioconversion of organic waste or for use as fuel in the case of high-yielding algae and plants).

The term "zinc finger" describes a nucleic acid-binding domain in a protein that is folded around a tetrahedrally coordinated zinc ion (Miller et al. 1985. EMBO, 4, 1609-1614). The amino acids that coordinate the zinc ion, are always cystein or histidine residues, however, diversity occurs in the sequence and length of the zinc finger domain. Zinc finger proteins may contain several zinc finger domains of the same or different type. Further variability is encountered in nature by association of zinc finger domains with other domains. For example, some zinc finger proteins are found in association with ring finger or coil-coil domains, to form a so-called tripartite domain. There are several types of zinc fingers, such as C2H2, C2HC, C2C2. C2H2 is known as the classical zinc finger domain. There are typically two criteria used to classify zinc finger proteins, the first being the type of zinc finger and the second being the number of zinc fingers present in the protein. Zinc finger proteins having a single C2H2 domain have been characterised, for example Superman from *Arabidopsis* and Ramosa I from maize. A well-characterised zinc finger protein having three C2H2 domains is the Indeterminate 1 protein from Maize. Although the first report of this gene (Colasanti et al., Cell. 1998 May 15; 93(4):593-603) only mentions the presence of two zinc finger domains, a more sophisticated analysis, using pFAM domain search, revealed the presence of three C2H2 zinc finger domains. Also known are zinc-finger proteins having only two C2H2 domains, for example ZAT10 (STZ) and SCOF-1. This subset of plant zinc finger proteins having two C2H2 domains have been implicated in plant responses to various stresses (Sakamoto et al., Gene 248 (1-2) 23-32 (2000)). Both STZ and SCOF-1 have been used to enhance abiotic stress tolerance. When over-expressed, STZ has been reported to increase salt tolerance in yeast (Lippuner et al., J Biol. Chem. 271 (22) 12859-12866 (1996)) and over-expression of the SCOF-1 gene under control of the CaMV 35 S promoter has been reported to enhance cold tolerance in *Arabidopsis thaliana* (Kim et al., Plant J. 25 (3)247-259 (2001)). Reports of plants having modified expression of a zinc finger encoding gene (whether the zinc finger gene is mutated, over-expressed or otherwise) describe plants having abnormal growth characteristics, none of which (with the exception of cold stress tolerance in transgenic plants expressing SCOF-1) are desirable for crops or describe effects that are only detectable under particular stress conditions.

It has now been found that modifying expression in a plant of a 2×C2H2 zinc finger gene and/or modifying the level and/or activity in a plant of a 2×C2H2 zinc finger protein gives plants having modified growth characteristics. In particular it has been found that introduction into a plant of a 2×C2H2 zinc finger nucleic acid gives plants modified growth characteristics, such as increased yield, modified leaf architecture and altered cycle time, each relative to wild type plants.

Therefore according to one embodiment of the present invention there is provided a method for modifying the growth characteristics of a plant, comprising modifying expression In a plant of a nucleic acid encoding a 2×C2H2 zinc finger protein and/or modifying level and/or activity in a plant of a 2×C2H2 zinc finger protein.

The term "modifying" as used herein is taken to mean enhancing, decreasing and/or changing in place and/or time. Modifying expression of a nucleic acid encoding a 2×C2H2 zinc finger protein or modifying the level and/or activity of the 2×C2H2 zinc finger protein itself encompasses altered expression of a gene and/or altered level and/or activity of a gene product, namely a polypeptide, in specific cells or tissues, when compared to expression, level and/or activity of a 2×C2H2 zinc finger gene or protein In corresponding wild-type plants. The modified gene expression may result from modified expression of an endogenous 2×C2H2 zinc finger gene and/or may result from modified expression of a 2×C2H2 zinc finger gene previously introduced into a plant. Similarly, modified levels and/or activity of a 2×C2H2 zinc finger protein may be due to modified expression of an endogenous 2×C2H2 zinc finger nucleic acid/gene and/or due to modified expression of a 2×C2H2 zinc finger nucleic acid/gene previously introduced into a plant. Modified expression of a gene/nucleic acid and/or modified level and/or activity of a gene product/protein may be effected, for example, by chemical means and/or recombinant means.

Therefore there is provided by the present invention, a method for modifying the growth characteristics of a plant, comprising modifying expression, level and/or activity of a 2×C2H2 zinc finger gene or protein by recombinant means and/or by chemical means.

Advantageously, modifying expression of a nucleic acid encoding a 2×C2H2 zinc finger protein and/or modifying level and/or activity of the 2×C2H2 zinc finger protein itself may be effected by chemical means, i.e. by exogenous application of one or more compounds or elements capable of modifying activity of the 2×C2H2 zinc finger protein and/or capable of modifying expression of a 2×C2H2 zinc finger gene (which may be either an endogenous gene or a transgene introduced into a plant). The term "exogenous application" as defined herein is taken to mean the contacting or administering of a suitable compound or element to a plant The compound or element may be exogenously applied to a plant in a form suitable for plant uptake (such as through application to the soil for uptake via the roots, or in the case of some plants by applying directly to the leaves, for example by spraying). The exogenous application may take place on wild-type plants or on transgenic plants that have previously been transformed with a 2×C2H2 zinc finger nucleic acid/gene or other transgene.

Suitable compounds or elements for exogenous application Include 2×C2H2 zinc finger proteins or 2×C2H2 zinc finger nucleic adds. Alternatively, exogenous application of compounds or elements capable of modifying levels of factors that directly or indirectly activate or inactivate a 2×C2H2 zinc finger protein will also be suitable in practising the invention. Also included are antibodies that can recognise or mimic the function of 2×C2H2 zinc finger proteins. Such antibodies may comprise "plantibodies", single chain antibodies, IgG antibodies and heavy chain camel antibodies, as well as fragments thereof.

Additionally or alternatively, the resultant effect may also be achieved by the exogenous application of an interacting protein or activator or an inhibitor of a 2×C2H2 zinc finger gene/gene product. Additionally or alternatively, the compound or element may be a mutagenic substance, such as a chemical selected from any one or more of: N-nitroso-N-ethylurea, ethylene imine, ethyl methanesulphonate and diethyl sulphate. Mutagenesis may also be achieved by exposure to ionising radiation, such as X-rays or gamma-rays or ultraviolet light. Methods for introducing mutations and for testing the effect of mutations (such as by monitoring gene expression and/or protein activity) are well known in the art.

Additionally or alternatively, and according to a preferred embodiment of the present invention, modifying expression of a nucleic add encoding a 2×C2H2 zinc finger protein and/or modifying level and/or activity of the 2×C2H2 zinc finger protein may be effected by recombinant means. Such recombinant means may comprise a direct and/or indirect approach for modifying expression of a nucleic acid and/or level and/or activity of a protein.

For example, an indirect approach may comprise introducing, into a plant, a nucleic acid capable of modifying expression of the gene In question (a gene encoding a 2×C2H2 zinc finger protein) and or capable of modifying the level and/or activity of the protein In question (a 2×C2H2 zinc finger protein). Examples of such nucleic acids to be Introduced Into a plant include nucleic acids encoding transcription factors or activators or inhibitors that bind to the promoter of a 2×C2H2 zinc finger gene or that interact with a 2×C2H2 zinc finger protein. Methods to test these types of interactions and methods for isolating nucleic acids encoding such interactors include yeast one-hybrid or yeast two-hybrid screens in which the 2×C2H2 zinc finger gene/protein is used as bait. One example of such a transcription regulator Is LOS2, described as a transcription regulator for the STZ gene. Therefore, the method of the invention may also be performed using LOS2, wherein expression of a 2×C2H2 zinc finger gene may be increased or further increased by decreasing expression of LOS2 In plants.

Also encompassed by an indirect approach for modifying expression of a 2×C2H2 zinc finger gene and/or for modifying level and/or activity of a 2×C2H2 zinc finger protein is the provision of, or the inhibition or stimulation of regulatory sequences that drive expression of a native 2×C2H2 zinc finger gene or transgene. Such regulatory sequences may be introduced into a plant. For example, the regulatory sequence to be introduced into a plant may be a promoter capable of driving expression of an endogenous 2×C2H2 zinc finger gene.

A further indirect approach for modifying expression of a 2×C2H2 zinc finger gene and/or for modifying level and/or activity of a 2×C2H2 zinc finger protein In a plant encompasses modifying levels in a plant of a factor capable of interacting with a zinc finger protein. Such factors may include ligands of a 2×C2H2 zinc finger protein. Therefore, the present invention also provides a method for modifying growth characteristics of a plant, comprising modifying expression of a gene coding for a protein which is a natural ligand of a 2×C2H2 zinc finger protein. Furthermore, the present invention also provides a method for modifying growth characteristics of a plant, comprising modifying expression of a gene coding for a protein which is a natural target/substrate of a 2×C2H2 zinc finger protein. Examples of such targets/substrates include stretches of DNA that are bound by the zinc finger domains.

A direct and preferred approach on the other hand comprises introducing into a plant a nucleic acid encoding a 2×C2H2 zinc finger protein or a portion thereof or sequences capable of hybridising therewith, which nucleic acid preferably encodes a 2×C2H2 zinc finger protein or a homologue, derivative or active fragment thereof. The nucleic acid may be introduced into a plant by, for example, transformation.

Therefore, there is provided a method for modifying growth characteristics of a plant, comprising introducing Into a plant a 2×C2H2 zinc finger nucleic acid or a portion thereof.

The 2×C2H2 zinc finger nucleic acid may be derived (either directly or indirectly (if subsequently modified)) from any source provided that the sequence, when expressed in a plant, leads to modified expression of a 2×C2H2 zinc finger-encoding nucleic acid/gene and/or modified level and/or activity of a 2×C2H2 zinc finger protein. The 2×C2H2 zinc finger gene or protein may be wild type, i.e. the native or endogenous nucleic acid or polypeptide. Alternatively, it may be a protein or nucleic acid derived from the same or another species. The nucleic acid/gene may then be introduced into a plant as a transgene, for example by transformation.

The nucleic acid may be isolated from a bacteria, yeast or fungi, or from a plant, algae, insect or animal (including human) source. This nucleic acid may be substantially modified from its native form in composition and/or genomic environment through deliberate human manipulation. The nucleic acid is preferably obtained from a plant, whether from the same plant species in which it is to be introduced or whether from a different plant species. Further preferably, the nucleic acid is from a dicot, preferably from the family Brassicaceae, further preferably from *Arabidopsis thaliana*. More preferably, the nucleic acid is essentially similar to a nucleic acid as represented by SEQ ID NO 1, or a portion of SEQ ID NO 1, or a nucleic acid capable of hybridising therewith or is a nucleic acid encoding an amino acid sequence essentially similar to an amino acid as represented by SEQ ID NO 2, or a homologue, derivative or active fragment thereof.

Advantageously, the methods according to the invention may also be practised using variant 2×C2H2 zinc finger nucleic acids and variant 2×C2H2 zinc finger amino acids, preferably wherein the variant nucleic acids are variants of SEQ ID NO 1 and wherein the variant amino acids are variants of SEQ ID NO 2. Examples of variant sequences suitable in performing the methods of the invention include:

(i) Functional portions of a 2×C2H2 zinc finger nucleic add/gene;
(ii) Sequences capable of hybridising with a 2×C2H2 zinc finger nucleic acid/gene;
(iii) Alternative splice variants of a 2×C2H2 zinc finger nucleic acid/gene;
(iv) Allelic variants of a 2×C2H2 zinc finger nucleic acid/gene;
(v) Homologues, derivatives and active fragments of a 2×C2H2 zinc finger protein.

The abovementioned variants may also be described as being "essentially similar" to a 2×C2H2 zinc finger nucleic acid/gene, particularly to the 2×C2H2 zinc finger encoding nucleic acid of SED ID NO 1, or essentially similar to a 2×C2H2 zinc finger amino acid/protein, particularly that of SED ID NO 2. The term "essentially similar to" also includes variants of SEQ ID NO 1 in the form of a complement, DNA, RNA, cDNA or genomic DNA. The variant nucleic acid encoding a 2×C2H2 zinc finger protein or the variant of a 2×C2H2 zinc finger protein may be synthesized in whole or in part, it may be a double-stranded nucleic add or a single-stranded nucleic add. Also, the term encompasses a variant due to the degeneracy of the genetic code; a family member of the gene or protein; and variants that are interrupted by one or more intervening sequences.

An example of a variant 2×C2H2 zinc finger nucleic acid is a functional portion of a 2×C2H2 zinc-finger gene. Advantageously, the method according to the present invention may also be practised using portions of a DNA or nucleic acid encoding a 2×C2H2 zinc finger protein. A functional portion refers to a piece of DNA derived or prepared from an original (larger) DNA molecule, which DNA portion, when expressed in a plant, gives plants having modified growth characteristics. The portion may comprise many genes, with or without additional control elements or may contain spacer sequences. The portion may be made by making one or more deletions and/or truncations to the nucleic acid. Techniques for introducing truncations and deletions into a nucleic acid are well known in the art. Portions suitable for use in the methods according to the invention may readily be determined by following the methods described in the Examples section by simply substituting the sequence used in the actual Example with the portion to be tested for functionality.

An example of a further variant 2×C2H2 zinc finger nucleic acid is a sequence that Is capable of hybridising to a 2×C2H2 zinc finger nucleic acid, for example to any of SEQ ID NO 1, 10, 12, 14, 16, 18, 20, 22, 24, 26, 28, 30, 32, 34, 36, 38, 40, 41, 43, 45, 47 or 49. Advantageously, the methods according to the present invention may also be practised using these variants. Hybridising sequences suitable for use in the methods according to the invention may readily be determined for example by following the methods described in the Examples section by simply substituting the sequence used in the actual Example with the hybridising sequence.

The term "hybridisation" as defined herein is a process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the Isolation of poly (A+) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic add arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and $Na_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions may be designed in function of the known or the expected homology and/or length of the nucleic acid sequence. Sufficiently low stringency hybridisation conditions are particularly preferred (at least in the first instance) to isolate nucleic acids heterologous to the DNA sequences of the invention defined supra. An example of low stringency conditions is 4-6×SSC/0.1-0.5% w/v SDS at 37-45° C. for 2-3 hours. Depending on the source and concentration of the nucleic acid involved in the hybridisation, alternative conditions of stringency may be employed, such as medium stringency conditions. Examples of medium stringency conditions include 1-4×SSC/0.25% w/v SDS at ≧45° C. for 2-3 hours. An example of high stringency conditions includes 0.1 to 2×SSC/0.1% w/v SDS at 60° C. for 1-3 hours. The skilled man will be aware of various parameters which may be altered during hybridisation and washing and which will either maintain or change the stringency conditions. The stringency conditions may start low and be progressively increased until there is provided a hybridising nucleic acid, as defined hereinabove. Elements contributing to heterology include allelism, degeneration of the genetic code and differences in preferred codon usage.

Another variant 2×C2H2 zinc finger nucleic acid useful in practising the methods according to the present invention is an alternative splice variant of a nucleic acid sequence encoding a 2×C2H2 zinc finger protein. The term "alternative splice variant" as used herein encompasses variants of a nucleic acid sequence in which selected introns and/or exons have been excised, replaced or added. Such splice variants may be found in nature or may be manmade. Methods for making such splice variants are well known in the art. Splice variants suitable for use in the methods according to the invention may readily be determined for example by following the methods described in the Examples section by simply substituting the sequence used in the actual Example with the splice variant.

Another variant 2×C2H2 zinc finger nucleic acid useful in practising the methods according to the present invention is an allelic variant of a nucleic acid encoding a 2×C2H2 zinc finger protein. Allelic variants exist in nature and encompassed within the methods of the present invention is the use of these natural alleles. Allelic variants also encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms. Allelic variants suitable for use in the methods according to the invention may readily be determined for example by following the methods described in the Examples section by simply substituting the sequence used in the actual Example with the allelic variant.

The present invention provides a method for modifying plant growth characteristics, comprising modifying expression in a plant of an alternative splice variant or expression in a plant of an allelic variant of a nucleic acid encoding a 2×C2H2 zinc finger protein and/or by modifying level and/or activity in a plant of a 2×C2H2 zinc finger protein encoded by the alternative splice variant or allelic variant.

Examples of variant 2×C2H2 zinc finger proteins useful in practicing the methods of the present invention are homologues, derivatives or functional fragments of a 2×C2H2 zinc finger protein.

"Homologues" of a 2×C2H2 zinc finger protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company). The homologues useful in the method according to the invention have at least in increasing order of preference 30%, 31%, 32%, 33%, 34%, 35%, 36%, 37%, 38%, 39%, 40%, 41%, 42%, 43%, 44%, 45%, 46%, 47%, 48%, 49%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98% sequence identity or similarity to an unmodified protein.

The percentage of identity may be calculated by using an alignment program well known in the art For example, the percentage of identity may be calculated using the program GAP, or needle (EMBOSS package) or stretcher (EMBOSS package) or the program align X, as a module of the vector NTI suite 5.5 software package, using the standard parameters (for example GAP penalty 5, GAP opening penalty 15, GAP extension penalty 6.6).

According to another embodiment of the present invention, the nucleic acid sequence useful in the methods of the present invention is a nucleic acid encoding a protein homologous to SEQ ID NO 2.

Methods for the search and identification of 2×C2H2 zinc finger protein homologues, for example STZ zinc finger homologues, would be well within the realm of a person skilled in the art. Such methods, involve screening sequence databases with the sequences provided by the present invention, for example SEQ ID NO 2 (or SEQ ID NO 1), preferably in a computer readable format. This sequence information may be available in public databases, that include but are not limited to Genbank (URL: ncbi.nlm.nih.gov/web/Genbank), the European Molecular Biology Laboratory Nucleic acid Database (EMBL) (URL: w.ebi.ac.uk/ebi-docs/embl-db.html) or versions thereof or the MIPS database (URL: mips.gsf.de/). Different search algorithms and software for the alignment and comparison of sequences are well known in the art. Such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., GenomeAnalysis, 1: 543, 1997). The software for performing BLAST analysis is publicly available through the National Centre for Biotechnology Information.

Default blast parameters to find useful homologues of any of SEQ ID NO 1, SEQ ID NO 2 or any of SEQ ID NO 10 to SEQ ID NO 50, are, when comparing nucleotide sequence G (Cost to open a gap) 5, E (Cost to extend a gap default) 2, q (Penalty for a mismatch)-3, r (Reward for a match) 1, e (Expectation value (E)) 10.0, W (Word size) 11, V (Number of one-line descriptions) 100 and B (Number of alignments to show) 100. When comparing protein sequences, the default parameters are preferably G 11, E 1, e value 10.0, W 3, V 100 and B 100.

The above-mentioned analyses for comparing sequences, for the calculation of sequence identity and for the search for homologues, is preferentially done with full-length sequences or within a conserved region of the sequence. Therefore, these analyses may be based on a comparison of certain regions such as conserved domains, motifs or boxes.

The identification of such domains or motifs for examples the motif and boxes as represented by SEQ ID NO 5, 6, 7, 8 and 9, would also be well within the realm of a person skilled in the art and involves for example, a computer readable format of proteins of the present invention, the use of alignment software programs and the use of publicly available information on protein domains, conserved motifs and boxes. This protein domain information is available in the PRODOM (URL: biochem.ucl.ac.uk/bsm/dbbrowser/jj/prodomsrchijj.html), PIR (URL: pir.georgetown.edu/) or pFAM (URL: pfam.wustl.edu/) database. For the identification of Zinc finger domains, such as the 2×C2H2 zinc finger domain, pFAM is preferred. Sequence analysis programs designed for motif searching may be used for identification of fragments, regions and conserved domains as mentioned above. Preferred computer programs would include but are not limited to MEME, SIGNALSCAN, and GENESCAN. A MEME algorithm (Version 3.0) may be found in the GCG package; or on the Internet site URL: sdsc.edu/MEME/meme. SIGNALSCAN version 4.0 information is available on the Internet site URL: biosci.cbs.umn.edu/software/sigscan.html.

GENESCAN may be found on the Internet site URL: gnomic.stanford.edu/GENESCANW.html.

At present, zinc finger motifs are subdivided in more than 40 different classes as can be found in the Pfam database of protein families present at the Sanger institute (URL: sangerac.ac.uk/Software/Pfam/browse/Z.shtml).

The C2H2 zinc finger (Zf-C2H2) motif is the classical zinc finger domain. It was first recognized in the transcription factor IIIA (TFIIIA) of *Xenopus* (Miller at al. 1985). The domain is typically 25 to 30 amino-acid residues in length. The following pattern describes the zinc finger *X-C-X(1-5)-C-X3-*X5-*X2-H-X(3-6)-[H/C] where X can be any amino acid, and numbers in brackets indicate the number of residues. The positions marked * are those that are important for the stable folding of the zinc finger. The final position can be either his or cys, while still being a C2H2 zinc finger domain. In view of recent publications on the design of zinc finger domains it becomes feasible also to replace one or more of the Cys or His amino acids, whilst still retaining the original functionality of the C2H2 domain. The residues separating the second Cys and the first His are mainly polar and basic. The canonical C2H2 zinc finger is composed of two short beta strands followed by an alpha helix. DNA binding of the zinc finger motif is mediated by amino terminal part of the alpha helix which binds the major groove in DNA binding zinc fingers. C2H2 domains have been shown to interact with RNA, DNA and proteins. The tetracoordination of a Zinc ion by the conserved cystein and histidine residues determines the conserved tertiary structure of the motif. Conserved hydrophobic residues are commonly found at positions −2 and also at 4 amino acids after the second cysteine (that participates in zinc binding) and at position three before the first histidine (that participates in zinc binding). In plant multi zinc finger proteins, spacing between the C2H2 domains is generally about 15 to about 65 amino acids.

Thus, plant zinc finger proteins are characterized by long spacers of diverse lengths between adjacent fingers. Moreover, they are characterised by a highly conserved sequence of six amino acids, located within a putative DNA-contacting surface of each finger. Two forms of such conserved sequence are most commonly found in plant C2H2 zinc fingers, the QALGGH (SEQ ID NO 5) and the NNM/WQMH (SEQ ID NO 6). Despite the high sequence conservation of the QALGGH (SEQ ID NO:5), some variants or the so-called 'modified type' occur in nature where one or two amino acids can have a different form, most typically the +1 "Q" can be a "G", "K" or "R" (these amino acids share the same turn-like characteristic), the +2 "A" can be "S" (both of which share the characteristic of being small amino acids) or the +3 "L " can be "F" (these two amino acids are both hydrophobic). The QALGGH-motif (SEQ ID NO:5) as used herein comprises all these variants. In the NNM/WQMH (SEQ ID NO:6) motif at position 3 there is mostly an "M" or a "W".

Therefore, the present invention provides a method as described hereinabove, wherein said 2×C2H2 zinc finger protein comprises a QALGGH (SEQ ID NO:5) motif. Further, The present invention provides as described hereinabove, wherein said 2×C2H2 zinc finger protein comprises a NNM/WQMH (SEQ ID NO:6) motif.

According to one embodiment of the invention, both C2H2 domains are of the same type. More preferably, both C2H2 zinc finger domains have the same conserved QALGGH (SEQ ID NO:5) or NNM/WQMH (SEQ ID NO:6) motif. According to another embodiment, each C2H2 zinc finger domain has a different conserved motif.

According to one embodiment, the 2×C2H2 protein useful in the methods of the present invention is characterized by an EAR motif, which is an ERF-Associated amphiphilic repression motif. This motif has been recognized in two unrelated types of transcription factors, namely the ERF transcription factors of the AP2 type and in the zinc finger transcription factors. In the latter class, the EAR motif is generally located at the C-terminus of the protein. The pattern for the EAR motif has the conserved sequence hDLNh(X)P (SEQ ID NO 7), where "h" is a hydrophobic residue (any one of A,C,F,G, H,I,K,L,M,R,T,V,W,Y) most typically L/F/I and where "X" can be one (any amino acid) or no amino acid. A characteristic feature of the EAR motif is the alternation of hydrophilic and hydrophobic residues with the aspartic add (D) residue being amphiphilic. Ohta et al. (The plant cell, 2001, 13, p1959-1968), which reference is cited herein by reference, previously characterized EAR motifs present in 2×C2H2 zinc finger proteins.

Therefore, the present invention provides a method as described hereinabove, wherein the 2×C2H2 zinc finger protein comprises an EAR motif. According to one embodiment, the EAR motif is located in the C-terminal region of the protein, preferably between the second zinc finger domain and the C-terminus.

According to a further embodiment, the zinc finger proteins used in the methods of the present invention have two zinc finger domains and a nuclear localization signal (B-box). A cluster of basic amino acids that resembles the B-box (Basic box) were described by Chua et al. (EMBO 1992-11, 241-9) and were hypothesized to be a nuclear localization signal for the protein. These have been recognized in 2×C2H2 proteins (Sakamoto et al., Gene 248 (2000) 23-32). The cluster is rich in Lysine (K) and Arginine (R) residues. A consensus sequence defining the most frequent form of the B-box in 2×C2H2 genes is KR(S)KRXR (SEQ ID NO 8) where "S" at the 3rd position may be absent or present. However other variants may occur in nature that still retain the characteristic of being a charged region rich in basic amino acids. The location of the basic box is most frequently at the N-terminus of the protein, but can also occur in other locations. It has been speculated that due to its basic nature the B-box could also participate in DNA binding.

Accordingly, the present invention provides a method as described hereinabove, wherein the 2×C2H2 zinc finger protein further comprises a B-box. According to one embodiment the B-box is located in the N-terminal region of the zinc finger protein. Preferably the proteins useful in the methods of the present invention have a B-box located between the N-terminus and the first zinc finger domain.

According to a further embodiment, the zinc finger proteins useful in the methods of the present invention have two C2H2 zinc finger domains and an L-box. A conserved motif, named L-box, of yet unknown function has been identified in 2×C2H2 proteins and has been described previously by Sakamoto et al. (Gene 248 (2000) 23-32). The L-box is typically located at the N-terminus, between the B-box and the first C2H2 zinc finger. The L-box is represented by the sequence EXEXXAXCLXXL (SEQ ID NO 9). This region may be involved in protein-protein interactions. Zinc finger proteins lacking the L-box, may for example have serine rich regions at a similar position, which regions are putative sites for protein-protein interactions.

Therefore, the present invention provides a method as described hereinabove, wherein the 2×C2H2 protein comprises an L-box.

Particular zinc finger homologues useful in the methods of the present invention have one or more of the conserved motifs as depicted in SEQ ID NO 5, 6, 7, 8 and 9, or motifs that are 80% identical to these motifs or motifs that have conserved substitutions of amino acids. The 2×C2H2 protein as set forth in SEQ ID NO 2 comprises all the boxes as set forth in SEQ ID NO 5, 7, 8 and 9. All its paralogues and orthologues also comprise all of these boxes.

Homologues of a 2×C2H2 protein as presented in SEQ ID NO 2 and isolated from *Arabidopsis thaliana*, that are useful in the constructs and the methods of the present invention are also identified in other plant species.

Two special forms of homologue, orthologues and paralogues, are evolutionary concepts used to describe ancestral relationships of genes. The term “paralogue” relates to a gene-duplication within the genome of a species leading to paralogous genes. The term “orthologue” relates to a homologous gene in different organisms due to ancestral relationship. The term “homologue” as used herein also encompasses paralogues and orthologues of the proteins useful in the methods according to the invention.

Othologues in other plant species may easily be found by performing a so-called reciprocal blast search. Orthologous genes can be identified by querying one or more gene databases with a query gene or protein of interest (SEQ ID NO 1 or 2), using for example BLAST program. The highest-ranking subject genes that result from the search are then again subjected to a BLAST analysis, and only those subject genes that match again with the query sequence (SEQ ID NO 1 or 2) are retained as true orthologous genes. For example, to find a rice orthologue of an *Arabidopsis thaliana* gene, one may perform a BLASTN or TBLASTX analysis on a rice database such as (but not limited to) the *Oryza sativa Nipponbare* database available at the NCBI website (URL: ncbi.nlm.nih.gov) or the genomic sequences of rice (cultivars *indica* or *japonica*). In a next step, the obtained rice sequences are used in a reverse BLAST analysis using an *Arabidopsis* database. The results may be further refined when the resulting sequences are analysed with ClustalW and visualised in a neighbour joining tree. The method can be used to identify orthologues from many different species.

The closest homologues in other species (orthologues of the protein of SEQ ID NO 2), include those from a variety of dicot and monocot plants, for example from *Datisca glomerata* (AF119050_1, AAD26942, SEQ ID NO 10 and 11), from soybean (T09602, SCOF-1, SEQ ID NO 12 and 13), *Medicago sativa* (CAB77055.1, SEQ ID NO 14 and 15), from tobacco (T01985, SEQ ID NO 16 and 17) from rice, (AF332876_1, AAK01713.1, SEQ ID NO 18 and 19), from petunia (BAA05079.1, SEQ ID NO 20 and 21), from wheat (S39045 and BM03901, WZF1, SEQ ID NO 22 and 23), from *Capsicum annum* (SEQ ID NO 24 and 25), from turnip (T14408, T14409) and from sugarcane (CA279020).

Close homologues of the same species (paralogues of the protein of SEQ ID NO 2 from *Arabidopsis thaliana*) are described below.

The MIPS database contains the sequence of the *Arabidopsis thaliana* genome with prediction and functional annotation of the proteins encoded. Searching this database with the STZ gene of SEQ ID NO 1 (MIPS accession number At1g27730), showed that in the *Arabidopsis* genome there are 2 genes encoding very close homologues of SEQ ID NO 2, At5g43170 (NM_123683, SEQ ID NO 32 and 33) and At5g04340 (NM_120516 SEQ ID NO 28 and 29), and 3 others with high similarity: At3g19580 (NM_112848, SEQ ID NO 26 and 27), At5g67450 (NM_126145, SEQ ID NO 34 and 35) and At3g49930 (NM_114853, SEQ ID NO 30-31). These genes are spread over 3 chromosomes, 1, 3 and 5. Similarly, a number of paralogues of the orthologue in Petunia have been isolated and sequenced. Advantageously, paralogues from the same species may be used in the methods of the present invention.

Furthermore, a number of family members of the STZ protein of SEQ ID NO 2 have been found in *Arabisopsis*. The STZ gene and protein of SEQ ID NO 1 and 2 have been previously published in the database under the MIPS accession number At1g27730 or in Genbank under the accession numbers NP_174094.1, X95573 or CAA64820. Additionally, several other cDNA’s, isolated from other tissues or at different developmental stages of *Arabisopsis* have been reported and encode the same protein as that of SEQ ID NO 2. Such sequences sequences deposited under the Genbank accession number AY034998, NM_102538, AC12375, X95573, AY063006, X98671, X98670, or AF250336. These isolates illustrate the differential expression of the STZ gene in different plant tissues at different developmental stages. The differential regulation of these different cDNA’s is reflected by the differences at their 5'UTR and the 3'UTR regions, while the encoded protein remains the same. Advantageously, the members of the same gene family as SEQ ID NO 1 or the members of the same family of any of the orthologues of SEQ ID NO 1, may be used in the methods of the present invention.

Other close homologues useful in the methods of the present invention are the sequences as deposited in the public database under the following accession numbers, which sequences are herein incorporated by reference: homologues isolated from *Petunia*: BAA21923.1, BAA21922.1, BAA21926.1, BAA21925.1, BAA19110.1, BAA19926.1, BAA21924.1, BAA19111.1, BAA21921.1, BAA19114.1, BAA05076.1, BAA05079.1, CAA43111.1, BAA21920.1, BAA21919.1, BAA05077.1, BAA05078.1, BAA20137.1; homologues isolated from *Arabidopsis*: CAA67229.1, BAC43454.1, NP_196054.1, AAM67193.1, NP_199131.1, NP_188592.1, NP_201546.1, NP_190562.1, NP_182037.1, BAC43008.1, Q8VWG3, CAC86393.1, CAC86168.1, CAC86167.1, CAC86166.1, CAB67667.1, CAC01747.1, CAB90936.1, CAB90935.1, CAB80245.1, CAB41188.1, CAA18741.1, CAA67234.1, CAA67236.1, CAA67231.1, CAA67230.1, CAA67228.1, CAA67235.1, CAA67233.1, CAA67232.1, CAA67229.1, CAA64820.1 and homologues isolated from rice: BAB16855.1, AAO06972.1, CAC09475.1, BAB63718.1, P0683F02.21, BAB67885.1, P0031D11.19, BAB64114.1, AAK01713.1, AF332876_1, AAL76091.1, BAB67879.1P0031D11.12 and BAC15513.1.

A phylogenetic tree may be constructed with all the homologues, paralogues and orthologues are defined herein above. Multiple alignmentq may be made using clustal W present in the VNTi (version 5.0) program with for example Gap opening penalty 10 and Gap extention 5. For making a phylogenetic tree the Phylic software package available at URL: evolution.genetics.washington.edu/phylip.html may be used. Sequences clustering around SEQ ID NO 1 or SEQ ID NO 2, identify genes or proteins suitable for use in the methods of the present invention.

The sequence of SEQ ID NO 2 and its rice orthologue AF332876 (SEQ ID NO 19) have 36% sequence identity when using the program Needle with the parameters Gap penalty 5 and Gap extension penalty 6. Therefore, homologues particularly useful in the methods of the present invention are homologues having 36% or more sequence identity with the 2×C2H2 zinc finger protein as presented in SEQ ID NO 2 or having 36% or more sequence identity to the closest orthologue of SEQ ID NO 2 from another species.

Preferred homologues useful in practicing the methods of the present invention are plant homologues, i.e. proteins obtained from a plant nucleic acid. More preferably, the nucleic acid sequence is from a dicot, more preferably from the family Brassicaceae, further preferably from *Arabidopsis thaliana.*

Preferably the 2×C2H2 zinc finger protein useful in the methods of the present invention belongs to the same gene family as the salt tolerant zinc finger protein (STZ) of *Arabidopsis thaliana*, or is a homologues thereof. The name ZAT10 can also be used to identify the STZ zinc finger protein of *Arabidopsis thaliana.*

Another variant of a zinc finger protein useful in the methods of the present invention is a substitutional variant. The term "Substitutional variants" of a protein refers to those variants in which at least one residue in an amino acid sequence has been removed and a different residue inserted in its place. Amino acid substitutions are typically of single residues, but may be clustered depending upon functional constraints placed upon the polypeptide; insertions will usually be of the order of about 1-10 amino acid residues, and deletions will range from about 1-20 residues. Preferably, amino acid substitutions comprise conservative amino acid substitutions. Particular substitutional variants of the C2H2 zinc finger protein are substitutional variants in which one or more of the conserved Cys and/or His residues is replaced, whilst retaining the same zinc finger functionality. To retain the same functionality, the residues around these conserved Cys of His residues may also be substituted.

"Insertional variants" of a protein are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$(SEQ ID NO:52)-tag, glutathione S-transferase-tag, protein A, maltose-binding protein, dihydrofolate reductase, Tag●100 epitope, c-myc epitope, FLAG®-epitope, lacZ, CMP (calmodulin-binding peptide), HA epitope, protein C epitope and VSV epitope.

"Deletion variants" of a protein are characterised by the removal of one or more amino acids from the protein. Amino acid variants of a protein may readily be made using peptide synthetic techniques well known in the art such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The term "derivatives" refers to peptides, oligopeptides, polypeptides, proteins and enzymes which may comprise substitutions, deletions or additions of naturally and non-naturally occurring amino acid residues compared to the amino acid sequence of a naturally-occurring form of the 2×C2H2 protein such as for example the 2×C2H2 zinc finger protein as presented in SEQ ID NO 2. "Derivatives" of a 2×C2H2 zinc finger protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence such as, for example, a reporter molecule which is bound to facilitate its detection, and non-naturally occurring amino acid residues relative to the amino acid sequence of a naturally-occurring protein.

Another variant of a 2×C2H2 zinc finger protein useful in the methods of the present invention is an active fragment of a zinc finger protein. "Active fragments" of a 2×C2H2 zinc finger protein encompasses at least five contiguous amino acid residues of a protein, which residues retain similar biological and/or functional activity to the naturally occurring protein. For example, useful fragments comprise at least 10 contiguous amino acid residues of a 2×C2H2 zinc finger protein. Other preferred fragments are fragments of a 2×C2H2 zinc finger protein starting at the second or third or further internal methionin residues. These fragments originate from protein translation, starting at internal ATG codons. Functional fragments of a 2×C2H2 zinc finger protein useful in practising the methods of the present invention may have one, two or no C2H2 domains, without affecting its functionality in the methods of the present invention.

According to a preferred feature of the present invention, enhanced or increased expression of a nucleic acid encoding a 2×C2H2 zinc finger protein is envisaged. Methods for obtaining enhanced or increased expression of genes or gene products are well documented in the art and include, for example, over-expression driven by a strong promoter, the use of transcription enhancers or translation enhancers. The term over-expression as used herein means any form of expression that is additional to the original wild-type expression level. Preferably the nucleic acid to be introduced into the plant and/or the nucleic acid that is to be overexpressed in the plant is in the sense direction with respect to the promoter to which it is operably linked. Preferably, the nucleic acid sequence represented by SED ID NO 1 is over-expressed in a plant. However, it should be clear that the applicability of the invention is not limited to use of the nucleic acid represented by SEQ ID NO 1 nor to the nucleic acid sequence encoding the amino acid sequence of SEQ ID NO 2, but that other nucleic acid sequences encoding homologues, derivatives or active fragments of SED ID NO 1 or SED ID NO 2 may be useful in the methods of the present invention. Examples of nucleic acids or proteins are provided in SEQ ID NO 10 to SEQ ID NO 50.

Alternatively and/or additionally, increased expression of a 2×C2H2 encoding gene or increased level and/or activity of a 2×C2H2 protein in a plant cell, is achieved by mutagenesis.

For example these mutations may be responsible for altered control of the 2×C2H2 gene, resulting in more expression of the gene, relative to the wild-type gene. Mutations can also cause conformational changes in a protein, resulting in more activity and/or higher levels of the 2×C2H2 protein.

Modifying gene expression (whether by a direct or indirect approach) encompasses altered transcript levels of a gene. Altered transcript levels may be sufficient to induce certain phenotypic effects, for example via the mechanism of cosuppression. Here the overall effect of introduction of a transgene is that there is less activity in the cell of the protein encoded by a native gene having homology to the introduced transgene.

Therefore, according to another embodiment of the present invention, there is provided a method for modifying growth characteristics in a plant, comprising decreasing expression of a gene encoding a 2×C2H2 zinc finger protein or decreasing level and/or activity of a 2×C2H2 zinc finger protein. Examples of decreasing expression, level and/or activity of a protein in a cell are well documented in the art and include, for example, downregulation of expression by anti-sense techniques, RNAi techniques, small interference RNAs (siRNAs) and microRNA (mRNA).

Another method for downregulation of gene expression or gene silencing comprises use of ribozymes, for example as described in Atkins et al. 1994 (WO 94/00012), Lenee et al. 1995 (WO 95/03404), Lutziger et al. 2000 (WO 00/00619), Prinsen et al. 1997 (WO 97/3865) and Scott et al. 1997 (WO 97/38116).

Gene silencing may also be achieved by insertion mutagenesis (for example, T-DNA insertion or transposon insertion) or by gene silencing strategies as described by, among others, Angell and Baulcombe 1998 (WO 98/36083), Lowe et al. 1989 (WO 98/53083), Lederer et al. 1999 (WO 99/15682) or Wang et al. 1999 (WO 99/53050).

Expression of an endogenous gene may also be reduced if it contains a mutation. Such a mutation or such a mutant gene may be isolated and introduced into the same or different plant species in order to obtain plants having modified growth characteristics. Examples of such mutants are dominant negative mutants of a 2×C2H2 zinc finger gene.

Genetic constructs aimed at silencing gene expression may comprise the 2×C2H2 zinc finger nucleic acid, for example as represented by SEQ ID NO 1 (or one or more portions thereof or a sequence capable of hybridising therewith), in a sense and/or antisense orientation relative to the promoter sequence. The sense or antisense copies of at least part of the endogenous gene in the form of direct or inverted repeats may also be utilised in the methods according to the invention. The growth characteristics of plants may also be modified by introducing into a plant at least part of an antisense version of the nucleotide sequence represented by SEQ ID NO 1.

According to a further embodiment of the present invention, genetic constructs and vectors to facilitate introduction and/or to facilitate expression of the 2×C2H2 zinc finger nucleotide sequences useful in the methods according to the invention are provided. Therefore, according to the present invention, there is provided a construct comprising:

(i) a nucleic acid capable of modifying expression of a nucleic acid encoding a 2×C2H2 zinc finger protein and/or modifying level and/or activity of a 2×C2H2 zinc finger protein;
(ii) one or more control sequence capable of driving expression of the nucleic acid sequence of (i); and optionally
(iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. Preferably the genetic construct is a plant expression vector.

The nucleic acid according to (i) is advantageously any of the nucleic acids described hereinbefore. A preferred nucleic acid is the nucleic acid represented by SEQ ID NO 1 or a variant thereof as hereinbefore defined, or is a nucleic acid sequence encoding a sequence represented by SEQ ID NO 2 or a variant as hereinbefore defined. For example such variants encode a protein as presented in any of SEQ ID NO 11, 13, 15, 17, 19, 21, 23, 25, 27, 29, 31, 33, 35, 37, 39, 42, 44, 46, 48 and 50.

The terms "regulatory element" and "control sequence" are used herein interchangeably and are to be taken in a broad context to refer to regulatory nucleic acids capable of effecting expression of the sequences to which they are operably linked. Encompassed by the aforementioned terms are promoters. A "promoter" encompasses transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest. Preferably, the gene of interest is operably linked to a promoter in a sense direction.

Advantageously, any type of promoter may be used to drive expression of the nucleic acid sequence depending on the desired outcome.

Promoters useful for the present invention are described in EP 03075331.3, which promoters and sequences are incorporated herein by reference.

Other examples of preferred promoters are presented in Table 1 (a) to (c), which promoters or derivatives thereof are useful in the methods and/or in making the constructs of the present invention. Accordingly, genetic constructs comprising of the nucleic acids of (i), for example a 2×C2H2 nucleic acid, and at least part of a promoter from Table 1 (a) to (c) or from EP 03075331.3, preferably, wherein said parts are operably linked, are also provided by the present invention.

According to onother embodiment, the nucleic acid of (i) is operably linked to a constitutive promoter. The term "constitutive" as defined herein refers to a promoter that is expressed substantially continuously. Furthermore, preferably the constitutive promoter is a ubiquitous promoter, which is expressed in more than one, preferably in most or substantially all tissues of the plant. Preferably, the constitutive promoter to be used in the methods of the present invention, or cloned in the genetic constructs of the present invention, is a plant promoter, preferably a constitutive promoter, such as a GOS2 promoter or a promoter with similar strength and/or similar expression pattern. Preferably plant promoters derived from a plant nucleic acid are used. Alternatively, promoters operable in plant, such as promoters derived from plant pathogens are used.

According to another embodiment of the invention, the nucleic acid of (i) is operably linked to a plant promoter, preferably a tissue-preferred promoter. The term "tissue-preferred" as used herein refers to a promoter that is expressed predominantly in at least one tissue or organ. For example, the tissue-preferred promoter is a seed-preferred promoter, such as a pWS18 (Joshes et al. Plant Cell Physiol. 1998 January; 39(1):64-72.) or a promoter of similar strength and/or similar expression pattern.

Promoters with similar strength and/or similar expression pattern may be found by coupling the promoter to a reporter gene and checking the function of the reporter gene in different tissues of a plant. One suitable reporter gene is beta-glucuronidase and the colorimetric GUS staining to visualize the beta-glucuronidase activity in a plant tissue is well known to a person skilled in the art.

TABLE I (a)

flower preferred promoters useful in the present invention. Sequences of these promoters are described in the cited reference, which sequences are herein incorporated by reference.

| Gene | Expression | Reference |
|---|---|---|
| AtPRP4 | flowers | URL: salus.medium.edu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala-3 | flowers | |

TABLE I (b)

seed-preferred promoters useful in the present invention. Sequences of these promoters are described in the cited reference, which sequences are herein incorporated by reference.

| Gene | Expression | Reference |
|---|---|---|
| seed-specific genes | seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| zein | seed | Matzke et al Plant Mol Biol, 14(3): 323-32 1990 |
| napA | seed | Stalberg, et al, Planta 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadlns | endosperm | EMBO 3: 1409-15, 1984 |
| barley Itr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| biz2 | endosperm | EP99106056.7 |
| synthetic promoter | endosperm | Vlcente-Carbajosa et al., Plant J. 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice α-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46,1997 |
| sorgum γ-kaflrin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |

TABLE I (c)

constitutive promoters useful in the present invention. Sequences of these promoters are described in the cited reference, which sequences are herein incorporated by reference.

| Gene | Expression | Reference |
|---|---|---|
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant. 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| rice cyclophilin | constitutive | Buchholz et al, Plant Mol Biol. 25(5): 837-43, 1994 |
| maize H3 histone | constitutive | Lepetit et al, Mol. Gen. Genet. 231: 276-285, 1992 |
| actin 2 | constitutive | An et al, Plant J. 10(1); 107-121, 1996 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a genetic construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include genes conferring resistance to antibiotics (such as nptII encoding neomycin phosphotransferase capable of phosphorylating neomycin and kanamycin, or hpt encoding hygromycin phosphotransferase capable of phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example beta-glucuronidase, GUS), luminescence (such as luciferase) or fluorescence (Green Fluorescent Protein, GFP, and derivatives thereof). Further examples of suitable selectable marker genes include the ampicillin resistance (Ampr), tetracycline resistance gene (Tcr), bacterial kanamycin resistance gene (Kanr), phosphinothricin resistance gene, and the chloramphenicol acetyltransferase (CAT) gene, amongst others The present invention also encompasses plants obtainable by the methods according to the present invention. The present invention therefore provides plants obtainable by the method according to the present invention, which plants have modified growth characteristics, which plants have altered 2×C2H2 zinc finger protein level and/or activity and/or altered expression of a nucleic acid sequence encoding a 2×C2H2 zinc finger protein.

Therefore, according to one aspect of the present invention, there is provided a method for the production of plants, having modified growth characteristics, comprising introducing, into a plant, a nucleic add capable of modifying activity of a 2×C2H2 zinc finger protein and/or capable of modifying expression of a 2×C2H2 zinc-finger gene. According to a further embodiment of the present invention, there is provided a method for the production of transgenic plants having modified growth characteristics, comprising introduction and expression in a plant of a 2×C2H2 nucleic acid.

More specifically, the present invention provides a method for the production of transgenic plants having modified growth characteristics, which method comprises:

(i) introducing into a plant or plant cell a 2×C2H2 zinc finger nucleic add;

(iii) cultivating the plant cell under conditions promoting plant growth.

The growth characteristic may be any of the characteristics defined hereinunder.

The 2×C2H2 zinc finger nucleic acid includes all variant nucleic acids as described herein before and includes all nucleic acids encoding all variant proteins as described herein before. Cultivating the plant cell under conditions promoting plant growth, may or may not include regeneration and or growth to maturity.

The protein itself and/or the nucleic acid itself may be introduced directly into a plant cell or into the plant itself (including introduction into a tissue, organ or any other part of the plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell can then be used to regenerate a transformed plant in a manner known to persons skilled in the art.

Transformation of a plant species is now a fairly routine technique. Advantageously, any of several transformation methods may be used to introduce the nucleic acid of interest (e.g. the 2×C2H2 nucleic acid) into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. A preferred transformation method is an *Argobacterium* mediated transformation method.

Transgenic rice plants expressing a 2×C2H2 gene are preferably produced via *Agrobacterium*-mediated transformation using any of the well-known methods for rice transformation, such as the ones described in any of the following: published European patent application EP 1198985 A1, Aldemita and Hodges (Planta, 199, 612-617, 1996); Chan et al. (Plant Mol. Biol. 22 (3) 491-506, 1993); Hiei et al. (Plant J. 6 (2) 271-282, 1994); which disclosures are incorporated by reference herein as if fully set forth. In the case of corn transformation, the preferred method is as described in either Ishida et al. (Nat. Biotechnol. 1996 June; 14(6): 745-50) or Frame et al.

(Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be undertaken using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; donal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells having modified expression and/or level and/or activity of a 2×C2H2 zinc finger protein. Such host cells for example comprise genetic constructs as mentioned above. Preferred host cells according to the invention are derived from a plant, algae, bacterium, fungus, yeast, insect or animal. The invention also extends to harvestable parts of a plant such as but not limited to seeds, leaves, fruits, flowers, petals, stamen, stem cultures, stem, rhizomes, roots, tubers, bulbs or cotton fibers.

The term "plant" as used herein encompasses whole plants, ancestors and progeny of the plants and plant parts, including seeds, shoots, stems, roots (including tubers), and plant cells, tissues and organs. The term "plant" also encompasses suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including, fodder or forage legumes, ornamental plants, food crop, tree, or shrub selected from the list comprising *Acacia* spp., *Acer* spp., *Actinidia* spp.,*Aesculus* spp., *Agathis australis, Albizia amara, Alsophila tricolor, Andropogon* spp., *Arachis* spp, *Areca catechu, Astelia fragrans, Astragalus cicer, Baikiaea pluriuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Cenfroema pubescens, Chaenomeles* spp.,*Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowlana, Fragaria* spp., *Flemingia* spp, *Freycinetia banksii, Geranium thunbergil, Ginkgo biloba, Glycine javanica, Gliricidla* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnate, Iris* spp., *Leptarrhena pyrolifolia, Lespediza* spp., *Lettuca* spp., *Leucaena leucocephala, Loudetia* simplex, *Lotonus bainesil, Lotus* spp., *Macnotyloma axillare, Malus* spp., *Manihot esculenta, Medicago sativa, Metasequoia glyptostroboides, Musa sapientum, Nicotianum* spp., *Onobrychis* spp., *Omithopus* spp., *Oryza* spp., *Peltophorum africanum, Pennisetum* spp., *Persea gratissima, Petunia* spp., *Phaseolus* spp., *Phoenix canadensis, Phormium cookianum, Photinia* spp., *Picea glauca, Pinus* spp., *Pisum sativum, Podocarpus totara, Pogonarthria fleckil, Pogonarthria squarrosa, Populus* spp., *Prosopis cineraria, Pseudotsuga menziesil, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoladendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifollum* spp., *Triticum* spp., *Tsuga heterophylla, Vaccinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, trees and algae amongst others. According to a preferred embodiment of the present invention, the plant is a crop plant such soybean, sunflower, canola, alfalfa, rapeseed, cotton, tomato, potato or tobacco. According to another preferred embodiment of the present invention, the plant is a monocotyledonous plant, such as sugar cane, further preferably a cereal, most preferably the plant is selected from the group consisting of rice, maize, wheat, barley, millet, rye or oats.

In a particular embodiment of the present invention, proteins of one plant species (for example *Arabidopsis*) are introduced in another plant species (for example rice). It has been shown in the present invention that plant growth characteristics are improved by introduction of a 2×C2H2 zinc finger gene or protein from a dicot into a monocot.

According to a particular embodiment of the invention, there are provided methods as described above, wherein the plant is a monocot. More preferably the plant is rice or corn.

Advantageously, performance of the methods according to the present invention leads to plants having modified growth characteristics.

The term "growth characteristic" as used herein, preferably refers to anyone or more of, but is not limited to, yield, architecture and cycle time.

The term "yield" means the amount of harvested material. For crop plants yield also means the amount of harvested material per acre of production. Depending on the crop the harvested part of the plant may be a different part or tissue of the plant, such as seed (e.g. rice, sorghum or corn when grown for seed); total above-ground biomass (e.g. for corn, when used as silage), root (e.g. sugarbeet), fruit (e.g. tomato), cotton fibers, or any other part of the plant which is of economic value. "Yield" also encompasses yield stability of the plants, meaning that year after year, one can obtain the same yield from the progeny of the plants, without too much interference of external factors, such as weather conditions. "Yield" also encompasses yield potential, which as the maximum obtainable yield.

Yield maybe dependent on a number of yield components. The parameters for these components are well known by a person skilled in the art. For example breeders are well aware of the specific yield components and the corresponding parameters for the crop they are aiming to improve.

For example key yield components for corn include number of plants per hectare or acre, number of ears per plant, number of rows (of seeds) per ear, number of kernels per row, and thousand kernel weight. For silage corn typical parameters are the above ground biomass and energy content.

Key yield components for rice include number of plants per hectare or acre, number of panicles per plant, number of spikelets per panicle, seed filling rate (number of filled seeds) and thousand kernel weight. Preferentially methods for increasing yield of rice encompass increased number of flowers per panicle and an increased number of filled seeds. The parameter of increased total number of seeds may be linked to increased number of flowers. "Yield" further encompasses typical biomass components, such as above ground parts of a plant and the root system. General biomass parameters are area and dry weight. Specific parameters for above ground biomass further encompass above ground area and plant height. Specific parameters for the root system encompass root ratio, root length and penetration depth, root branching, root hair density, root pulling resistance and aerenchyma formation.

The plants of the present invention are characterized by increased number of filled seeds, increased total seed weight, increased total number of seeds and increased harvest index. Therefore the methods of the present invention are particularly favorable to be applied in cereals such as rice and corn (maize). Accordingly, a particular embodiment of the present invention relates to a method to increase yield of corn, comprising modifying expression of a nucleic acid encoding a 2×C2H2 zinc finger protein.

The plants of the present invention are characterized by an increase in thousand kernel weight and therefore the seed size or seed volume and/or the seed content and/or seed composition are altered by the methods of the present invention. The seeds provided by the methods of the present invention may have more nutritional value, more starch and/or more oil, possibly due to their bigger size.

The plants of the present invention are characterized by more above ground area. Therefore, the methods of the present invention are particularly favorable for crops grown for their green tissue and/or grown for their above ground biomass. The methods of the present invention are particularly useful for grasses, forage crops (such as forage corn (maize), clover, medicago etc.), trees, sugar cane etc.

The improvement in yield as obtained by the methods of the invention, may be obtained as a result of improvement of one or more of the above mentioned yield components and/or parameters.

The term "architecture" as used herein encompasses the appearance or morphology of a plant, including any one or more structural features or combination of structural features thereof. Such structural features include the shape, size, number, position, texture, arrangement, and pattern of any cell, tissue or organ or groups of cells, tissues or organs of a plant, including the root, leaf, shoot stem, petiole, trichome, flower, petal, stigma, style, stamen, pollen, ovule, seed, embryo, endosperm, seed coat, aleurone, fibre, cambium, wood, heartwood, parenchyma, aerenchyma, sieve element, phloem or vascular tissue, amongst others. Particular architectural characteristics that may be modified by the methods of the present invention are increased plant height, increased number or size of stems or stalks or tillers or panicles or pedicles, increased number or size of inflorescences, increased branching of for example of tassels and ears or altered flowering characteristics. A preferred architectural characteristic that may be modified by the methods of the present invention is leaf architecture. The term "leaf architecture" as used herein comprises typical leaf characteristics such as length, width, thickness, cell number, cell size and greenness.

Typically, the plants of the present invention display increased leaf surface area and/or increased leaf blade width. This trait is particularly important as it allows the plant to optimize the shape of its leaf to maximize the area used for photosynthesis. For that purpose, preferably the leaf blade is widened, but alternatively, the leaves are longer or smaller or rounder. These effects may lead to more healthy plants. Alternatively, this trait attributes aesthetic properties to the plant such as greenness and stronger leafs.

"cycle time" of the plant as used herein means the time wherein a plant reaches 90% of its maximum total area. This parameter is an indication of the duration of the vegetative growth. Prolonged vegetative growth was only displayed in some of the plants according to the present invention and may be controlled by choice of the transformation event and/or by choice of the promoter driving the 2×C2H2 nucleic acid. For example this characteristic was not displayed when a seed-preferred promoter was used.

Other "growth characteristics" that may be improved by the methods of the present invention are growth rate, early vigour, modified Tmid, T90 or A42 or altered growth curve.

It is clear from the data as presented in the examples that one or more of the growth characteristics as defined herein above, may be combined in one plant. Alternatively, depending on the chosen transformation event and/or depending on the promoter used, one or more of these growth characteristics may be present or absent or more or less pronounced in the plant.

The methods of the present invention may also be used to confer stress tolerance to plants. In particular, a 2×C2H2 of the STZ type may be used to confer to a plant salt stress tolerance and/or drought stress tolerance. According to a specific embodiment, a tissue preferred promoter, such as a seed-preferred promoter" is used in these methods.

The present invention also relates to use of a nucleic acid sequence encoding a zinc finger protein and homologues, derivatives and active fragments thereof in modifying the growth characteristics of plants, preferably in increasing yield, further preferably increasing seed yield. The present invention also relates to use of a nucleic acid sequence encoding a 2×C2H2 zinc finger protein and homologues, derivatives and active fragments thereof and to the 2×C2H2 zinc finger protein itself and to homologues, derivatives and active fragments thereof as a growth regulator. The sequences represented by SEQ ID NO 1, and portions thereof and SEQ ID NO 2, and homologues, derivatives and active fragments thereof are useful in modifying the growth characteristics of plants, as hereinbefore described. The sequences would therefore find use as growth regulators, such as herbicides or growth stimulators. The present invention also provides a composition comprising a protein represented by SEQ ID NO 2, or a homologue, derivative or active fragment thereof for the use as a growth regulator. A growth regulator is used herein as meaning a regulator that increased yield and is therefore also referred to as yield regulator.

In particular, the present invention provides a yield regulating composition comprising a nucleic acid encoding a 2×C2H2 protein, and/or comprising a 2×C2H2 protein, and/or comprising a construct as defined herein above. Such a yield regulating composition further comprises additives normally use in yield regulating compositions, such as a solvent or carrier.

Conversely, the sequences according to the present invention may also be interesting targets for agrochemical compounds, such as herbicides or growth stimulators. Accordingly, the present invention encompasses use of a nucleic acid encoding a 2×C2H2 protein, of a 2×C2H2 protein and/or of a construct as defined in any of claims 20 to 22 as target for an agrochemical, such as a herbicide or a growth stimulator.

The methods according to the present invention may also be practised by co-expression of a gene encoding a 2×C2H2 zinc finger protein in a plant with at least one other gene that cooperates with the gene encoding a 2×C2H2 zinc finger protein. Such a gene may be a gene encoding a target protein of the 2×C2H2 zinc finger protein. Co-expression may be effected by cloning the genes under the control of a plant expressible promoter in a plant expressible vector and introducing the expression vector(s) into a plant cell using *Agrobacterium*-mediated plant transformation. Therefore, the methods according to the present invention may result in plants having modified growth characteristics, particularly increased yield, as described hereinbefore in combination with other economically advantageous traits, such as further yield-enhancing traits, tolerance to various stresses, traits modifying various architectural features and/or biochemical and/or physiological features.

Since the plants of the present invention have excellent growth characteristics and have high yield, they are suitable for the production of enzymes, pharmaceuticals or agrochemicals. Also, there are suitable to produce food or feed products.

The invention clearly extends to enzymes, pharmaceuticals or agrochemicals as well as food or feed products isolated from these plants.

Further a nucleic acid encoding a 2×C2H2 protein, a 2×C2H2 protein and/or the constructs of the present invention may be used breeding programs aiming at the development of plants with increased yield.

Particularly, the use of allelic variants as defined above in particular conventional breeding programmes, such as in marker-assisted breeding is also encompassed by the present invention; this may be in addition to their use in the methods according to the present invention. Such breeding programmes sometimes require the introduction of allelic variations in the plants by mutagenic treatment of a plant One suitable mutagenic method is EMS mutagenesis. Identification of allelic variants then takes place by, for example, PCR. This is followed by a selection step for selection of superior allelic variants of the sequence in question and which give rise to altered growth characteristics in a plant. Selection is typically carried out by monitoring growth performance of plants containing different allelic variants of the sequence in question, for example, SEQ ID NO 1. Monitoring growth performance may be done in a greenhouse or in the field. Further optional steps include crossing plants in which the superior allelic variant was identified with another plant. This could be used, for example, to make a combination of interesting phenotypic features According to another type of breeding programme a DNA marker is identified which may be genetically linked to a gene capable of modifying expression of a nucleic acid encoding a 2×C2H2 zinc finger protein in a plant, which gene may be a gene encoding the 2×C2H2 zinc finger protein itself or any other gene which may directly or indirectly influence expression of the gene encoding a 2×C2H2 zinc finger protein and/or activity of the 2×C2H2 zinc finger protein itself. This DNA marker may then be used in breeding programs to select plants having altered growth characteristics.

The methods according to the present invention may also be practised by introducing into a plant at least a part of a (natural or artificial) chromosome (such as a Bacterial Artificial Chromosome (BAC)), which chromosome contains at least a gene encoding a 2×C2H2 zinc finger protein, optionally together with one or more related gene family members. Therefore, according to a further aspect of the present invention, there is provided a method for modifying growth characteristics of plants by expressing in a plant at least a part of a chromosome comprising at least a gene encoding a 2×C2H2 zinc finger protein.

BRIEF DESCRIPTION OF THE DRAWINGS

The present invention will now be described with reference to the following figures in which:

FIG. 3 lists sequences useful in the methods of the present invention. SEQ ID NO: 1is an STZ encoding nucleic acid isolated from *Arabidopsis thaliana*; the start and the stop codon are highlighted in bold. SEQ ID NO: 2 is the STZ protein sequence encoded by SEQ ID NO: 1. In the STZ protein the nuclear localization signal also called the KRS motif or B-box is annotated (bold, italics, underlined), as well as the L-box (bold, underlined), the EAR motif (bold, italics), and the two C2H2 zinc finger domains with QALGGH (SEQ ID NO:5) motif (bold and boxed). SEQ ID NO: 10 to SEQ ID NO: 25 provides the sequences of various orthologs of the *Arabidopsis thaliana* STZ protein from other plant species. SEQ ID NO: 26 to SEQ ID NO: 35 provides the sequences of various paralogs (from *Arabidopsis*) of the STZ protein. SEQ ID NO 36 to SEQ ID NO: 50 provides the sequences of related 2×C2H2 genes and proteins useful in the methods of the present invention.

The zinc finger protein expression cassette has a WSI18 (PRO0151) promoter and a double terminator sequence (T-zein and T-rbcS-deltaGA) located within the left border (LB repeat) and the right border (RB repeat) of the Ti plasmid. Cloned within these T-borders are also a screenable marker and a selectable marker, each under the control of a constitutive promoter (Prom), followed by a terminator sequence (poly a and t-NOS). Furthermore, this vector also contains an origin of replication (pBR322 (ori+bom)) for bacterial replication and a selectable marker (Sm/SpR) for bacterial selection.

EXAMPLES

The present invention will now be described with reference to the following examples, which are by way of illustration alone.

DNA Manipulation

Unless otherwise stated, recombinant DNA techniques are performed according to standard protocols described in Sambrook (2001) Molecular Cloning: a laboratory manual, 3rd Edition Cold Spring Harbor Laboratory Press, CSH, New York or in Volumes 1 and 2 of Ausubel et al. (1988), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning

A gene encoding an STZ protein was amplified by PCR from an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was of $1.59\times10^7$ cfu. Original titer was determined to be $9.6\times10^5$ cfu/ml, after first amplification of $6\times10^{11}$ cfu/ml. After plasmid extraction, 200 ng of template was used in a 50 μl PCR mix. Sequences of the primers used for PCR amplification were, including the attB sites for Gateway recombination (in bold) were PRM3204 (sense, start codon in italics) 5' GGGGACAAGTTTGTACAAAAAAGCAGGCTTCACAATGGCG CTCGAGGCTC 3' (SEQ ID NO 3) and PRM3205 (reverse, complementary stop codon in italics) 5' GGGGACCACTTTGTACAAGAAAGCTGGGTAATTTCCTTAAAGTTGAAGTTTGA 3' (SEQ ID NO 4).

PCR was performed using Hifi Taq DNA polymerase in standard conditions. The PCR fragment (CDS1536) was amplified and purified using standard methods. The first step of the Gateway procedure, the BP reaction, was then performed, during which the PCR fragment was recombined in vivo with the pDONR plasmid to produce, according to Gateway terminology, an "entry clone", p3359. PDONR was purchased from Invitrogen, as part of the Gateway technology.

Example 2

Vector Construction for Rice Transformation with pGOS2::AtSTZ

Figure 1:
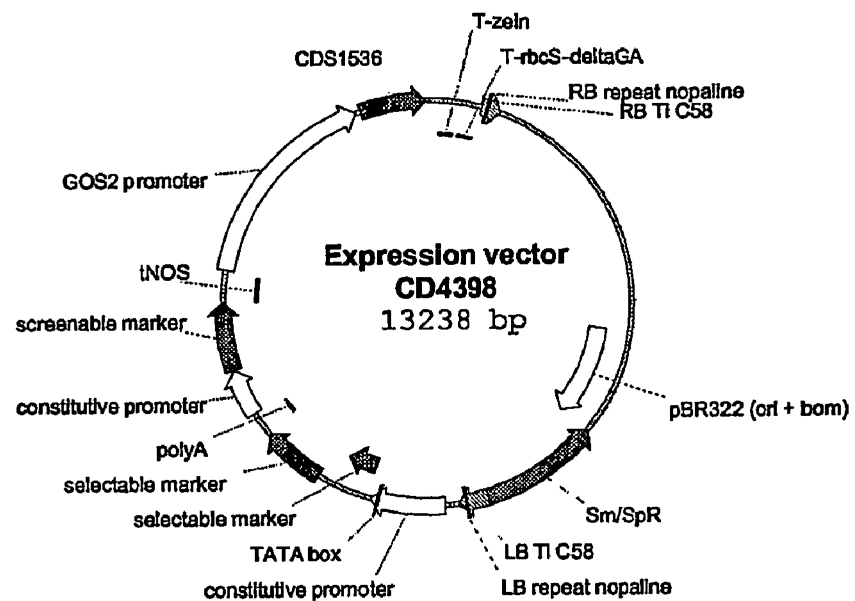
FIG. 1 is a map of an expression vector for the expression in plants of a 2×C2H2zinc finger protein under the control of a GOS2 promoter. CDS1536 is the internal code for the *Arabidopsis thaliana* salt tolerant zinc finger (STZ) protein cDNA. The zinc finger protein expression cassette has a GOS2 promoter and a double terminator sequence (T-zein and T-rbcS-deltaGA) located within the left border (LB repeat) and the right border (RB repeat) of the Ti plasmid. Cloned within these T-borders are also a screenable marker and a selectable marker, each under the control of a constitutive promoter (Prom), followed by a terminator sequence (poly a and t-NOS). Furthermore, this vector also contains an origin of replication (pBR322 (ori+bom)) for bacterial replication and a selectable marker (Sm/SpR) for bacterial selection.

The entry done p3359 was subsequently used in an LR reaction with p0640, a destination vector used for rice transformation. This vector contains as functional elements within the T-DNA borders a plant selectable marker and a Gateway cassette intended for LR in vivo recombination with the sequence of interest already cloned in the donor vector. Upstream of this Gateway cassette lies the rice GOS2 promoter for constitutive expression of the zinc finger gene (De Pater et al., Plant J. 2 (6) 837-844, 1992). After the recombination step, the resulting expression vector with the expression cassette CD4398 (FIG. 1) was transformed into *Agrobacterium* strain LBA4404 and subsequently into plants. Transformed rice plants were allowed to grow and then examined for various parameters as described in Example 3.

Example 3

Evaluation of T0, T1 and T2 Transgenic Rice Plants Transformed with pGOS2::AtSTZ (CD4398)

Approximately 15 to 20 independent T0 transformants were generated. The primary T0 transformants were transferred from tissue culture chambers to a greenhouse for growing and harvest of T1 seed. Six events of which the T1 progeny segregated 3:1 for presence/absence of the transgene were retained. For each of these events, approximately 10 T1 seedlings containing the transgene (hetero- and homo-zygotes), and approximately 10 T1 seedlings lacking the transgene (nullizygotes), were selected by PCR. Based on the results of the T1 evaluation three events were chosen, for further characterisation in the T2 generation, one event being very positive for a number of parameters, a second event being positive for a number of parameters, but less pronounced, and a third event being neutral. Seed batches from the positive plants (both hetero- and homozygotes) in T1, were screened by monitoring marker expression. For each chosen event, the heterozygote seed batches were then selected for T2 evaluation. An equal number of positives and negatives within each seed batch were transplanted for evaluation in the greenhouse (i.e., for each event 40 plants were grown of which there were about 20 positives for the transgene and about 20 negative). Therefore, the total number for the three events amounted to 120 plants for evaluation in the T2 generation.

T1 and T2 plants were transferred to the greenhouse and evaluated for vegetative growth parameters and seed parameters, as described hereunder.

(I) Statistical Analysis of Phenotypic Characteristics

A two factor ANOVA (analyses of variance) was used as statistical model for the overall evaluation of plant phenotypic characteristics. An F-test was carried out on all the parameters measured, for all the plants of all the events transformed with the gene of interest The F-test was carried out to check for an effect of the gene over all the transformation events and to verify an overall effect of the gene or "global gene effect". Significant data, as determined by the value of the f-test, indicates a "gene" effect, meaning that the phenotype observed is caused by more than the presence or position of the gene. In case of the F-test, the threshold for significance for a global gene effect is set at 5% probability level.

To check for an effect of the genes within an event, i.e., for a line-specific effect, a t-test was performed within each event using data sets from the transgenic plants and the corresponding null plants. "Null plants" or "Null segregants" are the plants treated in the same way as the transgenic plant, but from which the transgene has segregated. Null plants can also be described as homozygous negative transformant plants. The threshold for significance for the t-test is set at 10% probability level. Within one population of transformation events, some events may be under or above this t-test threshold. This is based on the hypothesis that a gene might only have an effect in certain positions in the genome, and that the occurrence of this position-dependent effect is not uncommon. This kind of gene effect may also be referred to as a "line effect of a gene". The p-value is obtained by comparing the t-value to the t-distribution or alternatively, by comparing the F-value to the f-distribution. The p-value stand for the probability that the null hypothesis (null hypothesis being "there is no effect of the transgene") is correct.

(II) Vegetative Growth Measurements

Figure 2:
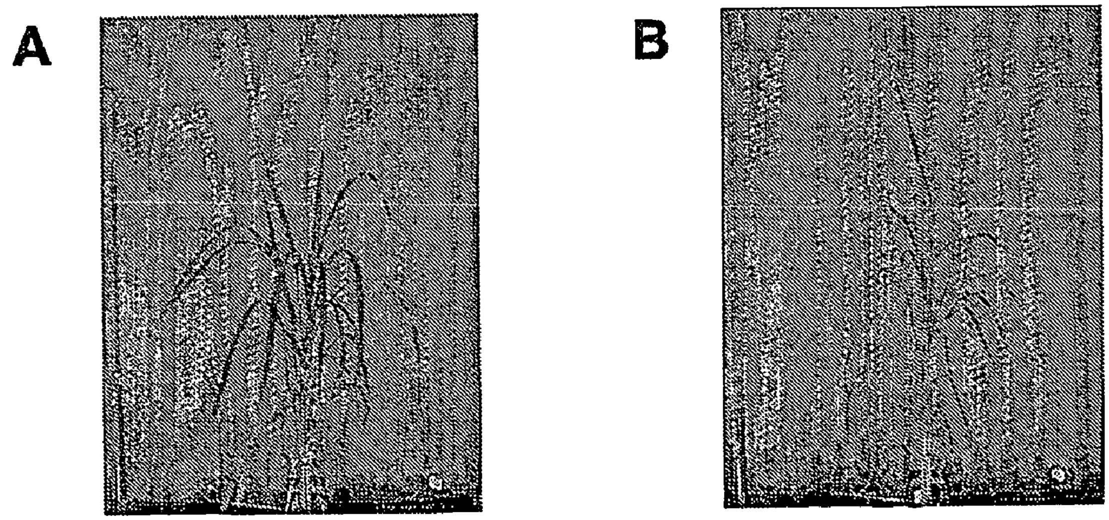
FIG. 2A shows digital images from a T1 positive line transformed with an STZ zinc finger transgene under control of a GOS2 promoter and FIG. 2B shows digital images of corresponding nullizygotes plants.

The selected plants were grown in a greenhouse. Each plant received a unique barcode label to link unambiguously the phenotyping data to the corresponding plant. The selected plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity (which is the stage were there is no more increase in biomass) the plants were passed weekly through a digital imaging cabinet (examples of pictures are shown in FIGS. 2A and 2B). At each time point digital images (2048×1536 pixels, 16 million colours) were taken of each plant from at least 6 different angles. The parameters described below were derived in an automated way from the digital images using image analysis software.

(a) Aboveground Area

Plant above ground area was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground.

Results of the maximum above ground area values of the lines selected for T2 evaluation are summarized in Table 1. The plants of the best performing line showed an increase in biomass of 34%, compared to the nullizygotes.

Figure 4:
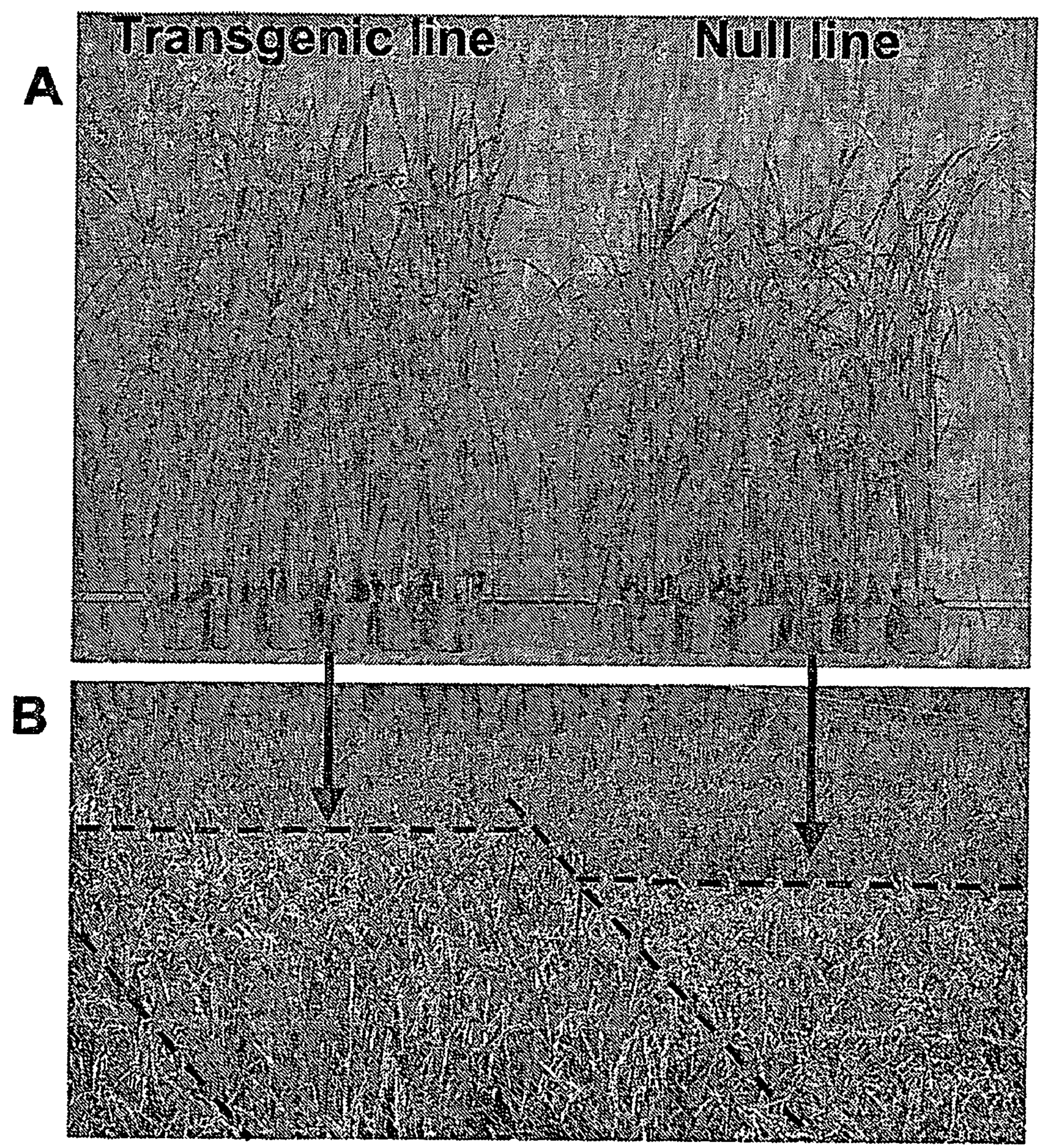
FIG. 4 is a photograph of T3 plants grown in a greenhouse (A) or in a field (B). The photograph shows yield increase (especially in aboveground biomass and plant height) in subsequent generations of STZ transformed plants.

When an F-test was carried out on all the plants of all the T2 events it became clear that the transgenic plants show a significant increase in above ground area, in average an increase of approximately 18%. A significant increase in above ground biomass is also displayed by STZ transformed plants grown under field conditions (see FIG. 4).

TABLE 1

Aboveground area of STZ transgenic T2 plants. Each row corresponds to one event, for which the average maximum aboveground area (expressed in $mm^2$) was determined for the transgenics (TR) and the null plants (null). The difference in absolute values between the transgenic population and the nullizygotes of each event are presented (dif.) as well as the percentage of difference between the two populations (% dif). P stands for the probability produced by the t-test for each event. The last row presents the average numbers calculated from all the events. Here the p-value is produced by the F-test.

Total above ground Area Max ($mm^2$)

| Line | TR | null | dif | % dif | p-value |
|---|---|---|---|---|---|
| CD4396 L1 | 63947 | 47606 | 16341 | 34 | 0.0021 |
| CD4396 L2 | 42509 | 41342 | 1167 | 3 | 0.8063 |
| CD4396 L3 | 41116 | 33687 | 7429 | 22 | 0.1107 |
| Overall | 49178 | 41657 | 7522 | 18 | 0.0047 |

(b) Plant Height Measurements

Plant height was determined by the distance between the horizontal lines going through the upper pot edge and the uppermost pixel corresponding to a plant part above ground. This value was averaged for the pictures taken on the same time point from the different angles and was converted, by calibration, to a physical distance expressed in mm. Experiments showed that plant height measured this way correlate with plant height measured manually with a ruler.

The increase in plant height was displayed very clearly in STZ transformed plants when measured at the end of the vegetative growth (see FIG. 4A). Also, this parameter, was displayed by STZ transformed plants when grown in the field (see FIG. 4B) at the time of harvest.

(c) Total Area Cycle Time Measurements

Plants were imaged weekly along the complete cell cycle and the maximum total area of the plants was determined as mentioned above. Total Area Cycle Time is the time when a plant reaches 90% of its maximum total area. This parameter is an indication of the duration of the vegetative growth.

Only in some transgenic lines there was an effect on cycle time. These few lines showed a prolonged vegetative growth.

(III) Measurement of Seed-related Parameters

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of seed-related parameters described below.

(a) Total Number of Filled Seeds Per Plant

The number of filled seeds was determined by counting the number of filled husks that remained after the separation step.

Total numbers of filled seeds per plant are summarized in Table 2. The t-test shows that for two events, transgenic plants produce 106% and 130% more filled seeds than the nullizygotes.

TABLE 2

Number of filled seeds of STZ transgenic T2 plants. Each row corresponds to one event, for which the average number of filled seeds was determined for the transgenics (TR) and the null plants (null). The difference in absolute values between the transgenic population and the nullizygotes of each event are presented (dif.) as well as the percentage of difference between the two populations (% dif). P stands for the probability produced by the t-test for each event. The last row presents the average numbers calculated from all the events. Here the p-value is produced by the F-test.

Number of filled seeds

| Line | TR | null | dif | % dif | p-value |
|---|---|---|---|---|---|
| CD4396 L1 | 387.9 | 188.7 | 199.19 | 106 | <0.0001 |
| CD4396 L2 | 163.8 | 156.5 | 7.22 | 5 | 0.8382 |
| CD4396 L3 | 236.9 | 102.9 | 133.98 | 130 | 0.0004 |
| Overall | 264.9 | 159.7 | 105.25 | 66 | <0.0001 |

(b) Total Seed Weight Per Plant

The total seed weight was measured by weighing all filled husks harvested from a plant.

The total seed weight values of STZ transformed plants are summarized in Table 3. STZ transgenic plants produce significantly more seed weight than the corresponding nullizygotes. The difference in seed weight of the transgenics may be as high as 138% or higher.

TABLE 3

Total seed weight per plant of STZ transgenic T2 plants. Each row corresponds to one event, for which the average total seed weigh (in gram) was determined for the transgenics (TR) and the null plants (null). The difference in absolute values between the transgenic population and the nullizygotes of each event are presented (dif.) as well as the percentage of difference between the two populations (% dif). P stands for the probability produced by the t-test for each event. The last row presents the average numbers calculated from all the events. Here the p-value is produced by the F-test.

Total weight of seeds

| Line | TR | null | dif | % dif | p-value |
|---|---|---|---|---|---|
| CD4396 L1 | 9.8 | 4.5 | 5.25 | 116 | <0.0001 |
| CD4396 L2 | 3.4 | 3.3 | 0.1 | 3 | 0.908 |
| CD4396 L3 | 6.1 | 2.6 | 3.56 | 138 | 0.0001 |
| Overall | 6.5 | 3.7 | 2.75 | 74 | <0.0001 |

(c) Harvest Index

The harvest index in the present invention is defined as the ratio between the total seed yield and the above ground area ($mm^2$), multiplied by a factor $10^6$.

The harvest index values of the STZ-transgenic plants are summarized in Table 4. STZ transgenic plants have a significant increase in harvest index. The increase in harvest index of the transgenic plants may be as high as 66%, when compared to the corresponding nullizygotes.

TABLE 4

Harvest index of STZ transgenic T2 plants. Each row corresponds to one event, for which the average harvest index was determined for the transgenics (TR) and the null plants (null). The difference in absolute values between the transgenic population and the nullizygotes of each event are presented (dif.) as well as the percentage of difference between the two populations (% dif). P stands for the probability produced by the t-test for each event. The last row presents the average numbers calculated from all the events. Here the p-value is produced by the F-test.

Harvest Index

| Line | TR | null | dif | % dif | p-value |
|---|---|---|---|---|---|
| CD4396 L1 | 149.1 | 90 | 59.11 | 66 | <0.0001 |
| CD4396 L2 | 74 | 73.4 | 0.55 | 1 | 0.9574 |
| CD4396 L3 | 121.3 | 75.9 | 45.32 | 60 | <0.0001 |
| Overall | 114.8 | 82.6 | 32.16 | 39 | <0.0001 |

(d) Thousand Kernel Weigth (TKW) of Plants

Thousand Kernel Weight (TKW) is a parameter extrapolated from the number of filled seeds counted, and their total weight.

The weight values of thousand kernels of STZ transgenic plants are presented in Table 5. STZ transgenic plants have increased thousand kernel weight. The increase of TKW of transgenic plants may be as high as 6% when compared to the corresponding nullizygotes.

TABLE 5

Thousand kernel weight of STZ transgenic T2 plants. Each row corresponds to one event, for which the average TKW was determined for the transgenics (TR) and the null plants (null). The difference in absolute values between the transgenic population and the nullizygotes of each event are presented (dif.) as well as the percentage of difference between the two populations (% dif). P stands for the probability produced by the t-test for each event. The last row presents the average numbers calculated from all the events. Here the p-value is produced by the F-test.

TKW

| Line | TR | null | dif | % dif | p-value |
|---|---|---|---|---|---|
| CD4396 L1 | 25.2 | 23.8 | 1.46 | 6 | 0.0128 |
| CD4396 L2 | 20.6 | 20.7 | −0.14 | −1 | 0.7963 |
| CD4396 L3 | 25.5 | 24.5 | 0.99 | 4 | 0.0812 |
| Overall | 23.7 | 23 | 0.71 | 3 | 0.0213 |

(e) Total Number of Seeds

The total number of seeds per plant was measured by counting the number of husks harvested from a plant.

The total numbers of seeds per plant are summarized in Table 6. STZ transformed plants have an increase in total number of seeds. The increase of total number of seeds may be as high as 68%, when compared to the corresponding nullizygotes.

TABLE 6

Total number of seeds of STZ transgenic T2 plants. Each row corresponds to one event, for which the average total number of seeds was determined for the transgenics (TR) and the null plants (null). The difference in absolute values between the transgenic population and the nullizygotes of each event are presented (dif.) as well as the percentage of difference between the two populations (% dif). P stands for the probability produced by the t-test for each event. The last row presents the average numbers calculated from all the events. Here the p-value is produced by the F-test.

Total number of seeds

| Line | TR | null | dif | % dif | p-value |
|---|---|---|---|---|---|
| CD4396 L1 | 483.5 | 367.4 | 116.03 | 32 | 0.0146 |
| CD4396 L2 | 353.9 | 327.5 | 26.42 | 8 | 0.5473 |
| CD4396 L3 | 383.6 | 228.2 | 155.48 | 68 | 0.0009 |
| Overall | 406 | 312.5 | 93.52 | 30 | 0.0002 |

Conclusion

It may be concluded that vegetative growth is increased in the STZ transgenic plants when compared to the control non-transgenic plants, as reflected by parameters such as above ground area, where the increase is above 20%. This effect may be attributed to the expression of the STZ gene in the transgenic plants. Additionally, in some transformation events, the length of the vegetative growth is altered in the STZ transgenic plants. For those transformation events in which this effect occurs, in average the vegetative growth was prolonged with about 4 to 6 days, under the conditions tested.

Furthermore, yield was increased in STZ transgenic plants. Several seed parameters reflect this yield increase. The total number of seeds harvested was at least 100% higher in the transgenics than in the control plants, for those events showing a differential. For these events, there was also an increase in the total number of seeds of the transgenics, which increase was higher than 30%. Seed filling in those transgenics was greatly improved, reaching differences above 100% in the number of filled seeds.

Seed of the transgenic plants were also heavier, and probably bigger, as suggested by the higher values obtained for the thousand kernel weigh. The TKW parameter is a very stable parameter in rice cultivars, such as nipponbare, and in the growth conditions here used. This means that this parameter is not easily influenced and makes it an important yield parameter. Therefore a TKW increase of 6% represents a significantly increase in yield.

Harvest index, another important yield parameter, was increased in the transgenic plants with more than 50%.

In summary, based on the evaluation of STZ transgenic plants in the T1, T2 and further generations, it may be concluded that the presence of an STZ transgene, has a positive effect on the size of the plant and/or its organs, as well as a positive effect on the final yield harvested.

(III) Root Growth Measurements

Transgenic plants are grown next to their corresponding non-transgenic null segregant in transparent pots. In average, for each construct comprising a particular promoter-2×C2H2 combination, a minimum of 5 independent transformation events are evaluated for root growth, root development and root architecture. Typically, per transformation event, 10 transgenics are compared to 10 nullizygotes. Root pictures are taken weekly during plant growth. The pictures are processed and analyzed to extract the values for the root parametes as detailed below. Statistical analysis as described above are applied to these data.

a) Root Area

Total root area is calculated from the summed number of pixels of each root images. A positive linear correlation between root area and dry weight and root biomass of the root has been previously established by similar experiments. Therefore, root area is a good approximation for mot biomass.

b) Root Length

The total perimeter of the roots of a plant is calculated as the sum of the perimeter of all roots in the images. A linear correlation between this measurement and root length has been previously established. Thus, root length is extrapolated from the total root perimeter.

c) Root Width

Average root width of a plant is expressed as the ratio between the Root Area and the Root Length.

STZ transgenic plants of the invention show a superior performance when compared to control pants. Transgenic plants are altered in one or more the root parameters detailed above. In particular the transgenic have increased root biomass, for example due to increased root dry weight or area, and/or increased root length and/or increased root width.

Example 4

Leaf Blade Width Measurement

Leaves of STZ transgenic plants appeared bigger and wider when compared to the corresponding control non-transgenic plants. To quantify the increase in leaf width, leaf blade width (length of transversal axe) of the flag leaf was measured with a ruler at the widest point of the leaf, which is approximately at half of the length, in plants that have reached the end of the vegetative growth phase. The results shown in the Table 7, indicate that the increase in the leaf blade width in at least the event here measured was around 15% when compared to the corresponding nullizygote.

TABLE 7

Leaf blade width of STZ transgenic T2 plants. The average leaf blade width was determined for the transgenics (TR) and the null plants (null) of the selected event. The difference in absolute values between the transgenic population and the nullizygotes of the event is presented (dif.) as well as the percentage of difference between the two populations (% dif). P stands for the probability produced by the t-test.

Leaf blade width

| Line | TR | null | dif | % dif | p-value |
|---|---|---|---|---|---|
| CD4396 L1 | 1.56 | 1.35 | 0.21 | 15 | 0.098 |

Example 5

Vector Construction for Rice Transformation with pWSI18::AtSTZ

Figure 5:
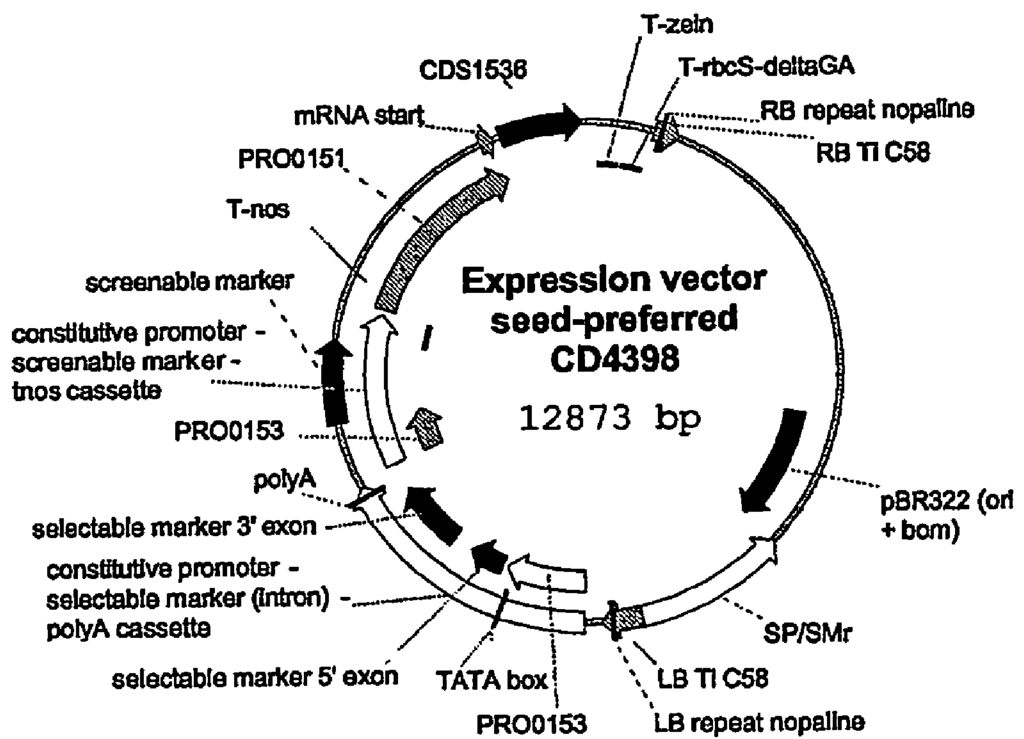
FIG. 5 shows the binary vector for expression in *Oryza sativa* of the *Arabidopsis thaliana* STZ gene (CDS1536) under the control of a seed preferred WS118 promoter (PRO0151). This vector contains a T-DNA derived from the Ti Plasmid, limited by a left border (LB repeat, LB Ti C58) and a right border (RB repeat, RB Ti C58)).

Vector construction for transformation with the pWSI18 (PRO0151)-AtSTZ (CDS1536) cassette was carried out essentially as in example 2. The entry clone p3359, described earlier, was subsequently used in an LR reaction with p05653, a destination vector used for rice transformation. This destination vector contains as functional elements within the T-DNA borders a plant selectable marker and a Gateway cassette intended for LR in vivo recombination with the sequence of interest already cloned in the donor vector. A WSI18 promoter for seed preferred expression (PRO0151) is located upstream of this Gateway cassette. After the recombination step, the resulting expression vector with the expression cassette CD4398 (FIG. 5) was transformed into *Agrobacterium* strain LBA4404 and subsequently this vector was transformed to *Oryza sativa* plants. Transformed rice plants were allowed to grow and then examined for various parameters as described in example 3.

Example 6

Evaluation of T0 and T1 Transgenic Rice Plants Transformed with the Seed Preferred Expression Cassette pWSI18::AtSTZ (CD4398)

Preparations of calli and of the *Agrobacterium tumefaciens* strain containing the expression vector with the CD4398 expression cassette, were carried out as described in example 3, as were the calli transformation and plant regeneration.

Approximately 15 to 20 independent T0 rice transformants were generated. The primary transformants were transferred from tissue culture chambers to a greenhouse for growing and harvest of T1 seed. Events, of which the T1 progeny segregated 3:1 for presence/absence of the transgene, were retained. For each of these events, approximately 10 T1 seedlings containing the transgene (hetero- and homo-zygotes), and approximately 10 T1 seedlings lacking the transgene (nullizygotes), were selected by monitoring marker expression. Transgenic plantlets were grown next to control nullyzygotes, seeds were harvested and thousand kernel weight determined as previously described.

Transformed plants comprising the expression cassette CD8490 (seed preferred pWSI18::STZ), had a normal and healthy appearance and were harvested at the same time as the control plants. The seeds harvested from the transgenic plants had an increase in thousand kernel weight when compared to the control plants. As shown in Table 8 increase in thousand kernel weight was above 10%.

TABLE 8

Thousand kernel weight of STZ transgenic T1 plants. The average I thousand kernel weight was determined for the transgenics (TR) and the null plants (null) of the selected event. The difference in absolute values between the transgenic population and the nullizygotes of the event is presented (dif.) as well as the percentage of difference between the two populations (% dif). P stands for the probability produced by the t-test.

Thousand kernel weight

| Line | TR | null | dif | % dif | p-value |
|---|---|---|---|---|---|
| CD8490 L1 | 29.6 | 26.8 | 2.82 | 11 | 0.001 |

Example 7

Cloning, Transformation and Evaluation of Other 2×C2H2 Encoding Genes

In Table 9 an overview is given of constructs with STZ or other 2×C2H2 zinc finger proteins, under control of various promoters, which constructs are made for use in the methods of the present invention. The coding regions of the 2×C2H2 genes to be cloned (GOI, Gene of Interest) are amplified by PCR from cDNA, following the protocol as in Example 1. Specific primers for each 2×C2H2 gene were designed at the start and stop codons of the gene sequence as present in the public database under the accession number as indicated in Table 9. These cloned sequences are also herein incorporated under the SEQ ID NO number as mentioned in the table. Moreover, the isolated PCR fragments were also given a unique CDS number.

The PCR fragment with a 2×C2H2 gene is then cloned under the control of a particular promoter. Different combinations for different genes are made (see Table 9). Chimeric constructs are made and CD numbers represent bacterial strains carrying the chimeric construct Corresponding transgenic plants are obtained by transforming the plants with the chimeric constructs, following the protocols as mentioned herein before. Evaluation of the transgenic events reveals an increase in yield, and increase in leaf surface area and/or an increase in duration of vegetative growth in the transgenic plants when compared to the control non-transgenic plants.

TABLE 9 examples of 2xC2H2 chimeric constructs useful for the methods of the present invention. *see Table 10

| CDS | Accession number (cDNA on which primers were designed to amplify the CDS region) | Prot ACC number | SEQ ID NO | PRO0129* | PRO0170* | PRO0081_2* |
|---|---|---|---|---|---|---|
| CDS1536 STZ *Arabidopsis* | X95573 | CAA64820 | 1 + 2 | CD4398 | CD11371 | CD11382 |
| CDS2200 Paralog *Arabidopsis* | AF022658 NM_120516 | AAB80922.1 At5g04340 | 28 + 29 | CD11576 | | |
| CDS2205 Paralog *Arabidopsis* | NM_123683 | At5g43170 | 32 + 33 | CD11325 | | |
| CDS2775 Ortholog *Oryza sativa* | AF332876 | AAK01713.1 | 36 + 37 | CD09948 | | |
| CDS1677 Homolog *Arabidopsis* | AL132966 REGION: 116202 . . . 116729 | CAB67667 | 38 + 39 | CD06462 | | |
| CDS3337 Homolog Sugarcane | CA279020 | | 40 | CD | | |
| CDS2416 Homolog *Arabidopsis* | AF254447 | At3g57670 | 41 + 42 | CD | | |
| CDS2377 Homolog *Arabidopsis* | AJ311810 | CAC86167 | 43 + 44 | CD | | |
| CDS Homolog *Arabidopsis* | AL355775 REGION: complement (7957 . . . 8451) | CAB90935 | 45 + 46 | CD | | |
| CDS Homolog *Arabidopsis* | AL391143 REGION: complement (31730 . . . 32938) | CAC01747 | 47 + 48 | CD | | |
| CDS3641 Homolog *Arabidopsis* | X98678 | CAA67236 | 49 + 50 | CD | | |

| CDS | PRO0123* | PRO0207* | PRO0110* | PRO0090* | PRO0151* | PRO0218* |
|---|---|---|---|---|---|---|
| CDS1536 STZ Arabidopsis | CD10960 | CD10959 | CD10313 | CD11370 | CD06490 | |
| CDS2200 Paralog *Arabidopsis* | CD11413 | | CD11543 | CD11522 | CD8294 | CD11305 |
| CDS2205 Paralog *Arabidopsis* | CD11414 | | CD11381 | CD11327 | CD9843 | CD11325 |
| CDS2775 Ortholog *Oryza sativa* | | | CD10315 | CD11320 | CD09995 | CD11821 |
| CDS1677 Homolog *Arabidopsis* | CD | | CD | CD | | |
| CDS3337 Homolog Sugarcane | CD | | CD | CD | | |
| CDS2416 Homolog *Arabidopsis* | CD | | CD | CD | | |
| CDS2377 Homolog *Arabidopsis* | CD | | CD | CD | | |
| CDS Homolog *Arabidopsis* | CD | | CD | CD | | |
| CDS Homolog *Arabidopsis* | CD | | CD | CD | | |
| CDS3641 Homolog *Arabidopsis* | CD | | CD | CD | | |

TABLE 10 examples promoters used in combination with 2xC2H2 for the methods of the present invention.

| Promoter | Preferred expression type | Origin species | Gene |
|---|---|---|---|
| PRO0151 | Seeds (mainly embryo and aleurone). Strong expression. | *Oryza sativa* | WSI18 |
| PRO0110 | Root | *Oryza sativa* | RCc3 |
| PRO0207 | Green tissue. Moderate expresssion levels | *Saccharum officinarum* | Prp |
| PRO0123 | Green tissue. Strong expression levels. | *Oryza sativa* | Protochlorophyllide reductase |
| PRO0090 | Seed specific (mainly endosperm) | *Oryza sativa* | Prolamin RP6 |

TABLE 10-continued examples promoters used in combination with 2xC2H2 for the methods of the present invention.

| Promoter | Preferred expression type | Origin species | Gene |
|---|---|---|---|
| PRO0170 | Constitutive. Strong Expression. | *Oryza sativa* | High Mobility Group protein |
| PRO0218 | Seeds (mainly embryo and aleurone) | *Oryza sativa* | oleosine 18 kda |
| PRO0061_2 | Young expanding tissues | *Oryza sativa* | beta-expansine EXPB9 |
| PRO0129 | Constitutive. High expression levels. | *Oryza sativa* | GOS2 |

Example 8

Use of the Invention in Corn

The methods of the invention described herein are also used in maize. To this aim, an STZ encoding gene, for example a maize or other STZ ortholog, is cloned under control of a promoter operable in maize, in a plant transformation vector suitable for *Agrobacterium*-mediated corn transformation. Methods to use for corn transformation have been described in literature (Ishida et al., Nat Biotechnol. 1996 June; 14(6):745-50; Frame et al., Plant Physiol. 2002 May; 129(1):13-22).

Transgenic plants made by these methods are grown in the greenhouse for T1 seed production. Inheritability and copy number of the transgene are checked by quantitative real-time PCR and Southern blot analysis and expression levels of the transgene are determined by reverse PCR and Northern analysis. Transgenic lines with single copy insertions of the transgene and with varying levels of transgene expression are selected for T2 seed production.

Progeny seeds are germinated and grown in the greenhouse in conditions well adapted for maize (16:8 photoperiod, 26-28° C. daytime temperature and 22-24° C. nighttime temperature) as well under water-deficient, nitrogen-deficient, and excess NaCl conditions. Null segregants from the same parental line, as well as wild type plants of the same cultivar are used as controls. The progeny plants resulting from the selfing or the crosses are evaluated on different biomass and developmental parameters, including, plant height, stalk/stem thickness, stem size, number of leaves, total above ground area, leaf greenness, time to maturity, time to silking, flowering time, time to flower, ear number, ear length, row number, kernel number, kernel size, kernel oil content, grain maturity, harvesting time. The seeds of these lines are also checked on various parameters, such as grain size, total grain yield per plant, and grain quality (starch content, protein content and oil content).

Lines that are most significantly improved compared to corresponding control lines are selected for further field-testing and marker-assisted breeding, with the objective of transferring the field-validated transgenic traits into commercial germplasm. The testing of maize for growth and yield-related parameters in the field is conducted using well-established protocols. The corn plants are particularly evaluated on yield parameters, such as for example, amount of plants per acre, amount of ears per plant, amount of rows per ear, amount of seeds per row and TKW. Subsequent improvements for introgressing specific loci (such as transgene containing loci) from one germplasm into another is also conducted using well-established protocols.

The invention claimed is:

1. A method for increasing plant yield under conditions promoting plant growth relative to a corresponding wild type plant grown under said conditions, comprising transforming a plant with a nucleic acid sequence encoding a 2×C2H2 zinc finger protein, wherein said 2×C2H2 zinc finger protein is a dicotyledonous plant 2×C2H2 zinc finger protein and wherein said 2×C2H2 zinc finger protein is SEQ ID NO:2;

growing said plant under said conditions; and selecting a plant having increased yield as compared to a corresponding wild type plant.

2. A method for increasing leaf surface area under conditions promoting plant growth relative to a corresponding wild type plant grown under said conditions, comprising transforming a plant with a nucleic acid sequence encoding a 2×C2H2 zinc finger protein, wherein said 2×C2H2 zinc finger protein is a dicotyledonous plant 2×C2H2 zinc finger protein and wherein said 2×C2H2 zinc finger protein is SEQ ID NO:2;

growing said plant under said conditions; and selecting a plant having increased leaf surface area as compared to a corresponding wild type plant.

3. A method for prolonging vegetative growth phase of a plant under conditions promoting plant growth relative to a corresponding wild type plant grown under said conditions, comprising transforming a plant with a nucleic acid sequence encoding a 2×xC2H2 zinc finger protein, wherein said 2×C2H2 zinc finger protein is a dicotyledonous plant 2×C2H2 zinc finger protein and wherein said 2×C2H2 zinc finger protein is SEQ ID NO:2;

growing said plant under said conditions; and selecting a plant having prolonging vegetative growth phase as compared to a corresponding wild type plant.

4. The method according to claim 1, wherein said plant is a monocot.

5. The method according to claim 1, wherein said nucleic acid introduced into the plant is comprised on at least part of a chromosome.

6. The method according to claim 1, wherein expression of said nucleic acid is driven by a plant promoter.

7. The method according to claim 6, wherein the plant promoter is a tissue preferred promoter.

8. The method according to claim 1, wherein said increased yield comprises increased above ground biomass.

9. The method according to claim 1, wherein said increased yield comprises increased seed yield.

10. The method according to claim 1, wherein said increased yield comprises increased root yield.

11. A method for the production of a transgenic plant having increased yield, increased leaf surface area and/or prolonged vegetative growth under conditions promoting plant growth relative to a corresponding wild type plant grown under said conditions, which method comprises (i) introducing into a plant or plant cell a nucleic acid sequence encoding a 2×C2H2 zinc finger protein, wherein said 2×C2H2 zinc finger protein is SEQ ID NO:2

(ii) cultivating the plant or plant cell under conditions promoting plant growth; and (iii) selecting for plants having increased yield, increased leaf surface area and/or prolonged vegetative growth.

12. The method according to claim 6, wherein the plant promoter is a constitutive promoter.

13. The method of claim 12, wherein the promoter is a GOS2 promoter.

14. The method according to claim 7, wherein the tissue preferred promoter is a seed-preferred promoter.

* * * * *

SEQUENCE LISTING

```
<160> NUMBER OF SEQ ID NOS: 52

<210> SEQ ID NO 1
<211> LENGTH: 692
<212> TYPE: DNA
<213> ORGANISM: Arabidopsis thaliana

<400> SEQUENCE: 1

aatggcgctc gaggctctta catcaccaag attagcttct ccgattcctc ctttgttcga     60

agattcttca gtcttccatg gagtcgagca ctggacaaag ggtaagcgat ctaagagatc    120

aagatccgat ttccaccacc aaaacctcac tgaggaagag tatctagctt tttgcctcat    180

gcttctcgct cgcgacaacc gtcagcctcc tcctcctccg gcggtggaga agttgagcta    240

caagtgtagc gtctgcgaca agacgttctc ttcttaccaa gctctcggtg gtcacaaggc    300

aagccaccgt aagaacttat cacagactct ctccggcgga ggagatgatc attcaacctc    360

gtcggcgaca accacatccg ccgtgactac tggaagtggg aaatcacacg tttgcaccat    420

ctgtaacaag tctttttcctt ccggtcaagc tctcggcgga cacaagcggt gccactacga    480

aggaaacaac aacatcaaca ctagtagcgt gtccaactcc gaaggtgcgg ggtccactag    540
```

```
ccacgttagc agtagccacc gtgggtttga cctcaacatc cctccgatcc ctgaattctc    600

gatggtcaac ggagacgacg aagtcatgag ccctatgccg gcgaagaagc ctcggtttga    660

ctttccggtc aaacttcaac tttaaggaaa tt                                  692


<210> SEQ ID NO 2
<211> LENGTH: 227
<212> TYPE: PRT
<213> ORGANISM: Arabidopsis thaliana

<400> SEQUENCE: 2

Met Ala Leu Glu Ala Leu Thr Ser Pro Arg Leu Ala Ser Pro Ile Pro
1               5                   10                  15

Pro Leu Phe Glu Asp Ser Ser Val Phe His Gly Val Glu His Trp Thr
            20                  25                  30

Lys Gly Lys Arg Ser Lys Arg Ser Arg Ser Asp Phe His His Gln Asn
        35                  40                  45

Leu Thr Glu Glu Glu Tyr Leu Ala Phe Cys Leu Met Leu Leu Ala Arg
    50                  55                  60

Asp Asn Arg Gln Pro Pro Pro Pro Pro Ala Val Glu Lys Leu Ser Tyr
65                  70                  75                  80

Lys Cys Ser Val Cys Asp Lys Thr Phe Ser Ser Tyr Gln Ala Leu Gly
                85                  90                  95

Gly His Lys Ala Ser His Arg Lys Asn Leu Ser Gln Thr Leu Ser Gly
            100                 105                 110

Gly Gly Asp Asp His Ser Thr Ser Ser Ala Thr Thr Thr Ser Ala Val
        115                 120                 125

Thr Thr Gly Ser Gly Lys Ser His Val Cys Thr Ile Cys Asn Lys Ser
    130                 135                 140

Phe Pro Ser Gly Gln Ala Leu Gly Gly His Lys Arg Cys His Tyr Glu
145                 150                 155                 160

Gly Asn Asn Asn Ile Asn Thr Ser Ser Val Ser Asn Ser Glu Gly Ala
                165                 170                 175

Gly Ser Thr Ser His Val Ser Ser Ser His Arg Gly Phe Asp Leu Asn
            180                 185                 190

Ile Pro Pro Ile Pro Glu Phe Ser Met Val Asn Gly Asp Asp Glu Val
        195                 200                 205

Met Ser Pro Met Pro Ala Lys Lys Pro Arg Phe Asp Phe Pro Val Lys
    210                 215                 220

Leu Gln Leu
225


<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

ggggacaagt ttgtacaaaa aagcaggctt cacaatggcg ctcgaggctc                50


<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 4

ggggaccact ttgtacaaga aagctgggta atttccttaa agttgaagtt tga           53


<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ala Leu Gly Gly His
1               5


<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Met or Trp

<400> SEQUENCE: 6

Asn Asn Xaa Gln Met His
1               5


<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Cys, Phe, Gly, His, Ile, Lys, Leu, Met,
      Arg, Thr, Val, Trp or Tyr
<220> FEATURE:
<221> NAME/KEY: MOD_RES
<222> LOCATION: (5)..(5)
<223> OTHER INFORMATION: Ala, Cys, Phe, Gly, His, Ile, Lys, Leu, Met,
      Arg, Thr, Val, Trp or Tyr
<220> FEATURE:
<221> NAME/KEY: MOD_RES
<222> LOCATION: (6)..(6)
<223> OTHER INFORMATION: Variable amino acid or not present

<400> SEQUENCE: 7

Xaa Asp Leu Asn Xaa Xaa Pro
1               5


<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present
<220> FEATURE:
<221> NAME/KEY: MOD_RES
<222> LOCATION: (6)..(6)
```

<223> OTHER INFORMATION: Variable amino acid

<400> SEQUENCE: 8

Lys Arg Ser Lys Arg Xaa Arg
1 5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid

<400> SEQUENCE: 9

Glu Xaa Glu Xaa Xaa Ala Xaa Cys Leu Xaa Xaa Leu
1 5 10

<210> SEQ ID NO 10
<211> LENGTH: 1006
<212> TYPE: DNA
<213> ORGANISM: Datisca glomerata

<400> SEQUENCE: 10
ggcacgagga caaattctct ctctatcctc tgaatatctt tggtttgtga actgagaagc 60
tattagatgg ctctagaagc gctcaactct ccgaccacag ctacgccggt gtttcactac 120
gacgacccca gcttgaatta ccttgagcca tggaccaagc gtaagcgttc caagcgtacg 180
cgcttagata gccccatacc gaggaagagt accttgcttt ctgcctcatc atgctcgctc 240
gtggccgcgt tgcctctgca aatcgacggg attctcagtc ttccattcag attcagcctg 300
aagcaacgac ttcggctacc aaagtcagtt ataagtgctc tgtgtgcgat aaggcctttt 360
cgtcttatca ggctttgggt gggcacaagg ccagccacag aaagctcgct ggcggcgaag 420
atcaatcgac ttcctttgcc accacgaatt cagccaccgt cactaccacc acagcctccg 480
gaggtggtgg caggtctcat gagtgttcta tttgccacaa atcgttcccg actggccagg 540
ccttgggtgg tcacaagcgc tgccactacg aaggcagtat cggcggcaat agtattcacc 600
accacaacaa taccaccaac agcggaagca acggtggcat gagcatgacc tccgaagtag 660
gttccacaca cacagtcagc cacagtcacc gtgacttcga tctcaacatc ccggccttgc 720
cggagtttcg gtcgaatttc ttcatatccg ggatgacgga ggtcgagagt cctcatccgg 780
ccaagaaacc ccgtatattg atgaaataaa acatttctca agatcactga accaggcttt 840
agtttcttta taggaggaga tttaaaaaag tagtatctct ctttctttat ccgtaggata 900
attaatatat ttcgtgtaca taaatttgta gttctttaac acactctgtt tcattttctt 960
gctttgctca actttgtatt ggttatttca ttatgaaaat tcaatt 1006

```
<210> SEQ ID NO 11
<211> LENGTH: 247
<212> TYPE: PRT
<213> ORGANISM: Datisca glomerata

<400> SEQUENCE: 11

Met Ala Leu Glu Ala Leu Asn Ser Pro Thr Thr Ala Thr Pro Val Phe
1               5                   10                  15

His Tyr Asp Asp Pro Ser Leu Asn Tyr Leu Glu Pro Trp Thr Lys Arg
            20                  25                  30

Lys Arg Ser Lys Arg Thr Arg Leu Asp Ser Pro His Thr Glu Glu Glu
        35                  40                  45

Tyr Leu Ala Phe Cys Leu Ile Met Leu Ala Arg Gly Arg Val Ala Ser
    50                  55                  60

Ala Asn Arg Arg Asp Ser Gln Ser Ser Ile Gln Ile Gln Pro Glu Ala
65                  70                  75                  80

Thr Thr Ser Ala Thr Lys Val Ser Tyr Lys Cys Ser Val Cys Asp Lys
                85                  90                  95

Ala Phe Ser Ser Tyr Gln Ala Leu Gly Gly His Lys Ala Ser His Arg
            100                 105                 110

Lys Leu Ala Gly Gly Glu Asp Gln Ser Thr Ser Phe Ala Thr Thr Asn
        115                 120                 125

Ser Ala Thr Val Thr Thr Thr Thr Ala Ser Gly Gly Gly Gly Arg Ser
    130                 135                 140

His Glu Cys Ser Ile Cys His Lys Ser Phe Pro Thr Gly Gln Ala Leu
145                 150                 155                 160

Gly Gly His Lys Arg Cys His Tyr Glu Gly Ser Ile Gly Gly Asn Ser
                165                 170                 175

Ile His His His Asn Asn Thr Thr Asn Ser Gly Ser Asn Gly Gly Met
            180                 185                 190

Ser Met Thr Ser Glu Val Gly Ser Thr His Thr Val Ser His Ser His
        195                 200                 205

Arg Asp Phe Asp Leu Asn Ile Pro Ala Leu Pro Glu Phe Arg Ser Asn
    210                 215                 220

Phe Phe Ile Ser Gly Asp Asp Glu Val Glu Ser Pro His Pro Ala Lys
225                 230                 235                 240

Lys Pro Arg Ile Leu Met Lys
                245


<210> SEQ ID NO 12
<211> LENGTH: 996
<212> TYPE: DNA
<213> ORGANISM: Glycine max

<400> SEQUENCE: 12

aaaattctca ctctctctct catctcgaga tcatagtatc atattcaata tcatttcata     60

ccaaacacat ggctttggaa gctctcaact caccaacaac aaccgctcca tcttttccct    120

ttgacgaccc aactattcca tgggcgaaac gaaaacgttc aaagcgttct cgcgaccatc    180

cttctgaaga agagtacctc gccctctgcc tcatcatgct cgctcgcggc ggcaccacca    240

ccgtcaacaa ccgccacgtc agccctccgc cgctacagcc acagccacag ccgacaccag    300

atccttccac caagctcagt tacaaatgct ccgtttgcga caagagcttc cctcttacc     360

aagcgctcgg tggacacaag gccagtcacc ggaaactcgc cggcgccgcc gaagaccaac    420

cccccagcac caccacttcc tccgccgccg ccaccagctc cgcctccgga ggtaaggccc    480

atgagtgctc catttgccac aaatccttcc ccaccggaca ggcccttggc ggacacaaac    540
```

```
gttgtcacta cgaaggtaac ggtaacggaa ataacaacaa cagtaacagc gttgtcaccg    600

tcgcctcgga aggcgtgggc tccacccaca ctgtcagtca cggccaccac cgcgacttcg    660

atctcaacat cccggccttt ccggattttt cgaccaaggt cggagaagac gaggttgaga    720

gccctcaccc tgtcatgaag aagcctcgcc tcttcgtcat tcccaagatc gaaatccccc    780

aatttcaatg aactcgttga atttttagtt tatttttcga ctatatattt tggagaattt    840

tgagagttac tataatttga ttttgtacat agtacttgga agttttgttg gaccgtaccg    900

gacccagttc tctggttgag gttgtacttt cacaacagtg gcagatttgc aattcaattc    960

aatttatttg tttattttaa aaaaaaaaaa aaaaaa                              996
```

<210> SEQ ID NO 13
<211> LENGTH: 240
<212> TYPE: PRT
<213> ORGANISM: Glycine max

<400> SEQUENCE: 13

```
Met Ala Leu Glu Ala Leu Asn Ser Pro Thr Thr Thr Ala Pro Ser Phe
1               5                   10                  15

Pro Phe Asp Asp Pro Thr Ile Pro Trp Ala Lys Arg Lys Arg Ser Lys
            20                  25                  30

Arg Ser Arg Asp His Pro Ser Glu Glu Glu Tyr Leu Ala Leu Cys Leu
        35                  40                  45

Ile Met Leu Ala Arg Gly Gly Thr Thr Thr Val Asn Asn Arg His Val
    50                  55                  60

Ser Pro Pro Pro Leu Gln Pro Gln Pro Gln Pro Thr Pro Asp Pro Ser
65                  70                  75                  80

Thr Lys Leu Ser Tyr Lys Cys Ser Val Cys Asp Lys Ser Phe Pro Ser
                85                  90                  95

Tyr Gln Ala Leu Gly Gly His Lys Ala Ser His Arg Lys Leu Ala Gly
            100                 105                 110

Ala Ala Glu Asp Gln Pro Pro Ser Thr Thr Thr Ser Ser Ala Ala Ala
        115                 120                 125

Thr Ser Ser Ala Ser Gly Gly Lys Ala His Glu Cys Ser Ile Cys His
    130                 135                 140

Lys Ser Phe Pro Thr Gly Gln Ala Leu Gly Gly His Lys Arg Cys His
145                 150                 155                 160

Tyr Glu Gly Asn Gly Asn Gly Asn Asn Asn Asn Ser Asn Ser Val Val
                165                 170                 175

Thr Val Ala Ser Glu Gly Val Gly Ser Thr His Thr Val Ser His Gly
            180                 185                 190

His His Arg Asp Phe Asp Leu Asn Ile Pro Ala Phe Pro Asp Phe Ser
        195                 200                 205

Thr Lys Val Gly Glu Asp Glu Val Glu Ser Pro His Pro Val Met Lys
    210                 215                 220

Lys Pro Arg Leu Phe Val Ile Pro Lys Ile Glu Ile Pro Gln Phe Gln
225                 230                 235                 240
```

<210> SEQ ID NO 14
<211> LENGTH: 1006
<212> TYPE: DNA
<213> ORGANISM: Medicago sativa

<400> SEQUENCE: 14

```
aattcggcac gagaaataac cacttctctc tcaaaacctc cttttgcctt ttgcttctac     60
```

```
tttcacttgc gtaacgctaa ctaactcttc tcgagtgttc ttcttttcat catatggcta    120

tggaagcact taactcaccc accactgcta ctcctttcac accctttgag gaaccaaatc    180

tgagttatct tgaaacaccg tggacgaaag gtaaacgatc aaagcgttct cgcatggatc    240

aatcttcatg cactgaagaa gagtatctcg ctctttgtct catcatgctt gctcgcagcg    300

gtaacaacaa cgacaaaaag tctgattcgg tggcgacgcc gctaaccacc gttaaactca    360

gtcacaaatg ctcagtctgc aacaaagctt tctcatctta tcaagcccta ggtggacaca    420

aagccagtca ccggaaagct gttatgtccg caaccaccgc tgaagatcag atcaccacca    480

cttcatccgc cgtgactacc agctctgctt ccaacggtaa gaacaagact catgagtgtt    540

ccatctgtca caaatccttc cctactggac aggctttggg aggacacaag cgttgtcact    600

acgaaggcag cgttggtgcc ggtgccggtg ctggaagtaa cgctgtaact gcctctgaag    660

gagttggatt gtcacacagc caccaccgtg attttgatct taacctcccg gcttttccgg    720

acttttcaaa gaagtttttc gtggatgacg aggtttttag tcctttacct gctgcaaaga    780

agccctgtct tttcaagctg gaaattcctt ctcattactg atcaataata gatccaattt    840

tattgttatt attattaata attattatcg cttagggcat agttattttc tttttttcttt   900

caattatttc ggatcaattt gttctgtaca tacaaattgg gattggtttt agaatttagg    960

acggttgtag acaatggaaa ttcaattcaa ttatttaatt ttgtgt                  1006
```

```
<210> SEQ ID NO 15
<211> LENGTH: 235
<212> TYPE: PRT
<213> ORGANISM: Medicago sativa

<400> SEQUENCE: 15

Met Ala Met Glu Ala Leu Asn Ser Pro Thr Thr Ala Thr Pro Phe Thr
1               5                   10                  15

Pro Phe Glu Glu Pro Asn Leu Ser Tyr Leu Glu Thr Pro Trp Thr Lys
            20                  25                  30

Gly Lys Arg Ser Lys Arg Ser Arg Met Asp Gln Ser Ser Cys Thr Glu
        35                  40                  45

Glu Glu Tyr Leu Ala Leu Cys Leu Ile Met Leu Ala Arg Ser Gly Asn
    50                  55                  60

Asn Asn Asp Lys Lys Ser Asp Ser Val Ala Thr Pro Leu Thr Thr Val
65                  70                  75                  80

Lys Leu Ser His Lys Cys Ser Val Cys Asn Lys Ala Phe Ser Ser Tyr
                85                  90                  95

Gln Ala Leu Gly Gly His Lys Ala Ser His Arg Lys Ala Val Met Ser
            100                 105                 110

Ala Thr Thr Ala Glu Asp Gln Ile Thr Thr Thr Ser Ser Ala Val Thr
        115                 120                 125

Thr Ser Ser Ala Ser Asn Gly Lys Asn Lys Thr His Glu Cys Ser Ile
    130                 135                 140

Cys His Lys Ser Phe Pro Thr Gly Gln Ala Leu Gly Gly His Lys Arg
145                 150                 155                 160

Cys His Tyr Glu Gly Ser Val Gly Ala Gly Ala Gly Ala Gly Ser Asn
                165                 170                 175

Ala Val Thr Ala Ser Glu Gly Val Gly Leu Ser His Ser His His Arg
            180                 185                 190

Asp Phe Asp Leu Asn Leu Pro Ala Phe Pro Asp Phe Ser Lys Lys Phe
        195                 200                 205

Phe Val Asp Asp Glu Val Phe Ser Pro Leu Pro Ala Ala Lys Lys Pro
```

```
    210                 215                 220

Cys Leu Phe Lys Leu Glu Ile Pro Ser His Tyr
225                 230                 235


<210> SEQ ID NO 16
<211> LENGTH: 1061
<212> TYPE: DNA
<213> ORGANISM: Nicotiana tabacum

<400> SEQUENCE: 16

ttttccctcg aatttgataa ctaaagagaa tattatgact cttgaagctt tgaagtcacc      60

tacggcggca acgccgactc taccaccacg ctatgaagat gatgatgaaa ttcataattt     120

ggattcttgg gctaaaggaa aacgatcaaa acggccccgt attgatgccc caccgactga     180

agaagagtat ttagccctct gtctcatcat gctcgctcgc agcggaaccg gaaccagaac     240

cggtttaact gatgctacta cttcccaaca acctgccgat aaaaaaaccg ccgagttgcc     300

gccggttcat aagaaagagg tggcaacaga gcaagcagag caatcttaca agtgtagcgt     360

gtgtgacaag gctttttctt cttatcaagc actcggtggg cataaagcaa gtcaccgtaa     420

aactactact actgctaccg ccgcctctga tgataacaat ccttcaactt caacttccac     480

tggcgccgtt aatatctctg ctcttaatcc aactggtcgt tcacacgtct gttctatttg     540

ccacaaggct tttcctactg gccaagcttt gggtgggcac aagcgccgcc actatgaagg     600

caaactcggt ggtaacagcc gcgacttagg cggcggcggc ggcggcggtc atagtggaag     660

cgtcttgact acttcagacg gcggcgcgtc gactcacacg ctacgtgact ttgacctgaa     720

catgcctgct tcgccggaat tgcaactggg tctgagtatt gattgtggac ggaaaagtca     780

actgttgccg atggtccaag aggtggaaag tcctatgcct gcaaagaaac cgcgtttatt     840

gttttcgttg ggttgaaact tctttagggg aattgaattg attgtgtttt agccaaatta     900

gtaaattggt tcatgtgatt ttatttttag gaaaaggaat tattgattgt tttacccgtt     960

tattcttagg gtggtattat gtacagggag tgaatcattc attggtttta cactttctta    1020

attatatatt cttttttttt acacataaaa aaaaaaaaaa a                        1061


<210> SEQ ID NO 17
<211> LENGTH: 273
<212> TYPE: PRT
<213> ORGANISM: Nicotiana tabacum

<400> SEQUENCE: 17

Met Thr Leu Glu Ala Leu Lys Ser Pro Thr Ala Ala Thr Pro Thr Leu
1               5                   10                  15

Pro Pro Arg Tyr Glu Asp Asp Asp Glu Ile His Asn Leu Asp Ser Trp
            20                  25                  30

Ala Lys Gly Lys Arg Ser Lys Arg Pro Arg Ile Asp Ala Pro Pro Thr
        35                  40                  45

Glu Glu Glu Tyr Leu Ala Leu Cys Leu Ile Met Leu Ala Arg Ser Gly
    50                  55                  60

Thr Gly Thr Arg Thr Gly Leu Thr Asp Ala Thr Thr Ser Gln Gln Pro
65                  70                  75                  80

Ala Asp Lys Lys Thr Ala Glu Leu Pro Pro Val His Lys Lys Glu Val
                85                  90                  95

Ala Thr Glu Gln Ala Glu Gln Ser Tyr Lys Cys Ser Val Cys Asp Lys
            100                 105                 110

Ala Phe Ser Ser Tyr Gln Ala Leu Gly Gly His Lys Ala Ser His Arg
        115                 120                 125
```

```
Lys Thr Thr Thr Thr Ala Thr Ala Ala Ser Asp Asp Asn Asn Pro Ser
    130                 135                 140

Thr Ser Thr Ser Thr Gly Ala Val Asn Ile Ser Ala Leu Asn Pro Thr
145                 150                 155                 160

Gly Arg Ser His Val Cys Ser Ile Cys His Lys Ala Phe Pro Thr Gly
                165                 170                 175

Gln Ala Leu Gly Gly His Lys Arg Arg His Tyr Glu Gly Lys Leu Gly
            180                 185                 190

Gly Asn Ser Arg Asp Leu Gly Gly Gly Gly Gly Gly Gly His Ser Gly
        195                 200                 205

Ser Val Leu Thr Thr Ser Asp Gly Gly Ala Ser Thr His Thr Leu Arg
    210                 215                 220

Asp Phe Asp Leu Asn Met Pro Ala Ser Pro Glu Leu Gln Leu Gly Leu
225                 230                 235                 240

Ser Ile Asp Cys Gly Arg Lys Ser Gln Leu Leu Pro Met Val Gln Glu
                245                 250                 255

Val Glu Ser Pro Met Pro Ala Lys Lys Pro Arg Leu Leu Phe Ser Leu
            260                 265                 270

Gly


<210> SEQ ID NO 18
<211> LENGTH: 1213
<212> TYPE: DNA
<213> ORGANISM: Oryza sativa

<400> SEQUENCE: 18

aattcggcac gaggccacac agcaaccagc cagctgccac actagcttga ggcgagcgag      60

cgaagcttag ctagcggata gaacaagtcg tcgatctgct tgctgctttt gtgaattgcg     120

gtggaagcat gtcgagcgcg tcgtccatgg aagcgctcca cgccgcggtg ctcaaggagg     180

agcagcagca gcacgaggtg gaggaggcga cggtcgtgac gagcagcagc gccacgagcg     240

gggaggaggg cggacacctg ccccaggggt gggcgaagcg gaagcggtcg cgccgccagc     300

gatcggagga ggagaacctc gcgctctgcc tcctcatgct cgcccgcggc ggccaccacc     360

gcgtccaggc gccgcctccg ctctcggctt cggcgccccc gccggcaggt gcggagttca     420

agtgctccgt ctgcggcaag tccttcagct cctaccaggc gctcggcggc cacaagacga     480

gccaccgggt caagctgccg actccgcccg cagctcccgt cttggctccc gcccccgtcg     540

ccgccttgct gccttccgcc gaggaccgcg agccagccac gtcatccacc gccgcgtcct     600

ccgacggcat gaccaacaga gtccacaggt gttccatctg ccagaaggag ttccccaccg     660

ggcaggcgct cggcgggcac aagaggaagc actacgacgg tggcgtaggc gccggcgccg     720

gcgcatcttc aaccgagctc ctggccacgg tggccgccga gtccgaggtg ggaagctccg     780

gcaacggcca gtccgccacc cgggcgttcg acctcaacct cccggccgtg ccggagttcg     840

tgtggcggcc gtgctccaag ggcaagaaga tgtgggacga ggaggaggag gtccagagcc     900

ccctcgcctt caagaagccc cggcttctca ccgcgtaatt cagcagctgc acggatccga     960

tccgtcagag tttttgtcta gggagtgaaa ttcagtcgaa acacactatt cgttgattcg    1020

ttttgtgccg ctattgttta atttgttcct gcttttgtac agagcaagcg agtgatacat    1080

agccatacat acagtcatac agatataggt ctagctcttc cttggttctt tgtaacactg    1140

gaactgtacc tgtatctttt acactttgtt ctttgacagt catatattgt agaccaaaaa    1200

aaaaaaaaaa aaa                                                        1213
```

<210> SEQ ID NO 19
<211> LENGTH: 269
<212> TYPE: PRT
<213> ORGANISM: Oryza sativa

<400> SEQUENCE: 19

```
Met Ser Ser Ala Ser Ser Met Glu Ala Leu His Ala Ala Val Leu Lys
1               5                   10                  15

Glu Glu Gln Gln Gln His Glu Val Glu Glu Ala Thr Val Val Thr Ser
            20                  25                  30

Ser Ser Ala Thr Ser Gly Glu Glu Gly Gly His Leu Pro Gln Gly Trp
        35                  40                  45

Ala Lys Arg Lys Arg Ser Arg Arg Gln Arg Ser Glu Glu Glu Asn Leu
    50                  55                  60

Ala Leu Cys Leu Leu Met Leu Ala Arg Gly Gly His His Arg Val Gln
65                  70                  75                  80

Ala Pro Pro Pro Leu Ser Ala Ser Ala Pro Pro Pro Ala Gly Ala Glu
                85                  90                  95

Phe Lys Cys Ser Val Cys Gly Lys Ser Phe Ser Ser Tyr Gln Ala Leu
            100                 105                 110

Gly Gly His Lys Thr Ser His Arg Val Lys Leu Pro Thr Pro Pro Ala
        115                 120                 125

Ala Pro Val Leu Ala Pro Ala Pro Val Ala Ala Leu Leu Pro Ser Ala
    130                 135                 140

Glu Asp Arg Glu Pro Ala Thr Ser Ser Thr Ala Ala Ser Ser Asp Gly
145                 150                 155                 160

Met Thr Asn Arg Val His Arg Cys Ser Ile Cys Gln Lys Glu Phe Pro
                165                 170                 175

Thr Gly Gln Ala Leu Gly Gly His Lys Arg Lys His Tyr Asp Gly Gly
            180                 185                 190

Val Gly Ala Gly Ala Gly Ala Ser Ser Thr Glu Leu Leu Ala Thr Val
        195                 200                 205

Ala Ala Glu Ser Glu Val Gly Ser Ser Gly Asn Gly Gln Ser Ala Thr
    210                 215                 220

Arg Ala Phe Asp Leu Asn Leu Pro Ala Val Pro Glu Phe Val Trp Arg
225                 230                 235                 240

Pro Cys Ser Lys Gly Lys Lys Met Trp Asp Glu Glu Glu Glu Val Gln
                245                 250                 255

Ser Pro Leu Ala Phe Lys Lys Pro Arg Leu Leu Thr Ala
            260                 265
```

<210> SEQ ID NO 20
<211> LENGTH: 1020
<212> TYPE: DNA
<213> ORGANISM: Petunia x hybrida

<400> SEQUENCE: 20

```
ttcactcacc aaaacaactt ctctacctct tctacttgca cattcaaatt ctttcattac      60

tacttatctc tactaatctt gattcgattt tagtaaatca aacaagagaa tcttttcagt     120

aatacaaaca agaaaatttt ctctctatac ttgattgagt ttagtaaggc aaacaagaaa     180

actatcatgg cacttgaagc attgaattct ccaactacaa caacaccacc atcattccaa     240

tttgagaaca acgggcttaa gtaccttgag agttggacaa aaggtaaaag atcaaaaagg     300

caacgcagca tggaacgaca gtgtactgaa gaagagtatt tagcactttg tcttatcatg     360

ctagcacgta gcgatggttc tgttaataac tcacggtctc taccaccacc accactacca     420
```

```
ccatcagttc cagtaacgtc gcaaataaac gcgacgttat tggaacagaa gaatttgtac    480

aagtgttccg tttgtggtaa agggtttggg tcttatcaag ctttaggtgg acataaagca    540

agtcaccgga aacttgtcag catgggagga gatgaacaat ctactacttc cactactact    600

aacgtaacgg gaactagttc cgctaacgtt aacggtaacg gaagaactca cgaatgttca    660

atttgtcaca agtgctttcc tactggacaa gctttaggtg gtcataaaag gtgccactat    720

gacggtggta acggtaacgg taacggaagt gtaagtgttg ggtgacgtc atctgaaggt    780

gtggggtcca ctattagtca tcaccgtgac tttgacttga atattcccgc gttgccggag    840

ttttggccgg gatttggttc cggcgaggat gaggtggaga gtcctcatcc agcaaagaag    900

tcaaggctat ctcttccacc taaacttgaa ttattcaaag gattatagag ggaatattga    960

tttgttacag gaagatttat taggattcac gaattttttg ttgactagtt tatgtaatat   1020
```

<210> SEQ ID NO 21
<211> LENGTH: 253
<212> TYPE: PRT
<213> ORGANISM: Petunia x hybrida

<400> SEQUENCE: 21

```
Met Ala Leu Glu Ala Leu Asn Ser Pro Thr Thr Thr Thr Pro Pro Ser
1               5                   10                  15

Phe Gln Phe Glu Asn Asn Gly Leu Lys Tyr Leu Glu Ser Trp Thr Lys
            20                  25                  30

Gly Lys Arg Ser Lys Arg Gln Arg Ser Met Glu Arg Gln Cys Thr Glu
        35                  40                  45

Glu Glu Tyr Leu Ala Leu Cys Leu Ile Met Leu Ala Arg Ser Asp Gly
    50                  55                  60

Ser Val Asn Asn Ser Arg Ser Leu Pro Pro Pro Pro Leu Pro Pro Ser
65                  70                  75                  80

Val Pro Val Thr Ser Gln Ile Asn Ala Thr Leu Leu Glu Gln Lys Asn
                85                  90                  95

Leu Tyr Lys Cys Ser Val Cys Gly Lys Gly Phe Gly Ser Tyr Gln Ala
            100                 105                 110

Leu Gly Gly His Lys Ala Ser His Arg Lys Leu Val Ser Met Gly Gly
        115                 120                 125

Asp Glu Gln Ser Thr Thr Ser Thr Thr Thr Asn Val Thr Gly Thr Ser
    130                 135                 140

Ser Ala Asn Val Asn Gly Asn Gly Arg Thr His Glu Cys Ser Ile Cys
145                 150                 155                 160

His Lys Cys Phe Pro Thr Gly Gln Ala Leu Gly Gly His Lys Arg Cys
                165                 170                 175

His Tyr Asp Gly Gly Asn Gly Asn Gly Asn Gly Ser Val Ser Val Gly
            180                 185                 190

Val Thr Ser Ser Glu Gly Val Gly Ser Thr Ile Ser His His Arg Asp
        195                 200                 205

Phe Asp Leu Asn Ile Pro Ala Leu Pro Glu Phe Trp Pro Gly Phe Gly
    210                 215                 220

Ser Gly Glu Asp Glu Val Glu Ser Pro His Pro Ala Lys Lys Ser Arg
225                 230                 235                 240

Leu Ser Leu Pro Pro Lys Leu Glu Leu Phe Lys Gly Leu
                245                 250
```

<210> SEQ ID NO 22
<211> LENGTH: 786

<212> TYPE: DNA
<213> ORGANISM: Triticum aestivum

<400> SEQUENCE: 22

```
atgtcgtcgt cggccatgga agcgctccac gccctgatcc cggagcagca ccagctggac     60

gttgaggcgg ctgcggctgt cagcagcgcc accagcggcg aggagagcgg ccacgtgctg    120

caggggtggg ccaagaggaa gcgatcgcgc cgccagcgct ccgaggagga gaacctcgcg    180

ctctgcctcc tcatgctctc gcgcggcggc aagcagcgtg ttcaggcgcc gcagccggag    240

tcgttcgctg cgccggtgcc tgccgagttc aagtgctccg tctgcggcaa gtccttcagc    300

tcctaccagg cgctcggagg ccacaagacg agccaccggg tgaagcagcc gtctcctccc    360

tctgatgccg ctgctgcccc actcgtggcc ctcccggccg tcgccgccat cctgccgtcc    420

gccgagccgg ccacgtcgtc caccgccgcg tcctccgacg gcgcgaccaa cagagtccac    480

aggtgctcca tctgccaaaa ggagttcccg actgggcagg cgctcggcgg gcacaagagg    540

aagcactacg acggaggcgt gggcgccgcc gcctcgtcga ccgagcttct ggccgccgcg    600

gccgccgagt ctgaggtggg gagcaccggc aacgggagct ccgccgcccg ggccttcgac    660

ctgaacattc cggccgtgcc ggagttcgtg tggaggccgt gcgccaaggg caagatgatg    720

tgggaggacg atgaggaggt gcagagcccc ctcgccttca agaagcctcg gcttctcacc    780

gcttga                                                               786
```

<210> SEQ ID NO 23
<211> LENGTH: 261
<212> TYPE: PRT
<213> ORGANISM: Triticum aestivum

<400> SEQUENCE: 23

```
Met Ser Ser Ser Ala Met Glu Ala Leu His Ala Leu Ile Pro Glu Gln
1               5                   10                  15

His Gln Leu Asp Val Glu Ala Ala Ala Ala Val Ser Ser Ala Thr Ser
            20                  25                  30

Gly Glu Glu Ser Gly His Val Leu Gln Gly Trp Ala Lys Arg Lys Arg
        35                  40                  45

Ser Arg Arg Gln Arg Ser Glu Glu Glu Asn Leu Ala Leu Cys Leu Leu
    50                  55                  60

Met Leu Ser Arg Gly Gly Lys Gln Arg Val Gln Ala Pro Gln Pro Glu
65                  70                  75                  80

Ser Phe Ala Ala Pro Val Pro Ala Glu Phe Lys Cys Ser Val Cys Gly
                85                  90                  95

Lys Ser Phe Ser Ser Tyr Gln Ala Leu Gly Gly His Lys Thr Ser His
            100                 105                 110

Arg Val Lys Gln Pro Ser Pro Pro Ser Asp Ala Ala Ala Ala Pro Leu
        115                 120                 125

Val Ala Leu Pro Ala Val Ala Ala Ile Leu Pro Ser Ala Glu Pro Ala
    130                 135                 140

Thr Ser Ser Thr Ala Ala Ser Ser Asp Gly Ala Thr Asn Arg Val His
145                 150                 155                 160

Arg Cys Ser Ile Cys Gln Lys Glu Phe Pro Thr Gly Gln Ala Leu Gly
                165                 170                 175

Gly His Lys Arg Lys His Tyr Asp Gly Gly Val Gly Ala Ala Ala Ser
            180                 185                 190

Ser Thr Glu Leu Leu Ala Ala Ala Ala Ala Glu Ser Glu Val Gly Ser
        195                 200                 205
```

```
Thr Gly Asn Gly Ser Ser Ala Ala Arg Ala Phe Asp Leu Asn Ile Pro
    210                 215                 220

Ala Val Pro Glu Phe Val Trp Arg Pro Cys Ala Lys Gly Lys Met Met
225                 230                 235                 240

Trp Glu Asp Asp Glu Glu Val Gln Ser Pro Leu Ala Phe Lys Lys Pro
                245                 250                 255

Arg Leu Leu Thr Ala
            260


<210> SEQ ID NO 24
<211> LENGTH: 1026
<212> TYPE: DNA
<213> ORGANISM: Capsicum annum

<400> SEQUENCE: 24

aaaatcttcg ctacttactt acatcttcta gaatagtcac tagaaccagt aactttatac     60

aacggatatc gatatggcac ttgaagcttt gaattctcca actggtacac caactccgcc    120

accgtttcaa tttgagagcg acggccaaca gcttcgatat atcgaaaact ggaggaaggg    180

aaagagatct aaaaggtcac gcagcatgga gcaccagcct actgaggaag aatacttagc    240

gctttgtttg atcatgcttg cacgtagcgg tggctccgtt aatcatcaac gatctctacc    300

accgccggct ccggtgatga aactgcacgc gccgtcgtca tcatcggcgg cggaggagga    360

gaaggagaag atggtgtata agtgttcggt ttgtggtaag ggatttgggt cttatcaagc    420

tttaggtgga cacaaagcta gtcaccggaa actcgtaccc ggcggagatg atcagtcaac    480

tacctccaca accactaacg caaccggaac aacaacctcc gttaacggca acggcaacag    540

aagtggaagg actcacgagt gttcgatttg tcacaagtgt tttcccactg gacaagcttt    600

aggtggacac aaaaggtgtc actacgacgg cggtatcggt aacggaaacg ctaacagtgg    660

cgttagtgct agcgttggag tgacgtcatc ggagggtgtg gggtccacag tcagtcaccg    720

ggatttcgac ttgaacattc cggcgttgcc ggaattctgg ctgggatttg gttccggcga    780

agatgaggtg gagagtccac atccggcgaa gaaatcgcgg ttatgtttgc ctccaaaata    840

tgaattattt caacattaat gggaatttga ttgttaggat ttactatttt ggtagacaaa    900

attatactat gtaagtttta attttcattg tgggtgggag caaaattttt aattttttgt    960

ctatagacct agctagttac taatagcaaa aattcaattg attgatttaa aaaaaaaaaa   1020

aaaaaa                                                              1026


<210> SEQ ID NO 25
<211> LENGTH: 261
<212> TYPE: PRT
<213> ORGANISM: Capsicum annum

<400> SEQUENCE: 25

Met Ala Leu Glu Ala Leu Asn Ser Pro Thr Gly Thr Pro Thr Pro Pro
1               5                   10                  15

Pro Phe Gln Phe Glu Ser Asp Gly Gln Gln Leu Arg Tyr Ile Glu Asn
            20                  25                  30

Trp Arg Lys Gly Lys Arg Ser Lys Arg Ser Arg Ser Met Glu His Gln
        35                  40                  45

Pro Thr Glu Glu Glu Tyr Leu Ala Leu Cys Leu Ile Met Leu Ala Arg
    50                  55                  60

Ser Gly Gly Ser Val Asn His Gln Arg Ser Leu Pro Pro Pro Ala Pro
65                  70                  75                  80

Val Met Lys Leu His Ala Pro Ser Ser Ser Ser Ala Ala Glu Glu Glu
```

-continued

```
                85                  90                  95

Lys Glu Lys Met Val Tyr Lys Cys Ser Val Cys Gly Lys Gly Phe Gly
            100                 105                 110

Ser Tyr Gln Ala Leu Gly Gly His Lys Ala Ser His Arg Lys Leu Val
        115                 120                 125

Pro Gly Gly Asp Asp Gln Ser Thr Thr Ser Thr Thr Thr Asn Ala Thr
    130                 135                 140

Gly Thr Thr Thr Ser Val Asn Gly Asn Gly Asn Arg Ser Gly Arg Thr
145                 150                 155                 160

His Glu Cys Ser Ile Cys His Lys Cys Phe Pro Thr Gly Gln Ala Leu
                165                 170                 175

Gly Gly His Lys Arg Cys His Tyr Asp Gly Gly Ile Gly Asn Gly Asn
            180                 185                 190

Ala Asn Ser Gly Val Ser Ala Ser Val Gly Val Thr Ser Ser Glu Gly
        195                 200                 205

Val Gly Ser Thr Val Ser His Arg Asp Phe Asp Leu Asn Ile Pro Ala
    210                 215                 220

Leu Pro Glu Phe Trp Leu Gly Phe Gly Ser Gly Glu Asp Glu Val Glu
225                 230                 235                 240

Ser Pro His Pro Ala Lys Lys Ser Arg Leu Cys Leu Pro Pro Lys Tyr
                245                 250                 255

Glu Leu Phe Gln His
            260


<210> SEQ ID NO 26
<211> LENGTH: 1068
<212> TYPE: DNA
<213> ORGANISM: Arabidopsis thaliana

<400> SEQUENCE: 26

acttcactct ctaatttcct tctctctatc tctcaccata ttcgcgatta aaaactctca      60

acttttctct caaatttctg atcctttgat ccaacagtta gaagaagatt catctgatca     120

tggccctcga agcgatgaac actccaactt cttctttcac cagaatcgaa acgaaagaag     180

atttgatgaa cgacgccgtt ttcattgagc cgtggcttaa acgcaaacgc tccaaacgtc     240

agcgttctca cagccccttct tcgtcttctt cctcaccgcc tcgatctcga cccaaatccc     300

agaatcaaga tcttacggaa gaagagtatc tcgctctttg tctcctcatg ctcgctaaag     360

atcaaccgtc gcaaacgcga tttcatcaac agtcgcaatc gttaacgccg ccgccagaat     420

caaagaacct tccgtacaag tgtaacgtct gtgaaaaagc gtttccttcc tatcaggctt     480

taggcggtca caaagcaagt caccgaatca aaccaccaac cgtaatctca acaaccgccg     540

atgattcaac agctccgacc atctccatcg tcgccggaga aaaacatccg attgctgcct     600

ccggaaagat ccacgagtgt tcaatctgtc ataaagtgtt tccgacgggt caagctttag     660

gcggtcacaa acgttgtcac tacgaaggca acctcggcgg cggaggagga ggaggaagca     720

aatcaatcag tcacagtgga agcgtgtcga gcacggtatc ggaagaaagg agccaccgtg     780

gattcatcga tctaaaccta ccggcgttac ctgaactcag ccttcatcac aatccaatcg     840

tcgacgaaga gatcttgagt ccgttgaccg gtaaaaaacc gcttttgttg accgatcacg     900

accaagtcat caagaaagaa gatttatctt taaaaatcta atactcgact attaattctt     960

gtgtgatttt tttcgttaca accatagttt cattttcatt tttttagtta caaattttta    1020

attgttctga tttggattga atattggtat attgttaggg gttgatac                 1068
```

<210> SEQ ID NO 27
<211> LENGTH: 273
<212> TYPE: PRT
<213> ORGANISM: Arabidopsis thaliana

<400> SEQUENCE: 27

```
Met Ala Leu Glu Ala Met Asn Thr Pro Thr Ser Ser Phe Thr Arg Ile
1               5                   10                  15

Glu Thr Lys Glu Asp Leu Met Asn Asp Ala Val Phe Ile Glu Pro Trp
            20                  25                  30

Leu Lys Arg Lys Arg Ser Lys Arg Gln Arg Ser His Ser Pro Ser Ser
        35                  40                  45

Ser Ser Ser Ser Pro Pro Arg Ser Arg Pro Lys Ser Gln Asn Gln Asp
    50                  55                  60

Leu Thr Glu Glu Glu Tyr Leu Ala Leu Cys Leu Leu Met Leu Ala Lys
65                  70                  75                  80

Asp Gln Pro Ser Gln Thr Arg Phe His Gln Gln Ser Gln Ser Leu Thr
                85                  90                  95

Pro Pro Pro Glu Ser Lys Asn Leu Pro Tyr Lys Cys Asn Val Cys Glu
            100                 105                 110

Lys Ala Phe Pro Ser Tyr Gln Ala Leu Gly Gly His Lys Ala Ser His
        115                 120                 125

Arg Ile Lys Pro Pro Thr Val Ile Ser Thr Thr Ala Asp Asp Ser Thr
    130                 135                 140

Ala Pro Thr Ile Ser Ile Val Ala Gly Glu Lys His Pro Ile Ala Ala
145                 150                 155                 160

Ser Gly Lys Ile His Glu Cys Ser Ile Cys His Lys Val Phe Pro Thr
                165                 170                 175

Gly Gln Ala Leu Gly Gly His Lys Arg Cys His Tyr Glu Gly Asn Leu
            180                 185                 190

Gly Gly Gly Gly Gly Gly Gly Ser Lys Ser Ile Ser His Ser Gly Ser
        195                 200                 205

Val Ser Ser Thr Val Ser Glu Glu Arg Ser His Arg Gly Phe Ile Asp
    210                 215                 220

Leu Asn Leu Pro Ala Leu Pro Glu Leu Ser Leu His His Asn Pro Ile
225                 230                 235                 240

Val Asp Glu Glu Ile Leu Ser Pro Leu Thr Gly Lys Lys Pro Leu Leu
                245                 250                 255

Leu Thr Asp His Asp Gln Val Ile Lys Lys Glu Asp Leu Ser Leu Lys
            260                 265                 270

Ile
```

<210> SEQ ID NO 28
<211> LENGTH: 976
<212> TYPE: DNA
<213> ORGANISM: Arabidopsis thaliana

<400> SEQUENCE: 28

```
aaatcaaatc ttttcattta caattatctt tcttctcaat ttagaactta gtagctagtc      60

ttcaagataa tggcacttga aactcttact tctccaagat tatcttctcc gatgccgact     120

ctgtttcaag attcagcact agggtttcat ggaagcaaag gcaaacgatc taagcgatca     180

agatctgaat tcgaccgtca gagtctcacg gaggatgaat atatcgcttt atgtctcatg     240

cttcttgctc gcgacggaga tagaaaccgt gaccttgacc tgccttcttc ttcgtcttca     300

cctcctctgc ttcctcctct tcctactccg atctacaagt gtagcgtctg tgacaaggcg     360
```

```
ttttcgtctt accaggctct tggtggacac aaggcaagtc accggaaaag cttttcgctt    420

actcaatctg ccggaggaga tgagctgtcg acatcgtcgg cgataaccac gtctggtata    480

tccggtggcg gggaggaag tgtgaagtcg cacgtttgct ctatctgtca taaatcgttc    540

gccaccggtc aagctctcgg cggccacaaa cggtgccact acgaaggaaa gaacggaggc    600

ggtgtgagta gtagcgtgtc gaattctgaa gatgtggggt ctacaagcca cgtcagcagt    660

ggccaccgtg ggtttgacct caacataccg ccgataccgg aattctcgat ggtcaacgga    720

gacgaagagg tgatgagtcc tatgccggcg aagaaactcc ggtttgactt cccggagaaa    780

ccctaaacat aaacctagga aaaactttac agaattcatt ttataggaaa ttgttttact    840

gtatatacaa atatcgattt tgattgatgt tcttcttcac tgaaaaatta tgattctttg    900

ttgtataatt gatgtttctg aaaaagatat aactttttat tgtttcacac gtatcaaaat    960

ttgcttggat acatca                                                    976
```

```
<210> SEQ ID NO 29
<211> LENGTH: 238
<212> TYPE: PRT
<213> ORGANISM: Arabidopsis thaliana

<400> SEQUENCE: 29

Met Ala Leu Glu Thr Leu Thr Ser Pro Arg Leu Ser Ser Pro Met Pro
1               5                   10                  15

Thr Leu Phe Gln Asp Ser Ala Leu Gly Phe His Gly Ser Lys Gly Lys
            20                  25                  30

Arg Ser Lys Arg Ser Arg Ser Glu Phe Asp Arg Gln Ser Leu Thr Glu
        35                  40                  45

Asp Glu Tyr Ile Ala Leu Cys Leu Met Leu Leu Ala Arg Asp Gly Asp
    50                  55                  60

Arg Asn Arg Asp Leu Asp Leu Pro Ser Ser Ser Ser Ser Pro Pro Leu
65                  70                  75                  80

Leu Pro Pro Leu Pro Thr Pro Ile Tyr Lys Cys Ser Val Cys Asp Lys
                85                  90                  95

Ala Phe Ser Ser Tyr Gln Ala Leu Gly Gly His Lys Ala Ser His Arg
            100                 105                 110

Lys Ser Phe Ser Leu Thr Gln Ser Ala Gly Gly Asp Glu Leu Ser Thr
        115                 120                 125

Ser Ser Ala Ile Thr Thr Ser Gly Ile Ser Gly Gly Gly Gly Gly Ser
    130                 135                 140

Val Lys Ser His Val Cys Ser Ile Cys His Lys Ser Phe Ala Thr Gly
145                 150                 155                 160

Gln Ala Leu Gly Gly His Lys Arg Cys His Tyr Glu Gly Lys Asn Gly
                165                 170                 175

Gly Gly Val Ser Ser Ser Val Ser Asn Ser Glu Asp Val Gly Ser Thr
            180                 185                 190

Ser His Val Ser Ser Gly His Arg Gly Phe Asp Leu Asn Ile Pro Pro
        195                 200                 205

Ile Pro Glu Phe Ser Met Val Asn Gly Asp Glu Glu Val Met Ser Pro
    210                 215                 220

Met Pro Ala Lys Lys Leu Arg Phe Asp Phe Pro Glu Lys Pro
225                 230                 235

<210> SEQ ID NO 30
<211> LENGTH: 718
<212> TYPE: DNA
<213> ORGANISM: Arabidopsis thaliana
```

<400> SEQUENCE: 30

```
atggctctcg acactctcaa ttctcccacc tccaccacca caaccaccgc tcctcctcct     60
ttcctccgtt gcctcgacga aaccgagccc gaaaacctcg aatcatggac caaaagaaaa    120
cgtacaaaac gtcaccgtat agatcaacca aaccctcctc cttctgaaga agagtatctc    180
gctctttgcc tccttatgct cgctcgtggc tcctccgatc atcactctcc accgtcggat    240
catcactctc tttctccact gtccgatcat cagaaagatt acaagtgttc cgtctgtggc    300
aaatctttcc cgtcttacca agcgttaggt ggacacaaaa caagtcaccg gaaaccggtt    360
agtgtcgatg ttaataatag taacggaacc gttactaata acggaaatat tagtaacggt    420
ttagttggtc aaagtgggaa gactcataac tgctctatat gttttaagtc gtttccctct    480
ggtcaagcat tgggtggtca caaacgttgt cactatgatg gtggtaacgg taacagtaac    540
ggtgacaata gccacaagtt tgacctaaat ttaccggctg atcaagttag tgatgagaca    600
attggaaaaa gtcaactctc cggtgaagaa acaaagtcgg tgttgtgatt attattattt    660
tttaccgatc gggattagct agtggttgat cattagctga gtctgtaatg aaaatgat      718
```

<210> SEQ ID NO 31
<211> LENGTH: 215
<212> TYPE: PRT
<213> ORGANISM: Arabidopsis thaliana

<400> SEQUENCE: 31

```
Met Ala Leu Asp Thr Leu Asn Ser Pro Thr Ser Thr Thr Thr Thr Thr
1               5                   10                  15

Ala Pro Pro Pro Phe Leu Arg Cys Leu Asp Glu Thr Glu Pro Glu Asn
            20                  25                  30

Leu Glu Ser Trp Thr Lys Arg Lys Arg Thr Lys Arg His Arg Ile Asp
        35                  40                  45

Gln Pro Asn Pro Pro Pro Ser Glu Glu Glu Tyr Leu Ala Leu Cys Leu
    50                  55                  60

Leu Met Leu Ala Arg Gly Ser Ser Asp His His Ser Pro Pro Ser Asp
65                  70                  75                  80

His His Ser Leu Ser Pro Leu Ser Asp His Gln Lys Asp Tyr Lys Cys
                85                  90                  95

Ser Val Cys Gly Lys Ser Phe Pro Ser Tyr Gln Ala Leu Gly Gly His
            100                 105                 110

Lys Thr Ser His Arg Lys Pro Val Ser Val Asp Val Asn Asn Ser Asn
        115                 120                 125

Gly Thr Val Thr Asn Asn Gly Asn Ile Ser Asn Gly Leu Val Gly Gln
    130                 135                 140

Ser Gly Lys Thr His Asn Cys Ser Ile Cys Phe Lys Ser Phe Pro Ser
145                 150                 155                 160

Gly Gln Ala Leu Gly Gly His Lys Arg Cys His Tyr Asp Gly Gly Asn
                165                 170                 175

Gly Asn Ser Asn Gly Asp Asn Ser His Lys Phe Asp Leu Asn Leu Pro
            180                 185                 190

Ala Asp Gln Val Ser Asp Glu Thr Ile Gly Lys Ser Gln Leu Ser Gly
        195                 200                 205

Glu Glu Thr Lys Ser Val Leu
    210                 215
```

<210> SEQ ID NO 32
<211> LENGTH: 702

<212> TYPE: DNA
<213> ORGANISM: Arabidopsis thaliana

<400> SEQUENCE: 32

```
aaattttcta tagcaatggc gcttgaagct cttaattcac caagattggt cgaggatccc      60
ttaagattca atggcgttga gcagtggacc aaatgtaaga aacgatccaa acgttcgaga     120
tctgatcttc atcataacca ccgtctcact gaggaagagt atctagcttt ctgtctcatg     180
cttcttgctc gggatggcgg cgatcttgac tctgtgacgg ttgcggagaa gccgagttat     240
aagtgtggcg tttgttacaa gacgttttcg tcttaccaag ctctcggcgg tcataaagcg     300
agccaccgga gcttatacgg tggtggagag aatgataaat cgacaccatc caccgccgtg     360
aaatctcacg tttgttcggt ttgcgggaaa tctttcgcca ccggtcaagc tctcggcggc     420
cacaagcggt gccactacga tggtggcgtt tcgaactcgg aaggtgtggg gtctactagc     480
cacgtcagca gtagtagcca ccgtggattt gaccttaata ttataccggt gcagggattt     540
tcgccggacg acgaagtgat gagtccgatg gcgactaaga agcctcgcct gaagtaagtc     600
tttgttgaag acctggaagt ttatcaaatg taaatatcaa atttcaattt caaggaacag     660
ttttgttgat tctattacca atacacaata cgattcaatt cc                        702
```

<210> SEQ ID NO 33
<211> LENGTH: 193
<212> TYPE: PRT
<213> ORGANISM: Arabidopsis thaliana

<400> SEQUENCE: 33

```
Met Ala Leu Glu Ala Leu Asn Ser Pro Arg Leu Val Glu Asp Pro Leu
1               5                   10                  15

Arg Phe Asn Gly Val Glu Gln Trp Thr Lys Cys Lys Lys Arg Ser Lys
            20                  25                  30

Arg Ser Arg Ser Asp Leu His His Asn His Arg Leu Thr Glu Glu Glu
        35                  40                  45

Tyr Leu Ala Phe Cys Leu Met Leu Leu Ala Arg Asp Gly Gly Asp Leu
    50                  55                  60

Asp Ser Val Thr Val Ala Glu Lys Pro Ser Tyr Lys Cys Gly Val Cys
65                  70                  75                  80

Tyr Lys Thr Phe Ser Ser Tyr Gln Ala Leu Gly Gly His Lys Ala Ser
                85                  90                  95

His Arg Ser Leu Tyr Gly Gly Gly Glu Asn Asp Lys Ser Thr Pro Ser
            100                 105                 110

Thr Ala Val Lys Ser His Val Cys Ser Val Cys Gly Lys Ser Phe Ala
        115                 120                 125

Thr Gly Gln Ala Leu Gly Gly His Lys Arg Cys His Tyr Asp Gly Gly
    130                 135                 140

Val Ser Asn Ser Glu Gly Val Gly Ser Thr Ser His Val Ser Ser Ser
145                 150                 155                 160

Ser His Arg Gly Phe Asp Leu Asn Ile Ile Pro Val Gln Gly Phe Ser
                165                 170                 175

Pro Asp Asp Glu Val Met Ser Pro Met Ala Thr Lys Lys Pro Arg Leu
            180                 185                 190

Lys
```

<210> SEQ ID NO 34
<211> LENGTH: 1157
<212> TYPE: DNA
<213> ORGANISM: Arabidopsis thaliana

<400> SEQUENCE: 34

```
cacacttcac tctttcttca tcttcttctt cttaaatagc tcgaaatcac atctcacaga      60
attaaatctt atggctctcg agactctcaa ttctccaaca gctaccacca ccgctcggcc     120
tcttctccgg tatcgtgaag aaatggagcc tgagaatctc gagcaatggg ctaaaagaaa     180
acgaacaaaa cgtcaacgtt ttgatcacgg tcatcagaat caagaaacga acaagaacct     240
tccttctgaa gaagagtatc tcgctctttg tctcctcatg ctcgctcgtg gctccgccgt     300
acaatctcct cctcttcctc ctctaccgtc acgtgcgtca ccgtccgatc accgagatta     360
caagtgtacg gtctgtggga agtccttttc gtcataccaa gccttaggtg gacacaagac     420
gagtcaccgg aaaccgacga acactagtat cacttccggt aaccaagaac tgtctaataa     480
cagtcacagt aacagcggtt ccgttgttat taacgttacc gtgaacactg gtaacggtgt     540
tagtcaaagc ggaaagattc acacttgctc aatctgtttc aagtcgtttg cgtctggtca     600
agccttaggt ggacacaaac ggtgtcacta tgacggtggc aacaacggta acggtaacgg     660
aagtagcagc aacagcgtag aactcgtcgc tggtagtgac gtcagcgatg ttgataatga     720
gagatggtcc gaagaaagtg cgatcggtgg ccaccgtgga tttgacctaa acttaccggc     780
tgatcaagtc tcagtgacga cttcttaacg ttgactgagt ttgaggaaaa agtcaactat     840
caagcgaaga aagggttagt ggacggtgaa gattaacggt cgtttctttc cagttgcttc     900
ggtttgagct tgactgggtc tgtaatgaaa atgattggag tggacttggc attattatta     960
ttatttttaa aaagaaatgt taatttgttg ttggatttgt ttatagatag aggaaacaat    1020
tgggatacac aaatattttt ttttttaca aagaaaataa taatgcagag atggatgatt    1080
ggatcgtaca cgttattata tagtggacca ttctgtaatc gtgaattatt attatttgtt    1140
agaaatttaa ttttcgt                                                   1157
```

<210> SEQ ID NO 35
<211> LENGTH: 245
<212> TYPE: PRT
<213> ORGANISM: Arabidopsis thaliana

<400> SEQUENCE: 35

```
Met Ala Leu Glu Thr Leu Asn Ser Pro Thr Ala Thr Thr Thr Ala Arg
1               5                   10                  15

Pro Leu Leu Arg Tyr Arg Glu Glu Met Glu Pro Glu Asn Leu Glu Gln
            20                  25                  30

Trp Ala Lys Arg Lys Arg Thr Lys Arg Gln Arg Phe Asp His Gly His
        35                  40                  45

Gln Asn Gln Glu Thr Asn Lys Asn Leu Pro Ser Glu Glu Glu Tyr Leu
    50                  55                  60

Ala Leu Cys Leu Leu Met Leu Ala Arg Gly Ser Ala Val Gln Ser Pro
65                  70                  75                  80

Pro Leu Pro Pro Leu Pro Ser Arg Ala Ser Pro Ser Asp His Arg Asp
                85                  90                  95

Tyr Lys Cys Thr Val Cys Gly Lys Ser Phe Ser Ser Tyr Gln Ala Leu
            100                 105                 110

Gly Gly His Lys Thr Ser His Arg Lys Pro Thr Asn Thr Ser Ile Thr
        115                 120                 125

Ser Gly Asn Gln Glu Leu Ser Asn Asn Ser His Ser Asn Ser Gly Ser
    130                 135                 140

Val Val Ile Asn Val Thr Val Asn Thr Gly Asn Gly Val Ser Gln Ser
145                 150                 155                 160
```

```
Gly Lys Ile His Thr Cys Ser Ile Cys Phe Lys Ser Phe Ala Ser Gly
                165                 170                 175

Gln Ala Leu Gly Gly His Lys Arg Cys His Tyr Asp Gly Gly Asn Asn
            180                 185                 190

Gly Asn Gly Asn Gly Ser Ser Ser Asn Ser Val Glu Leu Val Ala Gly
        195                 200                 205

Ser Asp Val Ser Asp Val Asp Asn Glu Arg Trp Ser Glu Glu Ser Ala
    210                 215                 220

Ile Gly Gly His Arg Gly Phe Asp Leu Asn Leu Pro Ala Asp Gln Val
225                 230                 235                 240

Ser Val Thr Thr Ser
                245


<210> SEQ ID NO 36
<211> LENGTH: 1213
<212> TYPE: DNA
<213> ORGANISM: Oryza sativa

<400> SEQUENCE: 36

aattcggcac gaggccacac agcaaccagc cagctgccac actagcttga ggcgagcgag      60

cgaagcttag ctagcggata gaacaagtcg tcgatctgct tgctgctttt gtgaattgcg     120

gtggaagcat gtcgagcgcg tcgtccatgg aagcgctcca cgccgcggtg ctcaaggagg     180

agcagcagca gcacgaggtg gaggaggcga cggtcgtgac gagcagcagc gccacgagcg     240

gggaggaggg cggacacctg ccccaggggt gggcgaagcg gaagcggtcg cgccgccagc     300

gatcggagga ggagaacctc gcgctctgcc tcctcatgct cgcccgcggc ggccaccacc     360

gcgtccaggc gccgcctccg ctctcggctt cggcgccccc gccggcaggt gcggagttca     420

agtgctccgt ctgcggcaag tccttcagct cctaccaggc gctcggcggc cacaagacga     480

gccaccgggt caagctgccg actccgcccg cagctcccgt cttggctccc gcccccgtcg     540

ccgccttgct gccttccgcc gaggaccgcg agccagccac gtcatccacc gccgcgtcct     600

ccgacggcat gaccaacaga gtccacaggt gttccatctg ccagaaggag ttccccaccg     660

ggcaggcgct cggcgggcac aagaggaagc actacgacgg tggcgtaggc gccggcgccg     720

gcgcatcttc aaccgagctc ctggccacgg tggccgccga gtccgaggtg ggaagctccg     780

gcaacggcca gtccgccacc cgggcgttcg acctcaacct cccggccgtg ccggagttcg     840

tgtggcggcc gtgctccaag ggcaagaaga tgtgggacga ggaggaggag gtccagagcc     900

ccctcgcctt caagaagccc cggcttctca ccgcgtaatt cagcagctgc acggatccga     960

tccgtcagag tttttgtcta gggagtgaaa ttcagtcgaa acacactatt cgttgattcg    1020

ttttgtgccg ctattgttta atttgttcct gcttttgtac agagcaagcg agtgatacat    1080

agccatacat acagtcatac agatataggt ctagctcttc cttggttctt tgtaacactg    1140

gaactgtacc tgtatctttt acactttgtt ctttgacagt catatattgt agaccaaaaa    1200

aaaaaaaaaa aaa                                                        1213


<210> SEQ ID NO 37
<211> LENGTH: 269
<212> TYPE: PRT
<213> ORGANISM: Oryza sativa

<400> SEQUENCE: 37

Met Ser Ser Ala Ser Ser Met Glu Ala Leu His Ala Ala Val Leu Lys
1               5                   10                  15
```

```
Glu Glu Gln Gln Gln His Glu Val Glu Glu Ala Thr Val Val Thr Ser
            20                  25                  30

Ser Ser Ala Thr Ser Gly Glu Glu Gly Gly His Leu Pro Gln Gly Trp
        35                  40                  45

Ala Lys Arg Lys Arg Ser Arg Arg Gln Arg Ser Glu Glu Glu Asn Leu
    50                  55                  60

Ala Leu Cys Leu Leu Met Leu Ala Arg Gly Gly His His Arg Val Gln
65                  70                  75                  80

Ala Pro Pro Pro Leu Ser Ala Ser Ala Pro Pro Pro Ala Gly Ala Glu
                85                  90                  95

Phe Lys Cys Ser Val Cys Gly Lys Ser Phe Ser Ser Tyr Gln Ala Leu
            100                 105                 110

Gly Gly His Lys Thr Ser His Arg Val Lys Leu Pro Thr Pro Pro Ala
        115                 120                 125

Ala Pro Val Leu Ala Pro Ala Pro Val Ala Ala Leu Leu Pro Ser Ala
    130                 135                 140

Glu Asp Arg Glu Pro Ala Thr Ser Ser Thr Ala Ala Ser Ser Asp Gly
145                 150                 155                 160

Met Thr Asn Arg Val His Arg Cys Ser Ile Cys Gln Lys Glu Phe Pro
                165                 170                 175

Thr Gly Gln Ala Leu Gly Gly His Lys Arg Lys His Tyr Asp Gly Gly
            180                 185                 190

Val Gly Ala Gly Ala Gly Ala Ser Ser Thr Glu Leu Leu Ala Thr Val
        195                 200                 205

Ala Ala Glu Ser Glu Val Gly Ser Ser Gly Asn Gly Gln Ser Ala Thr
    210                 215                 220

Arg Ala Phe Asp Leu Asn Leu Pro Ala Val Pro Glu Phe Val Trp Arg
225                 230                 235                 240

Pro Cys Ser Lys Gly Lys Lys Met Trp Asp Glu Glu Glu Glu Val Gln
                245                 250                 255

Ser Pro Leu Ala Phe Lys Lys Pro Arg Leu Leu Thr Ala
            260                 265
```

<210> SEQ ID NO 38
<211> LENGTH: 528
<212> TYPE: DNA
<213> ORGANISM: Arabidopsis thaliana

<400> SEQUENCE: 38

```
atgaagagag accggtccga ttacgaagaa tccatgaagc atatagacat agtagaaagt     60

ctaatgatgt tatctcgaag tttcgtggtc aaacaaatcg atgtaaagca atctaccgga    120

agcaaaacga accataataa ccacttcgaa tgcaaaacgt gtaaccggaa atttgattcc    180

ttccaagctc ttggaggtca tagagctagc cacaagaaac ctaagctgat cgttgaccaa    240

gaacaggtga agcatcgtaa caaagagaat gatatgcata agtgtacaat ttgcgatcaa    300

atgtttggga ccggtcaagc tctaggcggt cacatgagaa agcataggac gagcatgata    360

accgagcaat cgattgtccc ttctgtggtt tattccagac cggtttttaa tcgttgcagt    420

agcagcaagg agatcttgga cttaaatcta actccattgg aaaatgatct tgtgttaatc    480

tttgggaaga atttggttcc acaaattgat ttgaagtttg tgaattag                 528
```

<210> SEQ ID NO 39
<211> LENGTH: 175
<212> TYPE: PRT
<213> ORGANISM: Arabidopsis thaliana

<400> SEQUENCE: 39

```
Met Lys Arg Asp Arg Ser Asp Tyr Glu Glu Ser Met Lys His Ile Asp
1               5                   10                  15

Ile Val Glu Ser Leu Met Met Leu Ser Arg Ser Phe Val Val Lys Gln
            20                  25                  30

Ile Asp Val Lys Gln Ser Thr Gly Ser Lys Thr Asn His Asn Asn His
        35                  40                  45

Phe Glu Cys Lys Thr Cys Asn Arg Lys Phe Asp Ser Phe Gln Ala Leu
    50                  55                  60

Gly Gly His Arg Ala Ser His Lys Lys Pro Lys Leu Ile Val Asp Gln
65                  70                  75                  80

Glu Gln Val Lys His Arg Asn Lys Glu Asn Asp Met His Lys Cys Thr
                85                  90                  95

Ile Cys Asp Gln Met Phe Gly Thr Gly Gln Ala Leu Gly Gly His Met
            100                 105                 110

Arg Lys His Arg Thr Ser Met Ile Thr Glu Gln Ser Ile Val Pro Ser
        115                 120                 125

Val Val Tyr Ser Arg Pro Val Phe Asn Arg Cys Ser Ser Ser Lys Glu
    130                 135                 140

Ile Leu Asp Leu Asn Leu Thr Pro Leu Glu Asn Asp Leu Val Leu Ile
145                 150                 155                 160

Phe Gly Lys Asn Leu Val Pro Gln Ile Asp Leu Lys Phe Val Asn
                165                 170                 175
```

<210> SEQ ID NO 40
<211> LENGTH: 820
<212> TYPE: DNA
<213> ORGANISM: Saccharum officinarum
<220> FEATURE:
<221> NAME/KEY: modified_base
<222> LOCATION: (406)..(406)
<223> OTHER INFORMATION: a, c, t, g, unknown or other
<220> FEATURE:
<221> NAME/KEY: modified_base
<222> LOCATION: (581)..(582)
<223> OTHER INFORMATION: a, c, t, g, unknown or other
<220> FEATURE:
<221> NAME/KEY: modified_base
<222> LOCATION: (589)..(589)
<223> OTHER INFORMATION: a, c, t, g, unknown or other

<400> SEQUENCE: 40

```
cctaaccagc attagctttt caaatcaaca agcctcgccg tgaccgatcg atggccatca     60

cccacgacga ctacgtctcc ctctgcctca tggcgctcgc agccgcggga ggcggaggcc    120

aagctggttt aacaacgcag tacgctctga acacggctgc ctggacagcg acggcgcaag    180

agtccgagct ccgcttccgg tgctccgtct gtggcaaggc cttcgcgtcg caccaggcac    240

tgggcgggca caaggccagc caccgcaagc cgacgctcgt acaggcacat gcgtcgtcct    300

cagccggagg cgcggcgtcg tcgtcggtaa caatgacctc ggccgtaggc agcagtgggc    360

aggggaggca caggtgcacg gtgtgccatc ggagcttcgc gacggngcaa gcgctcggcg    420

ggcacaagag gtgccattac tgggacgggc tctcggtgtc gctcaccgcg tcgtcggcgc    480

catcggggtc cgggtcgacc gtcaagggct ttgatctgaa tttggtgccg gtgccgcccg    540

cgatggccgc caacgctgcg acaaggtggg gagaggagaa nnaagtcana aacccttggc    600

ggtcaagaga aggcggcttg ccggtccgtc ttggacccta atttaacgat ttagaagtcc    660

ttttttaat aattaagagt tcttttgaag aaggttgtaa agttttcgaa ccttgttctt     720

ttaatggatt tgggtgctgg cgaaatttta aaactggatt taaatttgcg ctcactcttt    780
```

```
tttttattt tttacaccct ttttttttt tagaagaaga                         820


<210> SEQ ID NO 41
<211> LENGTH: 1509
<212> TYPE: DNA
<213> ORGANISM: Arabidopsis thaliana

<400> SEQUENCE: 41

ttcctttctc ttcctctctc tctctcttca ccatgactga tccttattcc aatttcttca     60

cagactggtt caagtctaat ccttttcacc attaccctaa ttcctccact aacccctctc    120

ctcatcctct tcctcctgtt actcctccct cttccttctt cttcttccct caatccggag    180

acctccgccg tccaccgccg ccaccaactc ctcctccttc tcctcctctc cgagaagccc    240

tccctctcct cagcctcagc cccgccaaca aacaacaaga ccaccatcac aaccatgacc    300

accttattca agaaccacct tcaacctcca tggatgtcga ctacgatcat caccatcaag    360

atgatcatca taacctcgat gacgatgacc atgacgtcac cgttgctctt cacataggcc    420

ttccaagccc tagtgctcaa gagatggcct ctttgctcat gatgtcttct tcttcctctt    480

cctcgaggac cactcatcat cacgaggaca tgaatcacaa gaaagacctc gaccatgagt    540

acagccacgg agctgtcgga ggaggagaag atgacgatga agattcagtc ggcggagacg    600

gcggctgtag aatcagcaga ctcaacaagg gtcaatattg gatccctaca ccttctcaga    660

ttctcattgg ccctactcag ttctcatgtc ctgtttgctt caaaaccttc aacagataca    720

ataacatgca gatgcatatg tggggacatg gatcacaata cagaaaagga cctgaatctc    780

taaggggaac acaaccaaca ggaatgctaa ggcttccgtg ctattgctgc gccccaggct    840

gtcgcaacaa cattgaccat ccaagggcaa agcctctcaa agacttcaga acccttcaaa    900

cacattacaa gagaaaacat gggatcaaac ctttcatgtg taggaaatgt ggaaaggctt    960

tcgcagtccg aggggactgg agaacacatg agaagaattg tggcaaactt tggtattgca   1020

tatgtggatc tgatttcaag cacaagagat ctctcaaaga tcacatcaag gcttttggga   1080

atggtcatgg agcctacgga attgatgggt ttgatgaaga agatgagcct gcctctgagg   1140

tagaacaatt agacaatgat catgagtcaa tgcagtctaa atagcttata tatattacta   1200

taagtactaa gtaattcggt atatatatta attataagaa acctaaatct atggaccaag   1260

ttttgatgga ggtagggctt ttcaaactaa aagctatatc atctaattga tcataggaaa   1320

aaaatgaatc aagagcactt ggaaaatttt aaattgtatc tttagcttcc tagttaaatt   1380

tattgcaaga caatgtagca gtctaaccaa tgaggttccc aacggtttat ttctatttgt   1440

atattatttt gtcattagct tcacctttcg ttaattcgaa ggacataact tataaatgtt   1500

taaattatg                                                            1509


<210> SEQ ID NO 42
<211> LENGTH: 383
<212> TYPE: PRT
<213> ORGANISM: Arabidopsis thaliana

<400> SEQUENCE: 42

Met Thr Asp Pro Tyr Ser Asn Phe Phe Thr Asp Trp Phe Lys Ser Asn
1               5                   10                  15

Pro Phe His His Tyr Pro Asn Ser Ser Thr Asn Pro Ser Pro His Pro
            20                  25                  30

Leu Pro Pro Val Thr Pro Pro Ser Ser Phe Phe Phe Phe Pro Gln Ser
        35                  40                  45
```

```
Gly Asp Leu Arg Arg Pro Pro Pro Pro Pro Thr Pro Pro Pro Ser Pro
    50                  55                  60

Pro Leu Arg Glu Ala Leu Pro Leu Leu Ser Leu Ser Pro Ala Asn Lys
65                  70                  75                  80

Gln Gln Asp His His His Asn His Asp His Leu Ile Gln Glu Pro Pro
                85                  90                  95

Ser Thr Ser Met Asp Val Asp Tyr Asp His His His Gln Asp Asp His
            100                 105                 110

His Asn Leu Asp Asp Asp Asp His Asp Val Thr Val Ala Leu His Ile
        115                 120                 125

Gly Leu Pro Ser Pro Ser Ala Gln Glu Met Ala Ser Leu Leu Met Met
    130                 135                 140

Ser Ser Ser Ser Ser Ser Ser Arg Thr Thr His His His Glu Asp Met
145                 150                 155                 160

Asn His Lys Lys Asp Leu Asp His Glu Tyr Ser His Gly Ala Val Gly
                165                 170                 175

Gly Gly Glu Asp Asp Asp Glu Asp Ser Val Gly Gly Asp Gly Gly Cys
            180                 185                 190

Arg Ile Ser Arg Leu Asn Lys Gly Gln Tyr Trp Ile Pro Thr Pro Ser
        195                 200                 205

Gln Ile Leu Ile Gly Pro Thr Gln Phe Ser Cys Pro Val Cys Phe Lys
    210                 215                 220

Thr Phe Asn Arg Tyr Asn Asn Met Gln Met His Met Trp Gly His Gly
225                 230                 235                 240

Ser Gln Tyr Arg Lys Gly Pro Glu Ser Leu Arg Gly Thr Gln Pro Thr
                245                 250                 255

Gly Met Leu Arg Leu Pro Cys Tyr Cys Cys Ala Pro Gly Cys Arg Asn
            260                 265                 270

Asn Ile Asp His Pro Arg Ala Lys Pro Leu Lys Asp Phe Arg Thr Leu
        275                 280                 285

Gln Thr His Tyr Lys Arg Lys His Gly Ile Lys Pro Phe Met Cys Arg
    290                 295                 300

Lys Cys Gly Lys Ala Phe Ala Val Arg Gly Asp Trp Arg Thr His Glu
305                 310                 315                 320

Lys Asn Cys Gly Lys Leu Trp Tyr Cys Ile Cys Gly Ser Asp Phe Lys
                325                 330                 335

His Lys Arg Ser Leu Lys Asp His Ile Lys Ala Phe Gly Asn Gly His
            340                 345                 350

Gly Ala Tyr Gly Ile Asp Gly Phe Asp Glu Glu Asp Glu Pro Ala Ser
        355                 360                 365

Glu Val Glu Gln Leu Asp Asn Asp His Glu Ser Met Gln Ser Lys
    370                 375                 380
```

<210> SEQ ID NO 43
<211> LENGTH: 1303
<212> TYPE: DNA
<213> ORGANISM: Arabidopsis thaliana

<400> SEQUENCE: 43

```
atctacacac tactactcac atctcatctc tctctagcac atacccatca aaccatatag     60

atacggtgct tttattcttg atcttcttct tcttctttgt cttctcctca gagtcatgtc    120

taatccagct tgttcgaatc tcttcaacaa tggatgtgac cataatagct tcaactattc    180

cacttctctc tcttacattt acaactctca cggtagctac tattactcta ataccacaaa    240

ccctaattac attaatcata ctcataccac ttccacttcc cctaactcac ccccactaag    300
```

```
agaagctctt cctcttctta gcttaagccc cataaggcac caagaacaac aagaccaaca    360
ctatttcatg gacacccatc aaattagctc ttcaaacttt cttgatgatc ctcttgtgac    420
tgtggatctt catctagggt taccaaacta cggtgttggt gagagcatta ggagcaatat    480
tgctcctgat gcaaccacgg acgagcaaga tcaagatcat gaccgaggag tagaagtcac    540
agttgagtcc caccttgatg atgatgatga tcatcatgga gatctacaca gaggtcatca    600
ctattggatt cctactcctt ctcagatttt gattggtcct acacagttca cttgtcctct    660
ttgcttcaag acattcaaca gatacaacaa catgcagatg cacatgtggg gacacggctc    720
acaatacaga aagggaccag aatccttaag aggaacccaa ccaacaggaa tgctaagact    780
accatgtttc tgctgtgcac ccggttgcaa gaacaacatt gaccacccac gagccaagcc    840
tcttaaggac tttcgaaccc tccaaacaca ttacaaacgt aaacatgggt ctaaaccatt    900
tgcttgtcgt atgtgtggta aggcctttgc agtgaaagga gattggagaa cgcatgagaa    960
gaattgtgga aagctttggt attgctcttg tggctcggat tttaagcaca agaggtcgct   1020
taaggaccat gtcaaggcct ttggaaatgg tcatgttcct tgtgggattg atagttttgg   1080
aggagatcat gaggactact atgatgctgc ttctgatatc gagcaataag atgatagcaa   1140
caacaatgag tgttaattag ggttttgtt tatttttcct ctcatgcatt agttgattgt   1200
atgcacgtgt tctttagttt tgttcttcgg atctttgttt tattttgttt tgagctgttt   1260
ttttttaat tactaagaag ttaattatca tctaaagatt ttc                       1303
```

<210> SEQ ID NO 44
<211> LENGTH: 337
<212> TYPE: PRT
<213> ORGANISM: Arabidopsis thaliana

<400> SEQUENCE: 44

```
Met Ser Asn Pro Ala Cys Ser Asn Leu Phe Asn Asn Gly Cys Asp His
1               5                   10                  15

Asn Ser Phe Asn Tyr Ser Thr Ser Leu Ser Tyr Ile Tyr Asn Ser His
            20                  25                  30

Gly Ser Tyr Tyr Tyr Ser Asn Thr Thr Asn Pro Asn Tyr Ile Asn His
        35                  40                  45

Thr His Thr Thr Ser Thr Ser Pro Asn Ser Pro Pro Leu Arg Glu Ala
    50                  55                  60

Leu Pro Leu Leu Ser Leu Ser Pro Ile Arg His Gln Glu Gln Gln Asp
65                  70                  75                  80

Gln His Tyr Phe Met Asp Thr His Gln Ile Ser Ser Ser Asn Phe Leu
                85                  90                  95

Asp Asp Pro Leu Val Thr Val Asp Leu His Leu Gly Leu Pro Asn Tyr
            100                 105                 110

Gly Val Gly Glu Ser Ile Arg Ser Asn Ile Ala Pro Asp Ala Thr Thr
        115                 120                 125

Asp Glu Gln Asp Gln Asp His Asp Arg Gly Val Glu Val Thr Val Glu
    130                 135                 140

Ser His Leu Asp Asp Asp Asp Asp His His Gly Asp Leu His Arg Gly
145                 150                 155                 160

His His Tyr Trp Ile Pro Thr Pro Ser Gln Ile Leu Ile Gly Pro Thr
                165                 170                 175

Gln Phe Thr Cys Pro Leu Cys Phe Lys Thr Phe Asn Arg Tyr Asn Asn
            180                 185                 190

Met Gln Met His Met Trp Gly His Gly Ser Gln Tyr Arg Lys Gly Pro
```

```
        195                 200                 205

Glu Ser Leu Arg Gly Thr Gln Pro Thr Gly Met Leu Arg Leu Pro Cys
    210                 215                 220

Phe Cys Cys Ala Pro Gly Cys Lys Asn Asn Ile Asp His Pro Arg Ala
225                 230                 235                 240

Lys Pro Leu Lys Asp Phe Arg Thr Leu Gln Thr His Tyr Lys Arg Lys
                245                 250                 255

His Gly Ser Lys Pro Phe Ala Cys Arg Met Cys Gly Lys Ala Phe Ala
            260                 265                 270

Val Lys Gly Asp Trp Arg Thr His Glu Lys Asn Cys Gly Lys Leu Trp
        275                 280                 285

Tyr Cys Ser Cys Gly Ser Asp Phe Lys His Lys Arg Ser Leu Lys Asp
    290                 295                 300

His Val Lys Ala Phe Gly Asn Gly His Val Pro Cys Gly Ile Asp Ser
305                 310                 315                 320

Phe Gly Gly Asp His Glu Asp Tyr Tyr Asp Ala Ala Ser Asp Ile Glu
                325                 330                 335

Gln


<210> SEQ ID NO 45
<211> LENGTH: 495
<212> TYPE: DNA
<213> ORGANISM: Arabidopsis thaliana

<400> SEQUENCE: 45

atggttgcga gaagtgagga agttgagata gtggaagata cggcggcgaa atgtttgatg      60

ttgttatcaa gagttggaga atgcggcgga ggaggagaga aacgagtttt ccgatgcaag     120

acttgtctta aagagttttc gtcgtttcaa gctttgggag gtcatcgtgc aagccacaag     180

aaactcatta acagtagcga tccatcactt cttggatcct tgtctaacaa gaaaactaaa     240

acggcgacgt ctcatccttg tccgatatgt ggcgtggagt ttccgatggg gcaagctctt     300

ggtggtcaca tgaggagaca taggagtgag aaagcctcac caggcacgtt ggttacacgt     360

tctttttac cggagacgac gacggtgacg actttgaaaa aatcgagtag tgggaagaga     420

gtggcttgtt tggacttaga ttcgatggag agtttagtca attggaagtt ggagttggga     480

agaacgattt cttga                                                      495


<210> SEQ ID NO 46
<211> LENGTH: 164
<212> TYPE: PRT
<213> ORGANISM: Arabidopsis thaliana

<400> SEQUENCE: 46

Met Val Ala Arg Ser Glu Glu Val Glu Ile Val Glu Asp Thr Ala Ala
1               5                   10                  15

Lys Cys Leu Met Leu Leu Ser Arg Val Gly Glu Cys Gly Gly Gly Gly
            20                  25                  30

Glu Lys Arg Val Phe Arg Cys Lys Thr Cys Leu Lys Glu Phe Ser Ser
        35                  40                  45

Phe Gln Ala Leu Gly Gly His Arg Ala Ser His Lys Lys Leu Ile Asn
    50                  55                  60

Ser Ser Asp Pro Ser Leu Leu Gly Ser Leu Ser Asn Lys Lys Thr Lys
65                  70                  75                  80

Thr Ala Thr Ser His Pro Cys Pro Ile Cys Gly Val Glu Phe Pro Met
                85                  90                  95
```

```
Gly Gln Ala Leu Gly Gly His Met Arg Arg His Arg Ser Glu Lys Ala
            100                 105                 110

Ser Pro Gly Thr Leu Val Thr Arg Ser Phe Leu Pro Glu Thr Thr Thr
        115                 120                 125

Val Thr Thr Leu Lys Lys Ser Ser Ser Gly Lys Arg Val Ala Cys Leu
    130                 135                 140

Asp Leu Asp Ser Met Glu Ser Leu Val Asn Trp Lys Leu Glu Leu Gly
145                 150                 155                 160

Arg Thr Ile Ser


<210> SEQ ID NO 47
<211> LENGTH: 1209
<212> TYPE: DNA
<213> ORGANISM: Arabidopsis thaliana

<400> SEQUENCE: 47

atggaagacg aacatcaaga tctccataaa cccattaatg gagctttgcg agacctcaag      60

attactcggt cacagaaaga aacagaaaag tctacgaacc aacagcaaga tgttacttgt     120

tactatggtc taagggaaaa ctcgaagaag aaaacccagg aatctccgga accaatgaag     180

aagattttgt ttcgatgcga agaatgtgga aaagggtttc ggtacgagaa atattttaag     240

aatcatcgct cgatgatgca tttatcgccg aacgagaagg tttgtgaaga atccttgatg     300

actctgtctc gtagccttgg gtttgtgaag aagaagaaaa gatcaagact tggtaggtct     360

gggaagactt tatttactac gtttcttgaa ccgagttcta tttttgatgc gactgatgaa     420

gaattagaag tggcggattg tttgattcta ttgtctaaga gtgctcccaa ggttgtagac     480

gaattgaaaa gtctttctga ggcagtacgt gttactcctg aaacacctga aagtagctat     540

gatttgggtt gtttgctcaa caagaaaccg agaaaaggtg gtgaattgga atctggggtt     600

ttaagtaatg agcaaagact tatggaagaa gggtttagta gttatggaac atcgaaagaa     660

ccagctagct tcttgagaga cgaaaacaga ttggatcagc agaaacggag aaaagatggt     720

gaatttgaat ccggactttt gagtaatgag caaagactgc tagaagaaga gattactact     780

cctgtgacat tcaaaggtcc agcgagttcc ttgagacaca agtgtgcttt ggatcgaaat     840

ggaggtgaat ttggtcctga gtttttgagt aatgagcaaa cactgatgga agaaacatgg     900

aaagaaccag tgagtttctt agaagataag catgaatttg atcagcggaa aatgcgagaa     960

gctggcgact ttgaatctag gttttacaga attgagcttg gagtaggagc tatggagtgt    1020

acttcttcag atactgatat gctcacgcaa tctgataaga agaacgttga gcatcgatgc    1080

aggttgtgca acaagatatt ctcgtcttat caagctctag gggtcatca gacgtttcat     1140

cggatgagca aatgtaagaa caagaagaat ggcatagagg aatcagttga acccaggatg    1200

actctgtga                                                            1209


<210> SEQ ID NO 48
<211> LENGTH: 402
<212> TYPE: PRT
<213> ORGANISM: Arabidopsis thaliana

<400> SEQUENCE: 48

Met Glu Asp Glu His Gln Asp Leu His Lys Pro Ile Asn Gly Ala Leu
1               5                   10                  15

Arg Asp Leu Lys Ile Thr Arg Ser Gln Lys Glu Thr Glu Lys Ser Thr
            20                  25                  30

Asn Gln Gln Gln Asp Val Thr Cys Tyr Tyr Gly Leu Arg Glu Asn Ser
        35                  40                  45
```

```
Lys Lys Lys Thr Gln Glu Ser Pro Glu Pro Met Lys Lys Ile Leu Phe
    50                  55                  60

Arg Cys Glu Glu Cys Gly Lys Gly Phe Arg Tyr Glu Lys Tyr Phe Lys
65                  70                  75                  80

Asn His Arg Ser Met Met His Leu Ser Pro Asn Glu Lys Val Cys Glu
                85                  90                  95

Glu Ser Leu Met Thr Leu Ser Arg Ser Leu Gly Phe Val Lys Lys Lys
            100                 105                 110

Lys Arg Ser Arg Leu Gly Arg Ser Gly Lys Thr Leu Phe Thr Thr Phe
        115                 120                 125

Leu Glu Pro Ser Ser Ile Phe Asp Ala Thr Asp Glu Glu Leu Glu Val
    130                 135                 140

Ala Asp Cys Leu Ile Leu Leu Ser Lys Ser Ala Pro Lys Val Val Asp
145                 150                 155                 160

Glu Leu Lys Ser Leu Ser Glu Ala Val Arg Val Thr Pro Glu Thr Pro
                165                 170                 175

Glu Ser Ser Tyr Asp Leu Gly Cys Leu Leu Asn Lys Lys Pro Arg Lys
            180                 185                 190

Gly Gly Glu Leu Glu Ser Gly Val Leu Ser Asn Glu Gln Arg Leu Met
        195                 200                 205

Glu Glu Gly Phe Ser Ser Tyr Gly Thr Ser Lys Glu Pro Ala Ser Phe
    210                 215                 220

Leu Arg Asp Glu Asn Arg Leu Asp Gln Gln Lys Arg Arg Lys Asp Gly
225                 230                 235                 240

Glu Phe Glu Ser Gly Leu Leu Ser Asn Glu Gln Arg Leu Leu Glu Glu
                245                 250                 255

Glu Ile Thr Thr Pro Val Thr Phe Lys Gly Pro Ala Ser Ser Leu Arg
            260                 265                 270

His Lys Cys Ala Leu Asp Arg Asn Gly Gly Glu Phe Gly Pro Glu Phe
        275                 280                 285

Leu Ser Asn Glu Gln Thr Leu Met Glu Glu Thr Trp Lys Glu Pro Val
    290                 295                 300

Ser Phe Leu Glu Asp Lys His Glu Phe Asp Gln Arg Lys Met Arg Glu
305                 310                 315                 320

Ala Gly Asp Phe Glu Ser Arg Phe Tyr Arg Ile Glu Leu Gly Val Gly
                325                 330                 335

Ala Met Glu Cys Thr Ser Ser Asp Thr Asp Met Leu Thr Gln Ser Asp
            340                 345                 350

Lys Lys Asn Val Glu His Arg Cys Arg Leu Cys Asn Lys Ile Phe Ser
        355                 360                 365

Ser Tyr Gln Ala Leu Gly Gly His Gln Thr Phe His Arg Met Ser Lys
    370                 375                 380

Cys Lys Asn Lys Lys Asn Gly Ile Glu Glu Ser Val Glu Pro Arg Met
385                 390                 395                 400

Thr Leu


<210> SEQ ID NO 49
<211> LENGTH: 1087
<212> TYPE: DNA
<213> ORGANISM: Arabidopsis thaliana

<400> SEQUENCE: 49

cttgttagtt cactccacat aataaacacc aaagatttca ttctcttctc cataatttcg      60

aagtttcttg aattgggttt gtttcttgat ttgtttcttg aattgggttt tggtcttctt     120
```

```
ttcttactat atttggatat gatgatgggt caagatgagg ttgggagtga tcagacgcaa    180

atcataaaag ggaaacgtac gaagcgacaa agatcgtctt cgacgtttgt ggtgacggcg    240

gcgacaacag tgacttcaac aagttcatcg gccggtggaa gtggaggaga aagagctgtt    300

tcagatgaat acaactcggc ggtttcgtct ccggtgacta ctgattgtac gcaagaagaa    360

gaagacatgg cgatttgtct catcatgtta gctcgtggga cagttcttcc atcgccggat    420

ctcaagaact cgagaaaaat tcatcagaag atttcgtcgg agaattctag tttctatgtg    480

tacgagtgta aaacgtgtaa ccggacgttt tcgtcgttcc aagcacttgg tggacacaga    540

gcgagccaca agaagccgag gacgtcgact gaggaaaaga ctagactacc cctgacgcaa    600

cccaagtcta gtgcatcaga agaagggcaa aacagtcatt tcaaagtttc cggctcagcc    660

ctagcttcac aggcaagtaa catcatcaac aaggcaaaca aagtacacga gtgttccatc    720

tgcggttctg agttcacttc cgggcaagct ctcggtggtc acatgaggcg gcacaggaca    780

gccgtaacca cgattagccc cgttgcagcc accgcagaag taagcagaaa cagtacagag    840

gaagagattg agatcaatat aggccgttcg atggaacagc agaggaaata tctaccgttg    900

gatcttaatc taccagcacc aggagatgat ctaagagagt ccaagtttca agggatagta    960

ttctcagcaa caccagcgtt aatagattgt cattactagt tgttttttt actacataat    1020

atgatgaaat atttgtgaat tcttcttact tactactata ttgttgatca aaaaaaaaaa    1080

aaaaaaa                                                              1087
```

```
<210> SEQ ID NO 50
<211> LENGTH: 284
<212> TYPE: PRT
<213> ORGANISM: Arabidopsis thaliana

<400> SEQUENCE: 50

Met Gly Gln Asp Glu Val Gly Ser Asp Gln Thr Gln Ile Ile Lys Gly
1               5                   10                  15

Lys Arg Thr Lys Arg Gln Arg Ser Ser Ser Thr Phe Val Val Thr Ala
            20                  25                  30

Ala Thr Thr Val Thr Ser Thr Ser Ser Ser Ala Gly Gly Ser Gly Gly
        35                  40                  45

Glu Arg Ala Val Ser Asp Glu Tyr Asn Ser Ala Val Ser Ser Pro Val
    50                  55                  60

Thr Thr Asp Cys Thr Gln Glu Glu Glu Asp Met Ala Ile Cys Leu Ile
65                  70                  75                  80

Met Leu Ala Arg Gly Thr Val Leu Pro Ser Pro Asp Leu Lys Asn Ser
                85                  90                  95

Arg Lys Ile His Gln Lys Ile Ser Ser Glu Asn Ser Ser Phe Tyr Val
            100                 105                 110

Tyr Glu Cys Lys Thr Cys Asn Arg Thr Phe Ser Ser Phe Gln Ala Leu
        115                 120                 125

Gly Gly His Arg Ala Ser His Lys Lys Pro Arg Thr Ser Thr Glu Glu
    130                 135                 140

Lys Thr Arg Leu Pro Leu Thr Gln Pro Lys Ser Ser Ala Ser Glu Glu
145                 150                 155                 160

Gly Gln Asn Ser His Phe Lys Val Ser Gly Ser Ala Leu Ala Ser Gln
                165                 170                 175

Ala Ser Asn Ile Ile Asn Lys Ala Asn Lys Val His Glu Cys Ser Ile
            180                 185                 190

Cys Gly Ser Glu Phe Thr Ser Gly Gln Ala Leu Gly Gly His Met Arg
```

-continued

```
        195                 200                 205

Arg His Arg Thr Ala Val Thr Thr Ile Ser Pro Val Ala Ala Thr Ala
    210                 215                 220

Glu Val Ser Arg Asn Ser Thr Glu Glu Glu Ile Glu Ile Asn Ile Gly
225                 230                 235                 240

Arg Ser Met Glu Gln Gln Arg Lys Tyr Leu Pro Leu Asp Leu Asn Leu
                245                 250                 255

Pro Ala Pro Gly Asp Asp Leu Arg Glu Ser Lys Phe Gln Gly Ile Val
            260                 265                 270

Phe Ser Ala Thr Pro Ala Leu Ile Asp Cys His Tyr
        275                 280


<210> SEQ ID NO 51
<211> LENGTH: 6
<212> TYPE: PRT
<213> ORGANISM: Arabidopsis thaliana
<220> FEATURE:
<221> NAME/KEY: MOD_RES
<222> LOCATION: (3)..(3)
<223> OTHER INFORMATION: Ala, Cys, Phe, Gly, His, Ile, Lys, Leu, Met,
      Arg, Thr, Val, Trp or Tyr

<400> SEQUENCE: 51

Gln Ala Xaa Gly Gly His
1               5


<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 52

His His His His His His
1               5
```